(12) United States Patent
Kovacs et al.

(10) Patent No.: US 10,130,273 B2
(45) Date of Patent: Nov. 20, 2018

(54) DEVICE AND METHOD HAVING AUTOMATIC USER-RESPONSIVE AND USER-SPECIFIC PHYSIOLOGICAL-METER PLATFORM

(71) Applicant: PhysioWave, Inc., Santa Clara, CA (US)

(72) Inventors: Gregory T. Kovacs, Palo Alto, CA (US); Laurent B. Giovangrandi, Palo Alto, CA (US); Robert Bruce Darling, Lake Forest Park, WA (US)

(73) Assignee: Physiowave, Inc., Menlo Park, CA (US)

( * ) Notice: Subject to any disclaimer, the term of this patent is extended or adjusted under 35 U.S.C. 154(b) by 591 days.

(21) Appl. No.: 14/338,266

(22) Filed: Jul. 22, 2014

(65) Prior Publication Data

US 2015/0359486 A1 Dec. 17, 2015

Related U.S. Application Data

(63) Continuation-in-part of application No. 14/332,140, filed on Jul. 15, 2014, now Pat. No. 9,943,241.
(Continued)

(51) Int. Cl.
*A61B 5/00* (2006.01)
*A61B 5/0245* (2006.01)
(Continued)

(52) U.S. Cl.
CPC ........ *A61B 5/0245* (2013.01); *A61B 5/02444* (2013.01); *A61B 5/0408* (2013.01);
(Continued)

(58) Field of Classification Search
CPC ... A61B 5/0245; A61B 5/0075; A61B 5/0077; A61B 5/02444; A61B 5/0408;
(Continued)

(56) References Cited

U.S. PATENT DOCUMENTS 3,702,113 A 11/1972 Blockley et al.
4,195,643 A 4/1980 Pratt, Jr.
(Continued)

FOREIGN PATENT DOCUMENTS

DE 202009012748 12/2009
EP 0329306 A1 2/1989
(Continued)

OTHER PUBLICATIONS

J. Alametsä et al. "Ballistocardiogaphic studies with acceleration and electromechanical film sensors." Medical Engineering & Physics 31 (2009), p. 1154-1165.
(Continued)

*Primary Examiner* — John R Downey
*Assistant Examiner* — Shirely Jian
(74) *Attorney, Agent, or Firm* — Crawford Maunu PLLC

(57) ABSTRACT

Aspects of the present disclosure are directed to a CPU and a memory circuit that has user-corresponding data stored on the memory circuit, and a platform over which a plurality of electrodes are interleaved, and configured for engaging the user. While the plurality of electrodes is concurrently contacting a limb or other extremity of the user, measurement signals are obtained from the plurality of electrodes. Based on a plurality of impedance-measurement signals being obtained from the electrodes, signals are generated that correspond to cardiovascular timings specific to the user. In such aspects of the present disclosure, pulse characteristic signals are determined based on the plurality of impedance-measurement signals and comparisons of user-obtained data are made relative to user-data profiles stored in the memory circuit.

22 Claims, 28 Drawing Sheets

Related U.S. Application Data

(60) Provisional application No. 62/011,466, filed on Jun. 12, 2014.

(51) Int. Cl.

| | | |
|---|---|---|
| *G01R 27/02* | (2006.01) | |
| *A61B 5/024* | (2006.01) | |
| *A61B 5/0408* | (2006.01) | |
| *A61B 5/053* | (2006.01) | |
| *G01G 19/50* | (2006.01) | |
| *A61B 5/04* | (2006.01) | |
| *A61B 5/11* | (2006.01) | |
| *A61B 5/0295* | (2006.01) | |
| *A61B 5/0205* | (2006.01) | |

(52) U.S. Cl.
CPC .......... *A61B 5/0535* (2013.01); *A61B 5/0537* (2013.01); *A61B 5/1113* (2013.01); *A61B 5/72* (2013.01); *G01G 19/50* (2013.01); *G01R 27/02* (2013.01); *A61B 5/024* (2013.01); *A61B 5/0205* (2013.01); *A61B 5/0295* (2013.01); *A61B 5/04012* (2013.01); *A61B 5/1102* (2013.01); *A61B 5/6844* (2013.01); *A61B 5/74* (2013.01); *A61B 2560/0209* (2013.01); *A61B 2576/00* (2013.01)

(58) Field of Classification Search
CPC ... A61B 5/04085; A61B 5/0432; A61B 5/044; A61B 5/0535; A61B 5/0537; A61B 5/1113; A61B 5/72; A61B 5/7405; A61B 5/7455; A61B 2560/0209; A61B 2576/00; A61B 1/00025; A61B 1/00032; A61B 1/00036; A61B 2560/0204; G01G 19/50; G01R 27/02
USPC .................. 600/300–301; 340/539.12, 686.6
See application file for complete search history.

(56) References Cited

U.S. PATENT DOCUMENTS

| | | | |
|---|---|---|---|
| 4,362,164 A | 12/1982 | Little et al. | |
| 4,557,271 A | 12/1985 | Stoller et al. | |
| 4,657,025 A | 4/1987 | Orlando | |
| 4,679,569 A | 7/1987 | Lee | |
| 4,765,321 A | 8/1988 | Mohri | |
| 4,836,215 A | 6/1989 | Lee | |
| 4,947,857 A | 8/1990 | Albert et al. | |
| 4,958,638 A | 9/1990 | Sharpe et al. | |
| 5,314,389 A | 5/1994 | Dotan | |
| 5,431,170 A | 7/1995 | Mathews | |
| 5,620,003 A | 4/1997 | Sepponen | |
| 5,678,562 A | 10/1997 | Sellers | |
| 5,682,902 A | 11/1997 | Herleikson | |
| 5,701,894 A | 12/1997 | Cherry et al. | |
| 5,750,937 A | 5/1998 | Johnson et al. | |
| 5,782,238 A | 7/1998 | Beitler | |
| 5,833,623 A | 11/1998 | Mann et al. | |
| 6,047,203 A | 4/2000 | Sackner et al. | |
| 6,080,110 A | 6/2000 | Thorgersen | |
| 6,168,563 B1 | 1/2001 | Brown | |
| 6,198,394 B1 | 3/2001 | Jacobsen et al. | |
| 6,205,547 B1 | 3/2001 | Davis | |
| 6,228,033 B1 | 5/2001 | Koobi et al. | |
| 6,256,532 B1* | 7/2001 | Cha ..................... | A61B 5/0537 177/245 |
| 6,292,690 B1* | 9/2001 | Petrucelli ................ | A61B 5/05 600/547 |
| 6,331,162 B1 | 12/2001 | Mitchell | |
| 6,454,708 B1 | 9/2002 | Ferguson et al. | |
| 6,454,719 B1 | 9/2002 | Greenhut | |
| 6,516,221 B1 | 2/2003 | Hirouchi et al. | |
| 6,549,639 B1* | 4/2003 | Genest .................. | A43D 1/025 382/100 |
| 6,551,252 B2 | 4/2003 | Sackner et al. | |
| 6,559,448 B1* | 5/2003 | Muller ................. | G08B 13/193 250/340 |
| 6,594,759 B1 | 7/2003 | Wang | |
| 6,640,134 B2 | 10/2003 | Raymond et al. | |
| 6,685,634 B1 | 2/2004 | Fry | |
| 6,702,754 B2 | 3/2004 | Ogura et al. | |
| 6,705,990 B1* | 3/2004 | Gallant ................ | A61B 5/0205 128/903 |
| 6,714,814 B2* | 3/2004 | Yamada ............... | A61B 5/0537 600/384 |
| 6,734,856 B2* | 5/2004 | Ishikawa .............. | A61B 5/0537 345/440 |
| 6,755,783 B2 | 6/2004 | Cosentino et al. | |
| 6,783,498 B2 | 8/2004 | Sackner et al. | |
| 6,790,178 B1 | 9/2004 | Mault et al. | |
| 6,814,705 B2 | 11/2004 | Kawaguchi | |
| 6,847,892 B2 | 1/2005 | Zhou et al. | |
| 6,875,174 B2 | 4/2005 | Braun et al. | |
| 6,898,299 B1 | 5/2005 | Brooks | |
| 6,962,566 B2 | 11/2005 | Quistgaard et al. | |
| 6,963,035 B2 | 11/2005 | Honda et al. | |
| 7,137,955 B2 | 11/2006 | Bartels et al. | |
| 7,257,438 B2 | 8/2007 | Kinast | |
| 7,313,435 B2* | 12/2007 | Nakada ................ | A61B 5/0537 600/547 |
| 7,316,648 B2 | 1/2008 | Kelly et al. | |
| 7,382,247 B2 | 6/2008 | Welch et al. | |
| 7,384,410 B2 | 6/2008 | Eggers et al. | |
| 7,417,536 B2 | 8/2008 | Lakshmanan et al. | |
| 7,459,644 B2 | 12/2008 | Kenmochi | |
| 7,502,643 B2 | 3/2009 | Farringdon et al. | |
| 7,668,588 B2 | 2/2010 | Kovacs | |
| 7,787,946 B2 | 8/2010 | Stahmann et al. | |
| 7,796,013 B2 | 9/2010 | Murakami et al. | |
| 7,846,104 B2 | 12/2010 | MacQuarrie et al. | |
| 7,899,522 B1 | 3/2011 | Koh et al. | |
| 8,369,936 B2 | 2/2013 | Farringdon et al. | |
| 8,452,390 B2* | 5/2013 | Jensen ................. | A61B 5/0537 600/547 |
| 8,473,041 B2 | 6/2013 | Bartnik et al. | |
| 8,475,367 B1 | 7/2013 | Yuen et al. | |
| 8,529,409 B1 | 9/2013 | Lesea-Ames | |
| 8,548,556 B2 | 10/2013 | Jensen | |
| 8,639,226 B2 | 1/2014 | Hutchings et al. | |
| 8,682,424 B2 | 3/2014 | Tsoglin et al. | |
| 8,696,569 B2* | 4/2014 | Yuen .................... | G06F 19/3418 128/920 |
| 8,698,014 B1 | 4/2014 | Walstad | |
| 8,818,499 B2* | 8/2014 | Karo .................... | A61B 5/1072 600/382 |
| 8,858,449 B2 | 10/2014 | Inan et al. | |
| 8,870,780 B2* | 10/2014 | Inan .................... | A61B 5/7207 600/481 |
| 9,011,346 B2 | 4/2015 | Wiard et al. | |
| 9,055,871 B2 | 6/2015 | Inan et al. | |
| 9,215,991 B2 | 12/2015 | Inan et al. | |
| 9,241,637 B2 | 1/2016 | Wiard et al. | |
| 9,498,137 B2* | 11/2016 | Kovacs ................ | A61B 5/0205 |
| 9,549,680 B2* | 1/2017 | Giovangrandi ...... | A61B 5/0295 |
| 2001/0030546 A1* | 10/2001 | Yamada ............... | A61B 5/0537 324/691 |
| 2001/0044588 A1 | 11/2001 | Mault | |
| 2002/0002326 A1 | 1/2002 | Causey, III et al. | |
| 2002/0062090 A1* | 5/2002 | Chai ........................ | A61B 5/05 600/547 |
| 2002/0179338 A1* | 12/2002 | Tanida ................. | A61B 5/0537 177/25.13 |
| 2002/0188205 A1 | 12/2002 | Mills | |
| 2003/0050537 A1 | 3/2003 | Wessel | |
| 2003/0088196 A1 | 5/2003 | Burton | |
| 2003/0126593 A1 | 7/2003 | Mault | |
| 2003/0130567 A1 | 7/2003 | Mault et al. | |
| 2003/0130595 A1 | 7/2003 | Mault | |
| 2003/0149349 A1 | 8/2003 | Jensen | |
| 2003/0197614 A1 | 10/2003 | Smith et al. | |

(56) References Cited

U.S. PATENT DOCUMENTS

| | | |
|---|---|---|
| 2003/0233034 A1 | 12/2003 | Varri et al. |
| 2004/0059242 A1* | 3/2004 | Masuo ............... A61B 5/0537 |
| | | 600/547 |
| 2004/0068379 A1* | 4/2004 | Morgan ............... A01K 29/00 |
| | | 702/19 |
| 2004/0073127 A1 | 4/2004 | Istvan et al. |
| 2004/0097802 A1 | 5/2004 | Cohen |
| 2004/0138517 A1 | 7/2004 | Osorio et al. |
| 2004/0211599 A1* | 10/2004 | Kasinoff ............ G01G 19/4144 |
| | | 177/25.15 |
| 2004/0249258 A1 | 12/2004 | Tupin, Jr. et al. |
| 2005/0004483 A1 | 1/2005 | Lin |
| 2005/0017602 A1 | 1/2005 | Arms et al. |
| 2005/0033124 A1 | 2/2005 | Kelly et al. |
| 2005/0043645 A1 | 2/2005 | Ono et al. |
| 2005/0113703 A1 | 5/2005 | Farringdon et al. |
| 2005/0113712 A1* | 5/2005 | Petrucelli .............. G01G 19/50 |
| | | 600/547 |
| 2005/0119711 A1 | 6/2005 | Cho et al. |
| 2005/0171451 A1 | 8/2005 | Yeo et al. |
| 2005/0203349 A1 | 9/2005 | Nanikashvili |
| 2005/0206518 A1 | 9/2005 | Welch et al. |
| 2005/0247494 A1 | 11/2005 | Montagnino |
| 2005/0283198 A1 | 12/2005 | Haubrich et al. |
| 2006/0049955 A1 | 3/2006 | Blum et al. |
| 2006/0079942 A1 | 4/2006 | Deno et al. |
| 2006/0106646 A1 | 5/2006 | Squilla et al. |
| 2006/0111641 A1 | 5/2006 | Manera et al. |
| 2006/0116589 A1 | 6/2006 | Park |
| 2006/0122525 A1 | 6/2006 | Shusterman |
| 2006/0149139 A1 | 7/2006 | Bonmassar et al. |
| 2006/0154642 A1 | 7/2006 | Scannell |
| 2006/0155589 A1 | 7/2006 | Lane et al. |
| 2007/0055324 A1 | 3/2007 | Thompson et al. |
| 2007/0069887 A1 | 3/2007 | Welch et al. |
| 2007/0161913 A1 | 7/2007 | Farrell et al. |
| 2007/0197878 A1 | 8/2007 | Shklarski |
| 2007/0208232 A1 | 9/2007 | Kovacs |
| 2007/0293770 A1 | 12/2007 | Bour et al. |
| 2008/0027679 A1 | 1/2008 | Shklarski |
| 2008/0073128 A1* | 3/2008 | Umemoto ............ A61B 5/0537 |
| | | 177/5 |
| 2008/0154645 A1 | 6/2008 | Takehara |
| 2008/0161700 A1 | 7/2008 | Sachanandani et al. |
| 2008/0183090 A1 | 7/2008 | Farringdon et al. |
| 2008/0194975 A1 | 8/2008 | MacQuarrie et al. |
| 2008/0208009 A1 | 8/2008 | Shklarski |
| 2008/0221404 A1* | 9/2008 | Tso ................... A61B 5/02055 |
| | | 600/301 |
| 2008/0246629 A1 | 10/2008 | Tsui et al. |
| 2008/0281222 A1* | 11/2008 | Fukada ................ A61B 5/053 |
| | | 600/547 |
| 2008/0306393 A1 | 12/2008 | Ting et al. |
| 2009/0024044 A1 | 1/2009 | Virtanen et al. |
| 2009/0102296 A1 | 4/2009 | Greene et al. |
| 2009/0182204 A1 | 7/2009 | Semler et al. |
| 2009/0203972 A1 | 8/2009 | Heneghan et al. |
| 2009/0264790 A1* | 10/2009 | Ashida ................ A61B 5/0537 |
| | | 600/547 |
| 2009/0284496 A1* | 11/2009 | Oki ...................... G06F 3/0346 |
| | | 345/174 |
| 2009/0315733 A1 | 12/2009 | Bischoff |
| 2010/0004715 A1 | 1/2010 | Fahey |
| 2010/0016685 A1 | 1/2010 | Muehlsteff et al. |
| 2010/0094147 A1 | 4/2010 | Inan et al. |
| 2010/0210921 A1 | 8/2010 | Park et al. |
| 2010/0262044 A1 | 10/2010 | Siegler |
| 2011/0040352 A1 | 2/2011 | Gerber et al. |
| 2011/0054359 A1 | 3/2011 | Sazonov et al. |
| 2011/0240379 A1 | 10/2011 | Forshaw et al. |
| 2011/0245710 A1 | 10/2011 | Jensen |
| 2011/0310005 A1* | 12/2011 | Chen ..................... G06F 1/3203 |
| | | 345/156 |
| 2012/0003933 A1 | 1/2012 | Baker et al. |
| 2012/0065895 A1 | 3/2012 | Saul |
| 2012/0071792 A1 | 3/2012 | Pfeffer et al. |
| 2012/0123219 A1 | 5/2012 | Georgiev et al. |
| 2012/0165622 A1* | 6/2012 | Rodriguez Ibanez ... A61B 5/00 |
| | | 600/301 |
| 2012/0245476 A1 | 9/2012 | Skeri et al. |
| 2012/0283587 A1 | 11/2012 | Gosh et al. |
| 2012/0302843 A1 | 11/2012 | Otsubo et al. |
| 2012/0318869 A1* | 12/2012 | Edmonds ............ G06K 7/10554 |
| | | 235/462.14 |
| 2013/0056285 A1* | 3/2013 | Meagher ............... G01G 23/02 |
| | | 177/1 |
| 2013/0113506 A1 | 5/2013 | Poupyrev et al. |
| 2013/0289889 A1 | 10/2013 | Yuen et al. |
| 2013/0310700 A1* | 11/2013 | Wiard ................. A61B 5/02125 |
| | | 600/485 |
| 2013/0341104 A1* | 12/2013 | Suzuki .................. G01G 19/44 |
| | | 177/50 |
| 2014/0089836 A1 | 3/2014 | Damani et al. |
| 2014/0094707 A1 | 4/2014 | Farringdon et al. |
| 2014/0121540 A1 | 5/2014 | Raskin |
| 2014/0142396 A1* | 5/2014 | Ricks .................... A61B 5/0537 |
| | | 600/301 |
| 2014/0142437 A1 | 5/2014 | Inan et al. |
| 2014/0172314 A1 | 6/2014 | Baarman |
| 2014/0221849 A1 | 8/2014 | Farringdon et al. |
| 2014/0221850 A1 | 8/2014 | Farringdon et al. |
| 2014/0326517 A1* | 11/2014 | Gomez .................. G01G 19/50 |
| | | 177/1 |
| 2015/0107910 A1 | 4/2015 | Villard et al. |
| 2015/0112209 A1 | 4/2015 | Blaber et al. |
| 2015/0160068 A1 | 6/2015 | Carreel et al. |
| 2015/0168205 A1 | 6/2015 | Lee |
| 2015/0201844 A1 | 7/2015 | Nakagawa |
| 2015/0289802 A1 | 10/2015 | Thomas et al. |
| 2015/0331491 A1* | 11/2015 | Rumreich .............. G06F 3/005 |
| | | 345/173 |
| 2015/0335291 A1 | 11/2015 | Saadi et al. |
| 2015/0338265 A1 | 11/2015 | Carreel et al. |
| 2016/0029905 A1 | 2/2016 | Kovacs |
| 2016/0116326 A1 | 4/2016 | Sharma |
| 2016/0317043 A1 | 11/2016 | Campo et al. |

FOREIGN PATENT DOCUMENTS

| | | |
|---|---|---|
| EP | 1586267 A1 | 10/2005 |
| ES | 2296474 A1 | 4/2008 |
| ES | 2328205 B1 | 8/2010 |
| ES | 2385898 A1 | 8/2012 |
| ES | 2398439 A2 | 3/2013 |
| ES | 2398542 A2 | 3/2013 |
| GB | 2225459 | 5/1990 |
| GB | 2367896 A | 4/2002 |
| JP | 2001198096 | 7/2001 |
| JP | 2001309893 | 11/2001 |
| JP | 2002119488 | 4/2002 |
| JP | 2005-230392 A | 9/2005 |
| JP | 2006212155 | 8/2006 |
| JP | 2007283071 A | 11/2007 |
| JP | 2009050508 A | 3/2009 |
| JP | 2012-191995 A | 10/2012 |
| KR | 0137272 B1 | 4/1998 |
| KR | 20050079235 A | 8/2005 |
| WO | 2005074379 A2 | 8/2005 |
| WO | 2006088280 A1 | 8/2006 |
| WO | 2007103835 A2 | 9/2007 |
| WO | 2008102298 A1 | 8/2008 |
| WO | 2010004502 A1 | 1/2010 |
| WO | WO2010004502 | 1/2010 |
| WO | 2010045455 A1 | 4/2010 |
| WO | 2011075767 A1 | 6/2011 |
| WO | WO2012103296 | 8/2012 |

(56) References Cited

FOREIGN PATENT DOCUMENTS

| | | |
|---|---|---|
| WO | 2013017717 A2 | 2/2013 |
| WO | 2013066642 A1 | 5/2013 |

OTHER PUBLICATIONS

J. Alametsä et al. "Arterial Elasticity Measurements with Ankle Pulse Width Velocity and Ballistocardiography." 2008, ECIFMBE 2008, IFMBE Proceedings 22, p. 1636-1641.

J. Allen. "Photoplethysmography and its application in clinical physiological measurement." Physiol. Meas. 28, 2007, p. R1-R39.

A. Avolio et al. "Role of Pulse Pressure Amplification I Arterial Hpertension: Experts' Opinion and Review of the Data." Hypertension, vol. 54, Aug. 1, 2009, p. 375-383.

J. Blacher et al. "Aortic Pulse Wave Velocity as a Marker of Cardiovascular Risk in Hypertensive Patients," vol. 33, 1999, p. 1111-1117.

Davis, S; B. van den Bogaard et al. "Active standing reduces wave reflection in the presence of increased peripheral resistance in young and old healthy individuals." J Hypertension (4) Apr. 29, 2011, p. 682-689 (ABSTRACT); and B. van den Bogaard. "Chapter 12: Active standing reduces wave reflection in the presence of increased peripheral resistance in young and old healthy individuals." Dissertation, Univ. Amsterdam, 2012, p. 180-193.

G. Kim et al. "Vascular Variation of PTT and the Vascular Characteristic Index According to the Posture Change." In Proceedings of the 2007 International Conference on Convergence Information Technology (ICCIT '07). IEEE Computer Society, Nov. 2007, p. 2426-2425. Abstract Only.

E. Pinheiro et al. "Non-Intrusive Device for Real-Time Circulatory System Assessment with Advanced Signal Processing Capabilities." Measurement Science Review, vol. 10, No. 5, 2010, p. 167-175.

E. Pinheiro et al. "Pulse arrival time and ballistocardiogram application to blood pressure variability estimation." Medical Measurements and Applications, 2009. IEEE Workshop, May 29-30, 2009. Abstract only.

M Safar."Arterial aging—hemodynamic changes and therapeutic options." Nat Rev Cardiol, vol. 7, 207, p. 442-449. Abstract/Introduction Only.

R. Wiard et al. "Estimation of Central Aortic Forces in the Ballistocardiogram under Rest and Exercise Conditions." 31st Annual International Conference of the IEEE EMBS, Sep. 2-6, 2009, p. 2831-2834.

R. Wiard et al. "Automatic detection of motion artifacts in the ballistocardiogram measured on a modified bathroom scale." Med Biol Eng Comput (2011) 49:213-220. Published online Dec. 9, 2010.

B. Williams et al. "Differential Impact of Blood Pressure-Lowering Drugs on Central Aortic Pressure and Clinical Outcomes: Principal Results of the Conduit Artery Function Evaluation (CAFE) Study," Circulation, vol. 113, Feb. 13, 2006, p. 1213-1225.

O.T. Inan, M. Etemadi, R.M. Wiard, L. Giovangrandi, and G. T. A. Kovacs, "Robust Ballistocardiogram Acquisition for Home Monitoring," Phys. Meas., vol. 30, No. 2, pp. 169-185 (2009).

Inan OT, Etemadi M, Paloma A, Giovangrandi L, Kovacs GTA (2009) Non-invasive cardiac output trending during exercise recovery on a bathroom-scale-based ballistocardiograph. Physiol Meas 30:261-274 Abstract/Introduction Only.

Inan OT, Etemadi M, Wiard RM, Kovacs GTA, Giovangrandi L (2009) Novel methods for estimating the ballistocardiogram signal using a simultaneously acquired electrocardiogram. In: 31st annual IEEE engineers in medicine and biology conference. IEEE, Minneapolis, MN Abstract/Introduction Only.

Inan OT, Kovacs GTA, Giovangrandi L (2010) Evaluating the lower-body electromyogram signal acquired from the feet as a noise reference for standing ballistocardiogram measurements. IEEE Trans Inf Technol Biomed 14:1188-1196 Abstract/Introduction Only.

DeLoach SS, Twonsend RR, "Vascular Stiffness: Its Measurement and Significance for Epidemiologic and Outcome Studies", Clin J Am Soc Nephrol, 3: 184-192, 2008. Abstract/Introduction Only.

Webster's Ninth New Collegiate Dictionary, Meriam-Webster Inc., 1990, p. 1152.

Alan Fang et al., "Using a Geophone for Vibration Cancellation in a STM," abstract, Bulletin of the American Physical Society, 2008 APS Mar. Meeting, vol. 53, No. 2, Mar. 10, 2008.

de Viries, S. O. et al., "Prediction of the Left Ventricular Mass from the Electrogram in Systemic Hypertension," American Journal of Cardiology, 1996 May 1;777(11):974-8. (Abstract Only).

A.Akhbardeh, M. Koivuluoma, T. Koivistoinen and A. Varri, "Ballistocardiogram Diagnosis Using Neural Networks and Shift-Invariant Daubechies Wavelet Transform," Researchers at Institute of Signal Processing, Tampere University ofTechnololgy, Tampere 33101, Finland.

O. Inan, et al. "Evaluating the Foot Electromyogram Signal as a Noise Reference for a Bathroom Scale Ballistocardiogram Recorder," Stanford University, Department of EE, Department of Bioengineering.

0. Inan and G. Kovacs, "An 11 µW, Two-Electrode Transimpedance Biosignal Amplifier with Active Current Feedback Stabilization," IEEE Transactions on Biomedical Circuits and Systems (2009).

0. Inan, M. Etemadi, B. Widrow and G. Kovacs, "Adaptive cancellation of floor vibrations in standing ballistocardiogram measurements using a seismic sensor as a noise reference," IEEE (2009).

R. F. Yazicioglu, P. Merken, R. Puers and C. Van Hoof, "A 60 µW 60 nV/..JHz Readout Front-End for Portable Biopotential Acquisition Systems," IEEE Journ. Of Solid-State Circuits, vol. 42, No. 5 (May 2007).

W. Rosamond et al., "Heart Disease and Stroke Statistics—2007 Update: A Report from the American Heart Association Statistics Committee and Stroke Statistics Subcommittee," Circ., v. 115, pp. 69-171 (2007).

R. R. Harrison, "A Versatile Integrated Circuit for the Acquisition of Biopotentials," IEEE CICC, pp. 115-122 (2007).

T. Denison, K. Consoer, W. Santa, A.-T. Avestruz, J. Cooley, and A. Kelly, "A 2µW JOO nV/rtHz, Chopper-Stabilized Instrumentation Amplifier for Chronic Measurement of Neural Field Potentials," IEEE Jour. Solid-State Circuits, v. 42, No. 12, DD. 2934-2945 (2007).

A.Akhbardeh, S. Junnila, M. Koivuluoma, T. Koivistoinen, V. Turjanmaa, T. Koobi, and A. Viirri, "Towards a heart disease diagnosing system based on force sensitive chair's measurement, biorthogonal wavelets and neural networks," ScienceDirect, Engineering Applications for Artificial Intelligence, pp. 1-10 (2006).

D. Corrado, C. Basso, A. Pavei, P. Michieli, M. Schiavon, and G. Thiene, "Trends in Sudden Cardiovascular Death in Young Competitive Athletes After Implementation of a Preparticipation Screening Program," JAMA, vol. 296, No. 13, pp. 1593-1601 (Oct. 4, 2006).

C.N. Chien and F.S. Jaw, "Miniature ultra-low-power biopotential amplifier for potable [sic} applications," Biomedical Engineering-Applications, Basis & Communications, vol. 17, No. 2, pp. 11-49 (Apr. 2005).

C.W. Mundt, K.N. Montgomery, U.E. Udoh, V.N. Barker, G.C. Thonier, A.M. Tellier, R.D. Ricks, R.B. Darling, Y.D. Cagle, N.A. Cabrol, S.J. Ruoss, J.L. Swain, J.W. Hines, and G.T.A. Kovacs, "A Multiparameter Wearable Physiologic Monitoring System for Space and Terrestrial Applications," IEEE Trans. Inform. Tech. in Biomed., vol. 9, No. 3, pp. 382-391 (Sep. 2005).

M. Shojaei-Baghini, R.K. Lal, and D.K. Sharma, "A Low-Power and Compact Analog CMOS Processing Chip for Portable ECG Recorders," Proc. IEEE A.S.S.C.C., DD. 473-476 (2005).

J. Alametsii, A. Viirri, M. Koivuluoma, and L. Barna, "The Potential of EMFi Sensors in Heart Activity Monitoring," 2nd OpenECG Workshop "Integration of the ECG into the EHR & Interoperability of ECG Device Systems," Apr. 1-3, 2004 Berlin, Germany.

E. Company-Bosch and E. Hartmann, "ECG Front-End Design is Simplified with MicroConverter," Analog Dialogue, 37-11, pp. 1-5 (Nov. 2003).

(56) References Cited

OTHER PUBLICATIONS

D.M. Linton and u. Giion, "Advances in noninvasive cardiac output monitoring," Annals of cardiac Anaesthesia, vol. 5, pp. 141-148 (2002).
M. Watanabe, J. Marine, R. Sheldon, and 1\1. Josephson, "Effects of Ventricular Premature Stimulus Coupling Interval on Blood Pressure and Heart Rate Turbulence," Circ., vol. 106, pp. 325-330 (2002).
K. Lu, J. W. Clark, Jr., F. H. Ghorbel, D. L. Ware, and A. Bidani, "A human cardiopulmonary system model applied to the analysis of the Valsalva maneuver," Am. J Physiol. Heart Circ. Physiol., vol. 281, pp. H2661-H2679 (2001).
J. Rapoport, D. Teres, J. Steingrub, T. Higgins, W. McGee, and S. Lemeshow, "Patient characteristics and ICU organizational factors that influence frequency of pulmonary artery catheterization," JAMA, vol. 283, No. 19, pp. 2559-2567 (2000).
B.D. Johnson, K.C. Beck, D.N. Proctor, J. Miller, N.M. Dietz, and M.J. Joyner, "Cardiac output during exercise by the open circuit acetylene washin method: comparison with direct Fick," J. Appl Physiol, vol. 88, pp. 1650-1658 (2000).
W. Klimesch, "EEG alpha and theta oscillations reflect cognitive and memory performance: a review and analysis," Brain Research Reviews, vol. 29, DD. 169-195 (1999).
D. Corrado, C. Basso, M. Schiavon, and G. Thiene, "Screening for Hypertrophic Cardiomyopathy in Young Athletes," NEJM, vol. 339, pp. 364-369 (Aug. 6, 1998).
A.C. MettingVanRijn, A. Peper and C.A. Grimbergen, "Amplifiers for bioelectric events: a design with a minimal number of parts," Med. & Biol. Eng. & Comput., vol. 32, DD. 305-310 (1994).
R. Moore, R. Sansores, V. Guimond, and R. Abboud, "Evaluation of cardiac output by thoracic electrical bioimpedance during exercise in normal subjects," American College of Chest Physicans, vol. 102, DD. 448-455 (1992).
J. Christie, L.M. Sheldahl, F.E. Tristani, K.B. Sagar, M.J. Ptacin, and S. Wann, "Determination of stroke volume and cardiac output during exercise: comparison of two-dimensional and Doppler echocardiography, Fick oximetry, and thermodilution," Circ., vol. 76, DD. 539-547 (1987).
H. Benjelloun, R. Itti, L. Philippe, J.M. Lorgeron and M. Brochier, "Beat-to-Beat Assessment of Left Ventricular Ejection in Atrial Fibrillation," European Journal Nuclear Medicine, vol. 8, pp. 206-210 (1983).
S. Grimnes, "Impedance measurement of individual skin surface electrodes," Med. & Biol. Eng. & Comput., vol. 21, DD. 750-755 (1983).
Y. Miyamoto, M. Takahashi, T. Tamura, T. Nakamura, T. Hiura, and M. Mikami, "Continuous determination of cardiac output during exercise by the use of impedance plethysmogrphy," Med. Biol. Eng. Comp., vol. 19, DD. 638-644, (1981).
R.P. Lewis S.E. Rittogers, W.F. Froester, and H. Boudoulas, "A critical review of the systolic time intervals," Circulation, vol. 56, DD. 146-158 (1977).
European Patent Office, Third Examination Report dated Nov. 26, 2014 for EPO Patent Application No. 07757854.0. which claims priority from PCT Application No. PCT/US2007/063244.
China State Intellectual Property Office, Office Action dated Oct. 13, 2010 for CN Patent Application No. 200780015788.1.
Japan Patent Office, Notice of Reasons for Rejection dispatched Mar. 6, 2012 for JPO Patent Application No. P2008-558484. which claims priority from PCT Application No. PCT/US2007/063244; Reference 1 cited in the Notice of Reaons for Rejection corresponds to US 08/555,546, issued as U.S. Pat. No. 5701894, Cherry et al., which is cited above; Reference 2, US 20030050537, Wessel, is cited above.
European Patent Office, Extended European Search Report dated Feb. 12, 2010 for EPO Application No. 07757854.0.
International Search Report and Written Opinion of the International Searching Authority for PCT International App. No. PCT/US07/63244.

Discera, "Shrinking Wireless Architectures", available for download from www.discera.com prior to Mar. 3, 2006.
GeTeMed GmbH, "Baby Monitoring System Vitaguard VG3000", Teltow, Germany, 1997-1999.
Atmel, "Microcontroller with 16 K Bytes In-System Programmable Flash", Atmel Atmega, document contains notation ACR 06/05.
Kaminska, "Wireless Wearable Biomonitors for Lifetime Wellness Optimization", Proceedings of the 3rd Annual International IEEE EMBS Special Topic Conference on Microtechnologies in Medicine and Biology, Kahuku, Oahu, Hawaii, May 2005. Abstract Only.
NorthEast Monitoring Inc., "Holter LX Pro Software—Operator's Manual", NorthEast Monitoring Inc. Two Clock Tower Suite 360 Maynard Massachusetts 01754, Apr. 2003.
Nguyen et al., "Transceiver Front-End Architectures Using Vibrating Micromechanical Signal Processors", Dig. of Papers, Topical Meeting on Silicon Monolithic Integrated Circuits in RF Systems: Sep. 23-32, 2001 4.
ANSI/AAMI, EC11:1991/(R) 2001, Diagnostic Electrogardiographic Devices, 2000.
ANSI/MM I, EC38: 1998, Ambulatory Electrocardiographs, 1999.
Nguyen et al., "Frequency-Selective MEMS for Miniaturized Low-Power Communication Devices", IEEE Trans. Microwave Theory Tech 47(8):1486-1503, Aug. 1999.
Nguyen et al., "An Integrated CMOS Micromechanical Resonator High-Q Oscillator", IEEE Journal of Solid-State Circuits 34(4), Apr. 1999.
Nguyen et al., "Micromachined Devices for Wireless Communications," Proc. IEEE 86(8):1756-1768, Aug. 1998.
Kovacs, "Micromachined Transducers-Sourcebook", McGraw-Hill, New York, New York, 1998 944 page book Book Description provided.
Desel et al., "A CMOS Nine Channel ECG Measurement IC", ASIC 1996 2nd International Conference: 115-118, Oct. 1996 Abstract Only.
Fraunhofer, "Medical Technolology", http://www.iis.fraunhofer.de/en/ff/med.html Dec. 26, 2005.
Toumaz "Technology", Nov. 8, 2005.
Kaminiski, "Wearable Biomonitors With Wireless Network Communication" draft of paper published in Proceedings of the 3rd Annual International IEEE EMBS Special Topic Conference on Microtechnologies in Medicine and Biology, Kahuku, Oahu, Hawaii, May 2005.
Novosense AB, "Company", Apr. 4, 2005.
IMEC, "Sensor Electronics", Mar. 31, 2005.
Novosense, AB, "Technology", available for download at http://www.novosense.se/technology.html Aug. 5, 2015.
Miromico AG, "Sample Projects", available for dowolcad at http://www.miromico.ch/index.php?sec-ad.sa&lang=2, page includes notice of Copyright 2005 Miromico.
Mori, Narumi, et al. "Clinical assessment of a new method for pacing pulse detection using a hybrid circuit in digital Holter monitoring." Japanese circulation journal 64.8 (2000): 583-589.
Pyron, "Pyron Introduces ECG ASIC Monitoring Subsystem", Electronic News, Nov. 29, 1999.
Nguyen, Clark T-C., and Roger T. Howe. "An integrated CMOS micromechanical resonator high-Q oscillator." Solid-State Circuits, IEEE Journal of 34.4 (1999): 440-455.
Grossbach, Wolfgang. "Measuring the ECG Signal with a Mixed Analog-Digital Application-Specific IC." Hewlett-Packard Journal 42.4 (1991): 21-24. Abstract Only.
I. Starr and F.C. Wood, "Twenty-Year Studies with the Ballistocardiograph: The Relation Between the Amplitude of the First Record of 'Healthy' Adults and Eventual Mortality and Morbidity from Heart Disease," Circulation, vol. 36, DD. 714-732 (1961).
D.C. Deuchar, S.A. Talbot, and W.R. Scarborough, "Some Observations on the Relation of the High-Frequency Bed Ballistocardiogram to that Obtained from an Aperiodic Bed," Circulation, vol. 11, pp. 228-239 (1955).
H. Mandelbaum and R.A. Mandelbaum, "Studies Utilizing the Portable Electromagnetic Ballistocardiograph: IV. The Clinical Significance of Serial Ballistocardiograms Following Acute Myocardial Infarction," Circulation, vol. 7, pp. 910-9165 (1953).

(56) References Cited

OTHER PUBLICATIONS

R.S. Guber, M. Rodstein and H.E. Ungerleider, "Ballistocardiograph: An Appraisal of Technic, Physiological Principles, and Clinic Value," Circulation, vol. 7, DD. 268-286 (1953).

M.B. Rappaport, H.B. Sprague, and W.B. Thompson, "Ballistocardiography: I. Physical Considerations," Circulation, vol. 7, pp. 229-246 (1953).

0. Tannenbaum, J. Schack and H. Vesell, "Relationship between Ballistocardiographic Forces and Certain Events in the Cardiac Cycle," Circulation, vol. 6, DD. 586-592 (1952).

T.E. Satterthwaite, "Cardiovascular Diseases: Recent Advances in Their Anatomy, Physiology, Pathology, Diagnosis and Treatment," Lemcke and Beuschner, New York, NY (1913).

J.W. Gordon, "On Certain Molar Movements of the Human Body Produced by the Circulation of the Blood," J. of Anat. and Phys., vol. 11, DD. 533-536 (1877).

Gonzalez, et al. "Deteccion of las frecuencias 1-9 cardiaca and respitatoria mediante una bascu the electronica" In: IFMBE Proceedings. vol. 18, pp. 448-451, 2008. Springer-Verlag Berlin Heidelberg. Abstract Only.

Gomez-Clapers J. et al. "Pulse arrival time estimation from the impedance plethysmogram obtained with a handheld device", 33rd Annual International Conference of the IEEE EMBS, Boston, USA, Mar. 8-Mar. 9, 2011, pp. 516-519. Abstract only.

HeartForce Medical Inc. "definitions and Terminologies: History of Seismocardiology." www.heartforcemedical.com 4 pages.

Shin et al., "Non-constrained monitoring of systolic blood pressure on a seighing scale", Physiological Measurement, vol. 30, No. 7, pp. 679-693, 2009 Abstract Only.

Pliquett et al., "Front end with offset-free symmetrical current source optimized for time domain impedance spectroscopy", Physiological Measurement, vol. 32, No. 7, 2011.I Abstract Only.

Earbud Ballistocardiogram: HeadSense Israel: http://head-sense-med.com/ http://www.medgadget.com/2013/07/headsense-intracranial-pressure-monitoring-earbuds.html.

Bifrostec & The Kaiteki Institute http://www.psfk.com/2013/11/earbud-heart-monitor.html#IzIKRT.

http://www.endgadget.com/2014/01/06/intel-smart-earbuds/.

Mitchell et al., "Arterial Stiffness and Cardiovascular Events The Framingham Heart Study" . Circulation 2010, 121: 505-11.

Blacher et al., "Impact of Aortic Stiffness on Survival in End-Stage Renal Disease" Circulation, 1999: 99.

Blacher et al., "Arterial Calcifications, Arterial Stiffness, and Cardiovascular Risk in End Stage Renal Disease" Hypertension. 38: 938-942 (2001).

Di Micco, et al., "Daily dialysis reduces pulse wave velocity in chronic hemodialysis patients". Hypertension Research. vol. 35, 2012.

Laurent S et al., "Expert consensus document on arterial stiffness: methodological issues and clinical applications", European Heart Journal (2006) 27, 2588-2605.

Boutouyrie P et al., "Assessment of arterial stiffness for clinical and epidemiological studies: methodological considerations for validation and entry into the European Renal and Cardiovascular Medicine registry", Nephrol Dial Transplant (2014) 29: 232-239.

Stewart A D. et al., "Acute Reduction of Blood Pressure by Nitroglycerin Does Not Normalize Large Artery Stiffness in Essential Hypertension", Hypertension 2006, 48: 404-410.

Stewart A D. et al., "Effects of Inhibition of Basal Nitric Oxide Synthesis on Carotid-Femoral Pulse Wave Velocity and Augmentation Index in Humans", Hypertension 2003, 42: 915-918.

Avolio A P., et al., "Effects of aging on changing arterial compliance and left ventricular load in a northern Chinese urban community", Circulation 68, No. 1, 50-58, 1983.

Wilkinson, I B. et al., "Artery Society guidelines for validation of non-invasive haemodynamic measurement devices: Part 1, arterial pulse wave velocity" Artery Research (2010) 4, 34-40.

Avolio A P., et al. "Improved Arterial Distensibility in Normotensive Subjuects on a Low Salt Diet", Arteriosclerosis 6: 166-169, 1986.

Balkestein E J., et al., "The effect of weight loss with or without exercise training on large artery compliance in healthy obese men", J. Hypertens 1999, 17: 1831-1835.

Laurent S, et al., "Mesure de la Rigidite Arterielle" Dec. 2013.

Wiard, Richard M., et al. "Preliminary results from standing ballistocardiography measurements in microgravity." 2013 35th Annual International Conference of the IEEE Engineering in Medicine and Biology Society (EMBC). IEEE, 2013. Abstract only.

Inan, Omer T., et al. "Noninvasive measurement of physiological signals on a modified home bathroom scale." IEEE Transactions on Biomedical Engineering 59.8 (2012): 2137-2143. Abstract only.

Giovangrandi, Laurent, et al. "Preliminary results from BCG and ECG measurements in the heart failure clinic." 2012 Annual International Conference of the IEEE Engineering in Medicine and Biology Society. IEEE, 2012. Abstract only.

Park, Dookun, Omer T. Inan, and Laurent Giovangrandi. "A combined heartbeat detector based on individual BCG and IPG heartbeat detectors." 2012 Annual International Conference of the IEEE Engineering in Medicine and Biology Society. IEEE, 2012. Abstract only.

Etemadi, Mozziyar, et al. "Rapid assessment of cardiac contractility on a home bathroom scale." IEEE transactions on information technology in biomedicine 15.6 (2011): 864-869. Abstract only.

Giovangrandi, L., et al. "Ballistocardiography—a method worth revisiting." Conference proceedings: . . . Annual International Conference of the IEEE Engineering in Medicine and Biology Society. IEEE Engineering in Medicine and Biology Society. Annual Conference. vol. 2011 . NIH Public Access, 2010.

Inan, Omer T., et al. "Multi-signal electromechanical cardiovascular monitoring on a modified home bathroom scale." 2011 Annual International Conference of the IEEE Engineering in Medicine and Biology Society. IEEE, 2011. Abstract only.

Wiard, R. M., et al. "Estimation of central aortic forces in the ballistocardiogram under rest and exercise conditions." Conference proceedings: . . . Annual International Conference of the IEEE Engineering in Medicine and Biology Society. IEEE Engineering in Medicine and Biology Society. Annual Conference. vol. 2009. NIH Public Access, 2008.

Etemadi, Mozziyar, et al. "Non-invasive assessment of cardiac contractility on a weighing scale." 2009 Annual International Conference of the IEEE Engineering in Medicine and Biology Society. IEEE, 2009. Abstract only.

Inan, Omer T., et al. "Non-invasive measurement of valsalva-induced hemodynamic changes on a bathroom scale ballistocardiograph." 2008 30th Annual International Conference of the IEEE Engineering in Medicine and Biology Society. IEEE, 2008. Abstract only.

Inan, Omer T., et al. "Unobtrusive Monitoring of Cardiovascular Health at Home Using a Modified Weighing Scale." 6th European Conference of the International Federation for Medical and Biological Engineering. Springer International Publishing, 2015. Abstract only.

McCall, Corey, et al. "Standing ballistocardiography measurements in microgravity." 2014 36th Annual International Conference of the IEEE Engineering in Medicine and Biology Society. IEEE, 2014. Abstract only.

Inan, Omer Tolga. Novel technologies for cardiovascular monitoring using ballistocardiography and electrocardiography. vol. 70. No. 10. 2009. Copy unavailable.

Wiard, Richard Matthew. Validation of Non-invasive Standing Arterial Stiffness Measurements Using Ballistocardriography and Photoplethysmography. 2012. Abstract only.

EPO Supplementary European Search Report dated Feb. 8, 2018, for European Patent Application No. 15808117.6 (3 pages).

\* cited by examiner

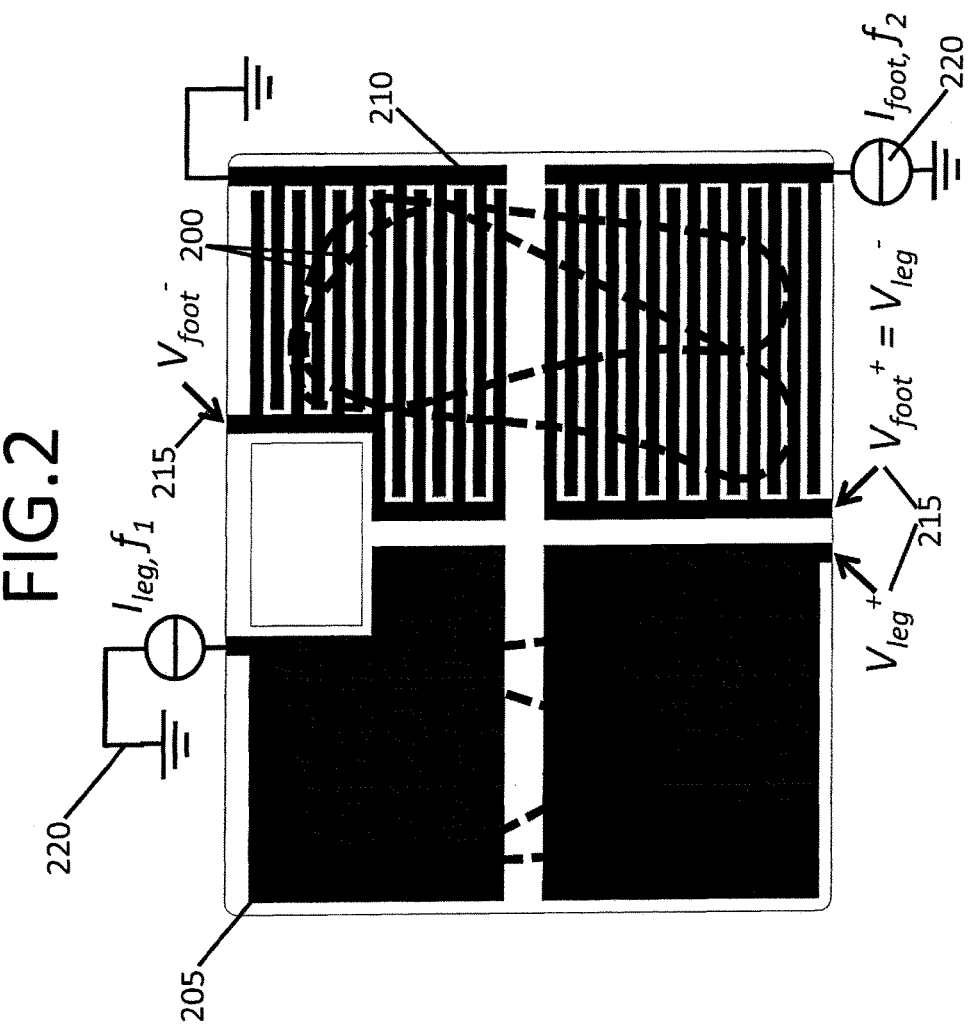

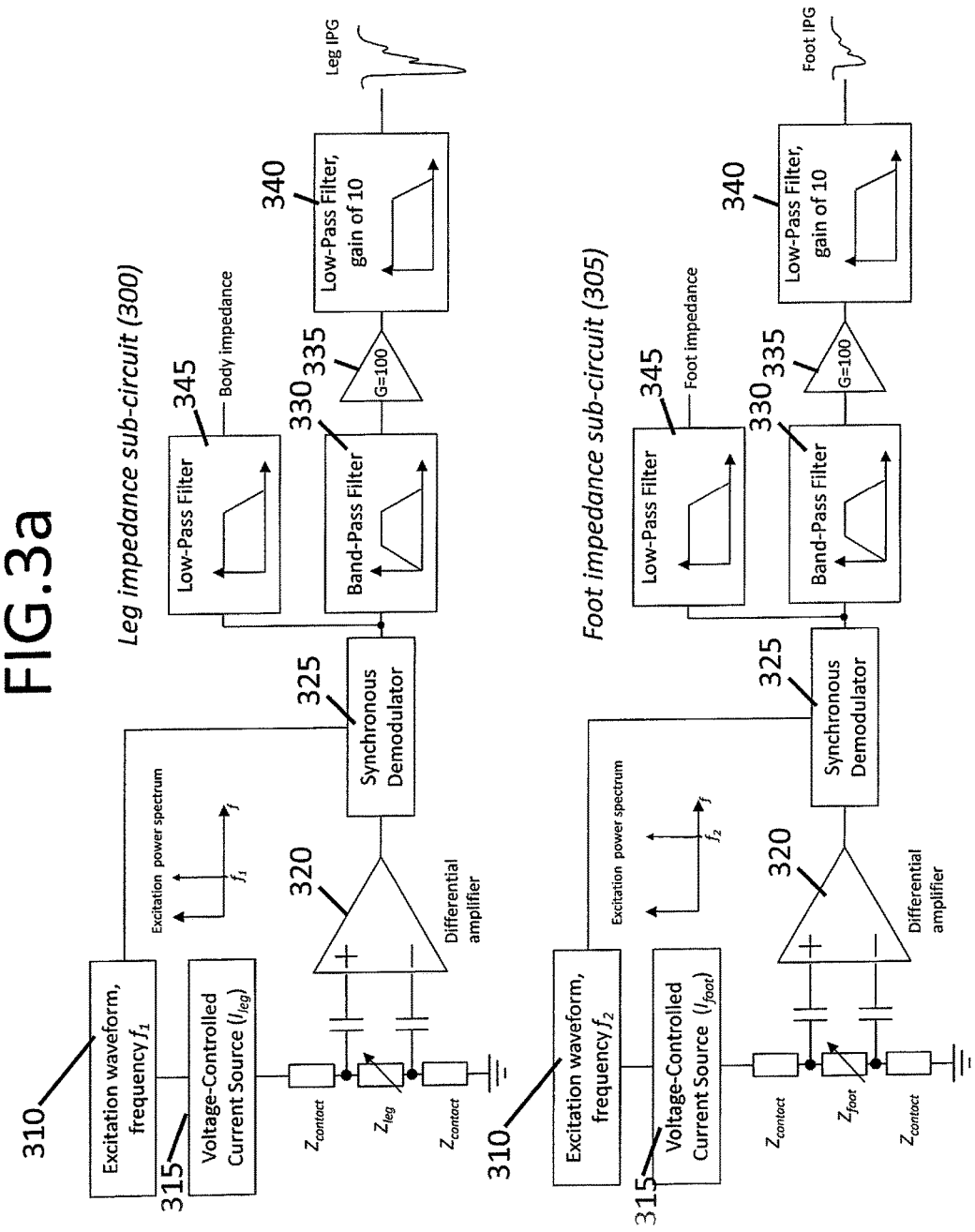

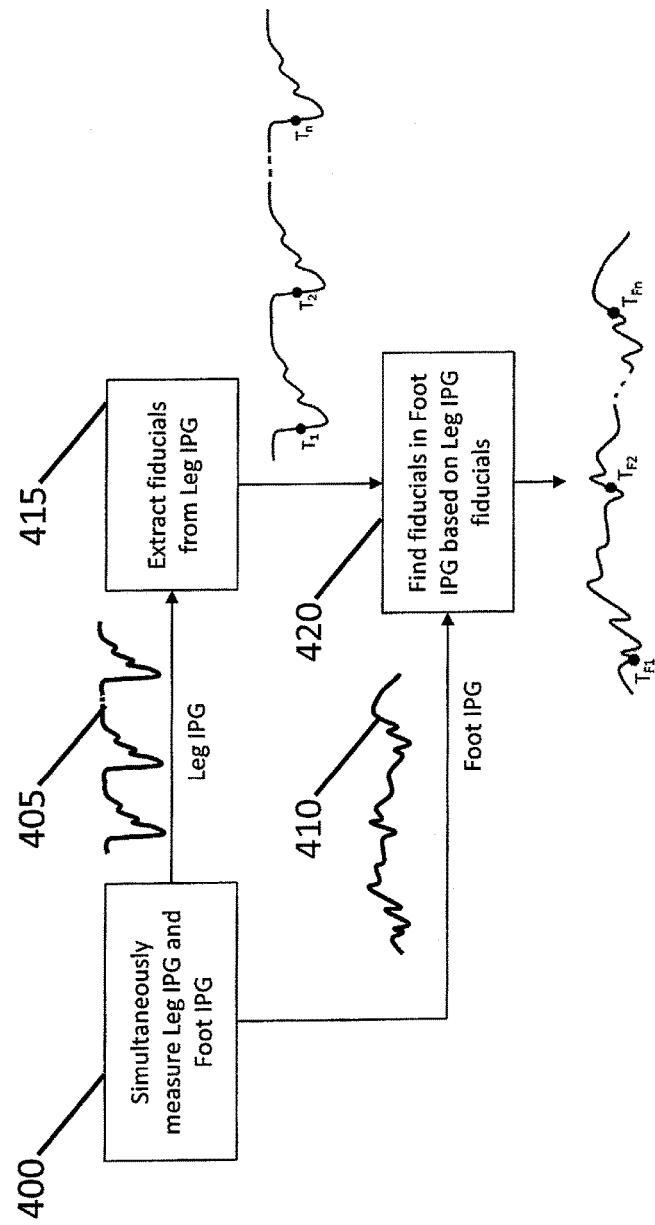

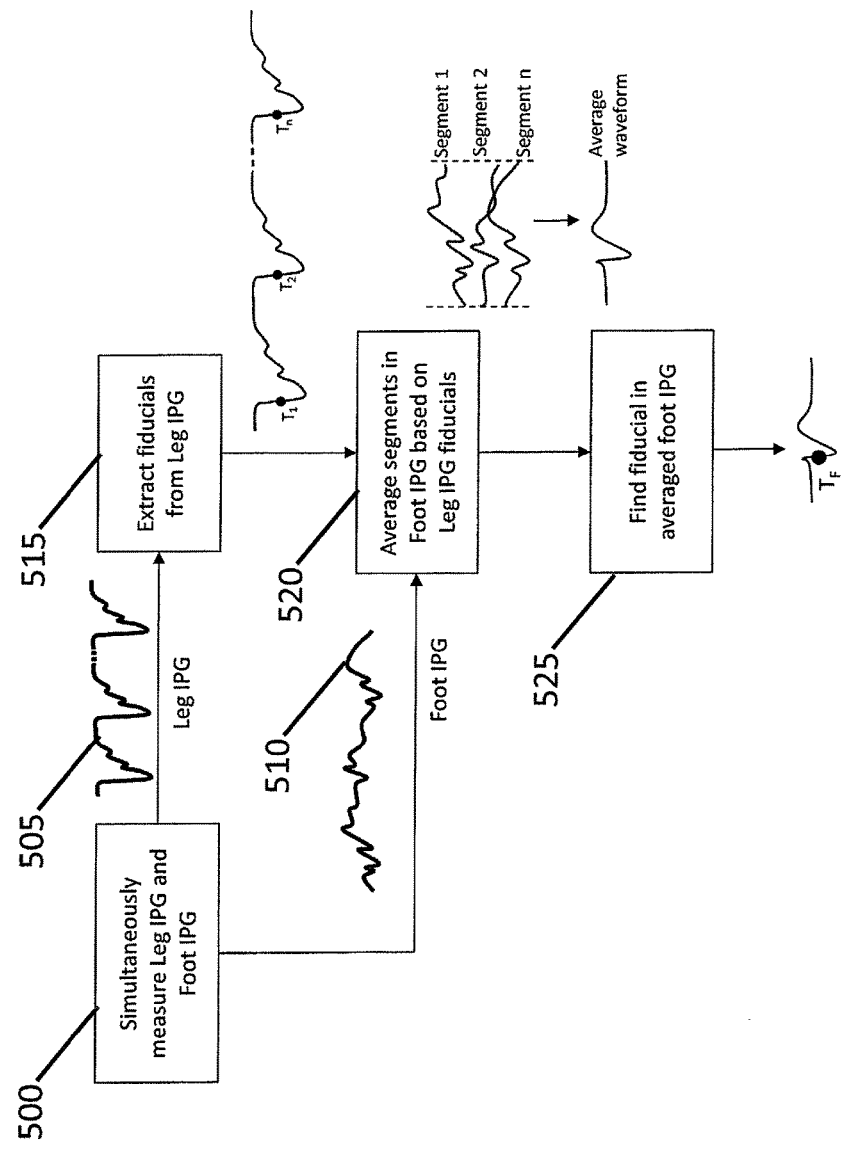

Example of high-quality Foot IPG signals (Vertical units are arbitrary)

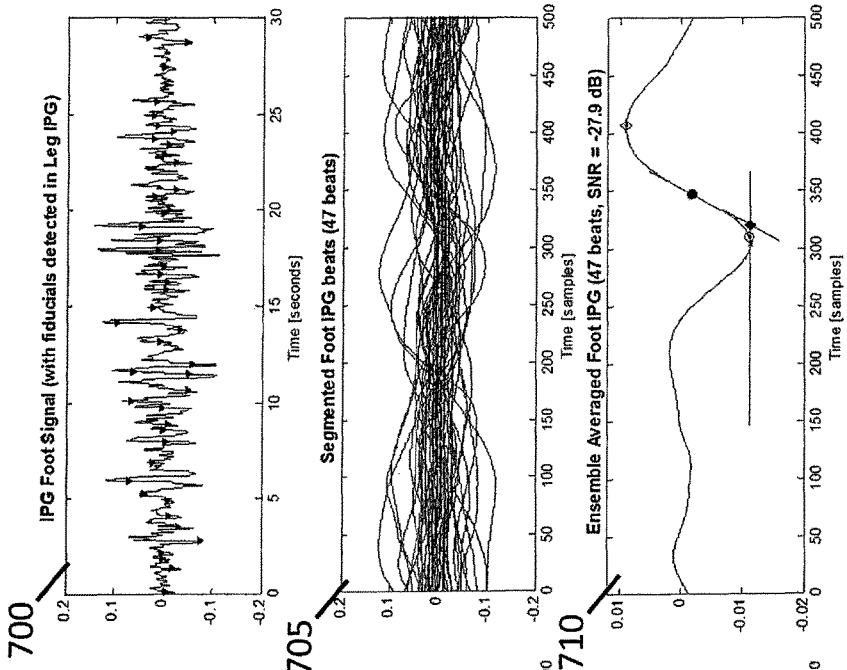
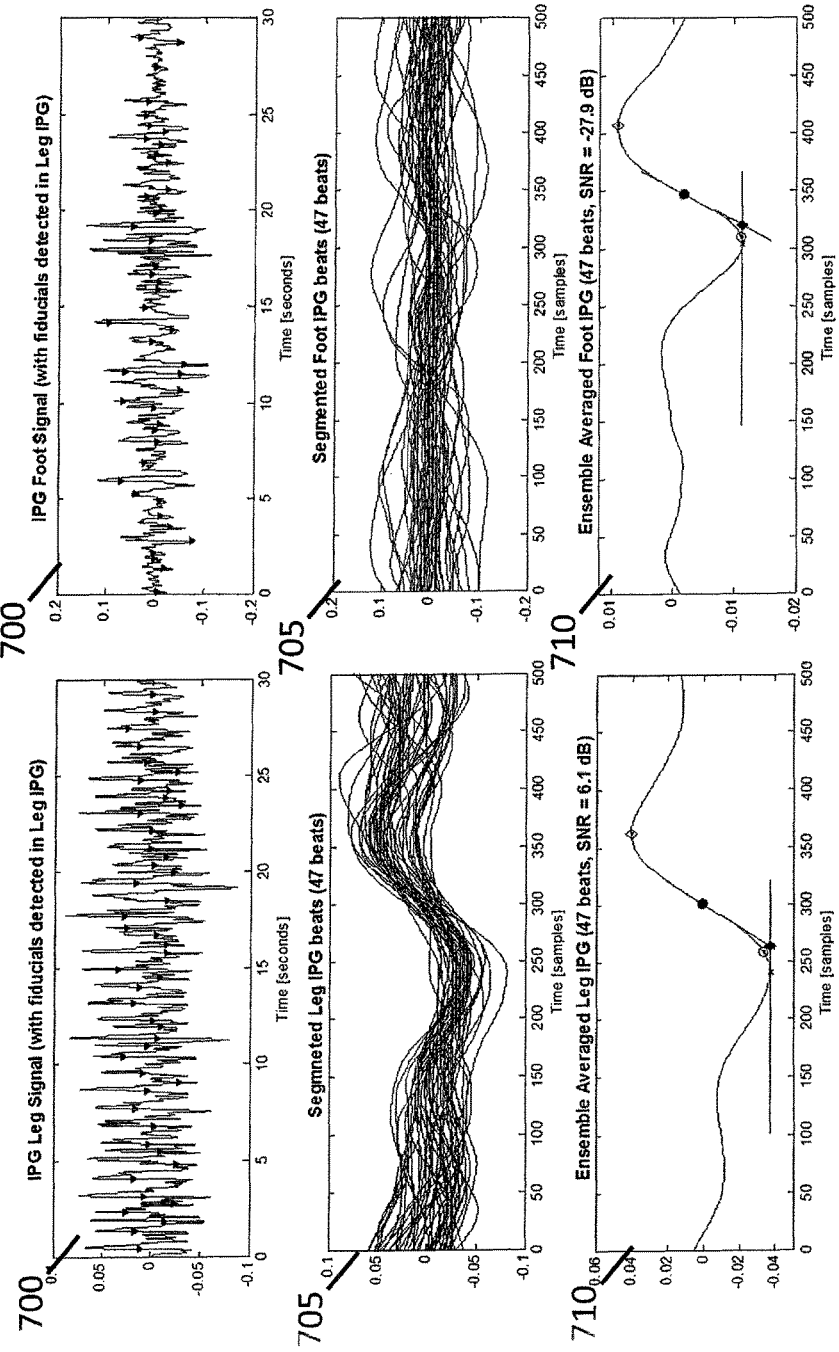
FIG. 7a
FIG. 7b
Example of low-quality Foot IPG signals
(Vertical units are arbitrary)

Metric of Leg IPG triggering robustness, based on various heart rates in 61 subjects for a standardized 30-second recording interval

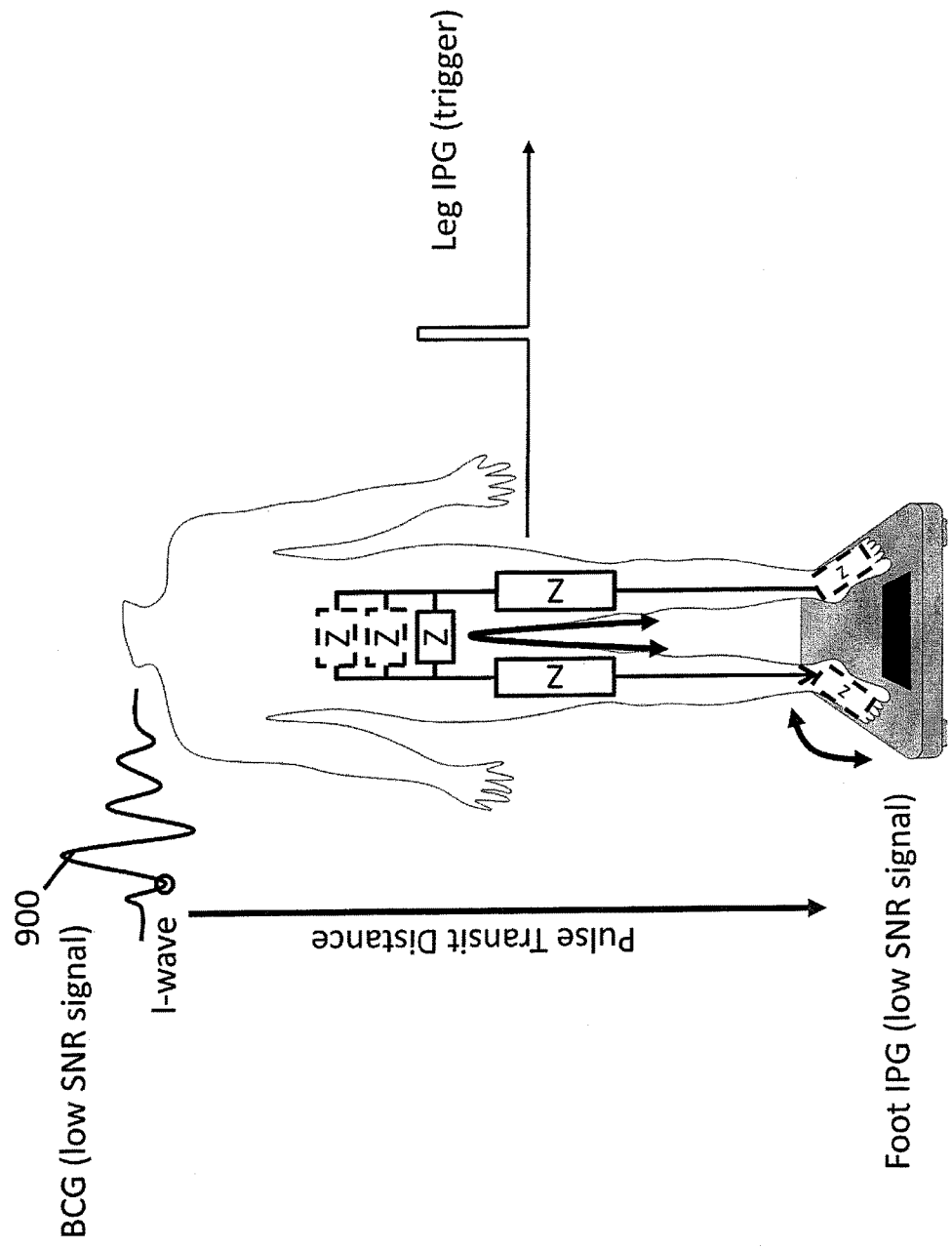

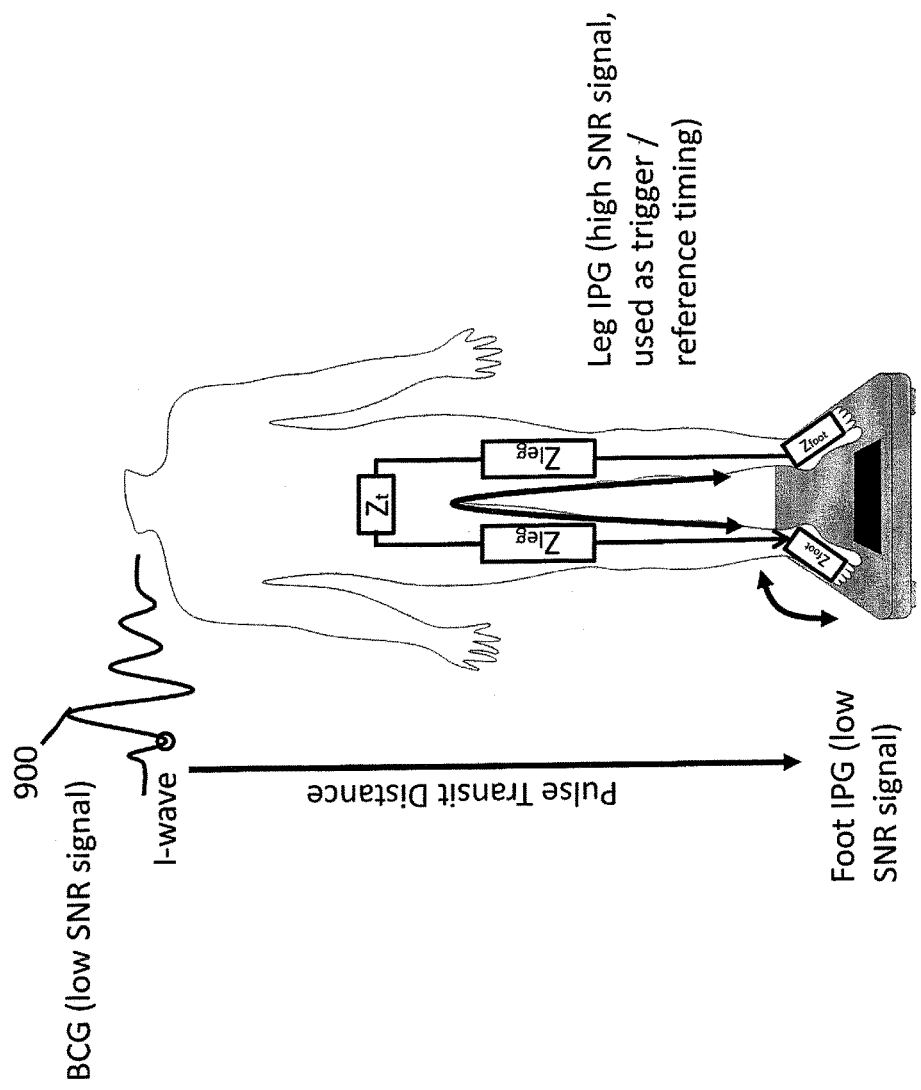

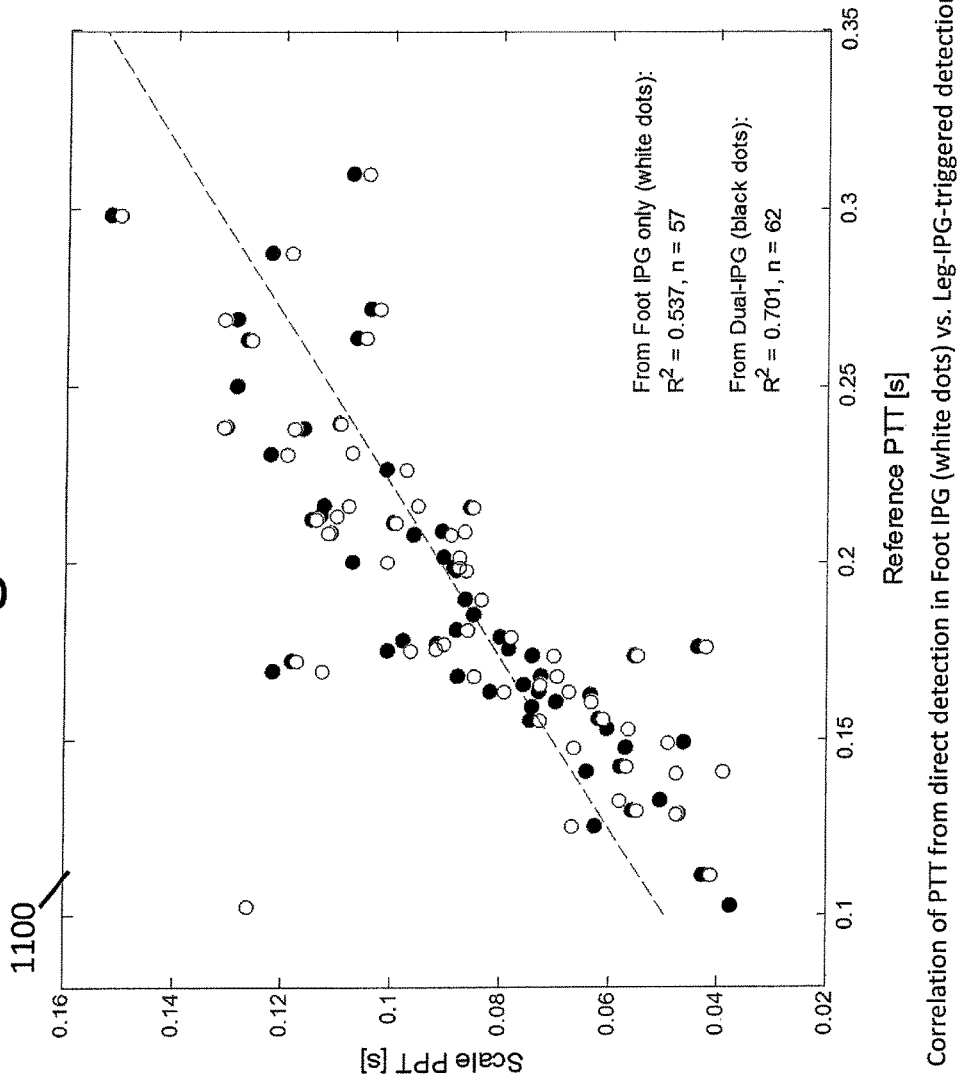

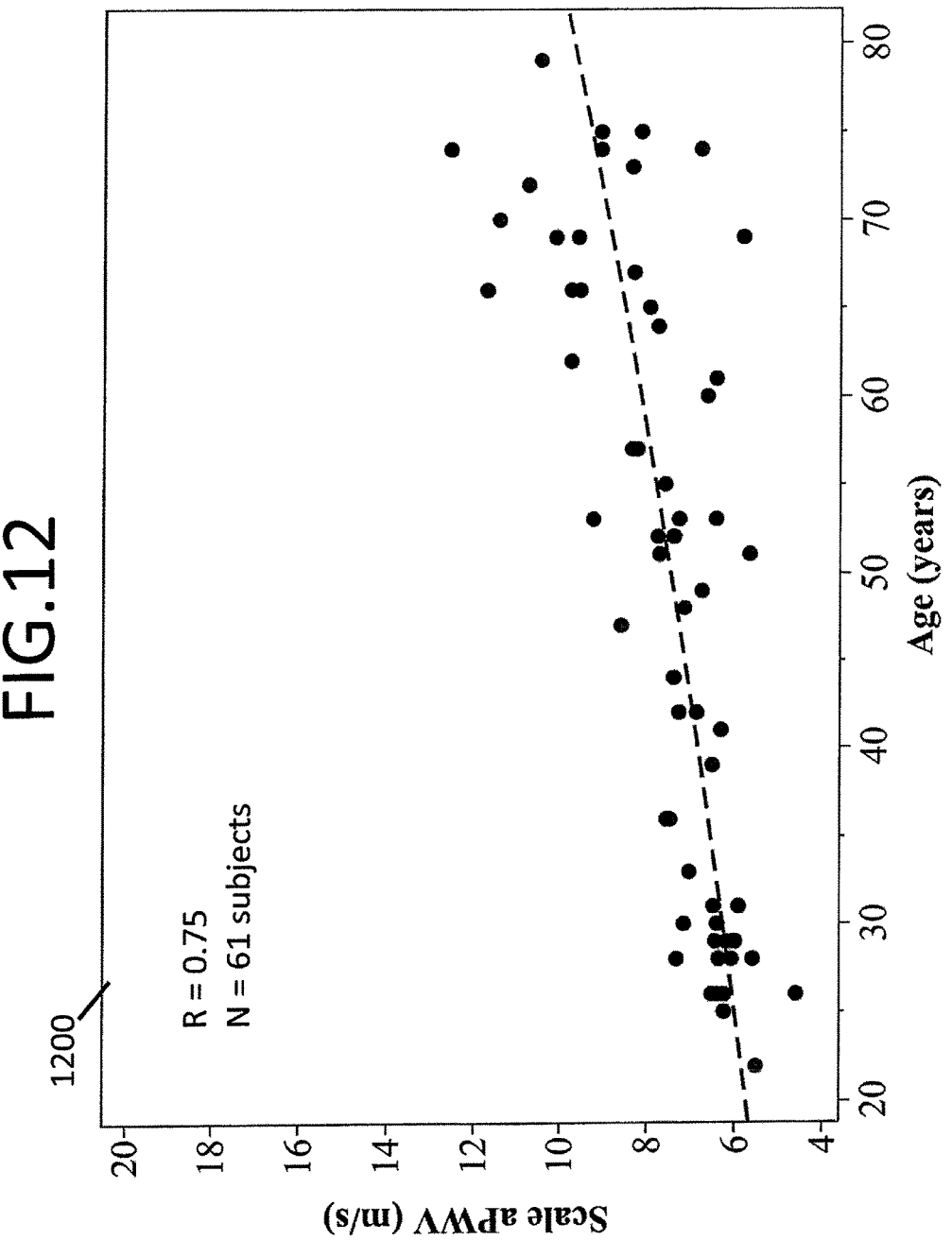

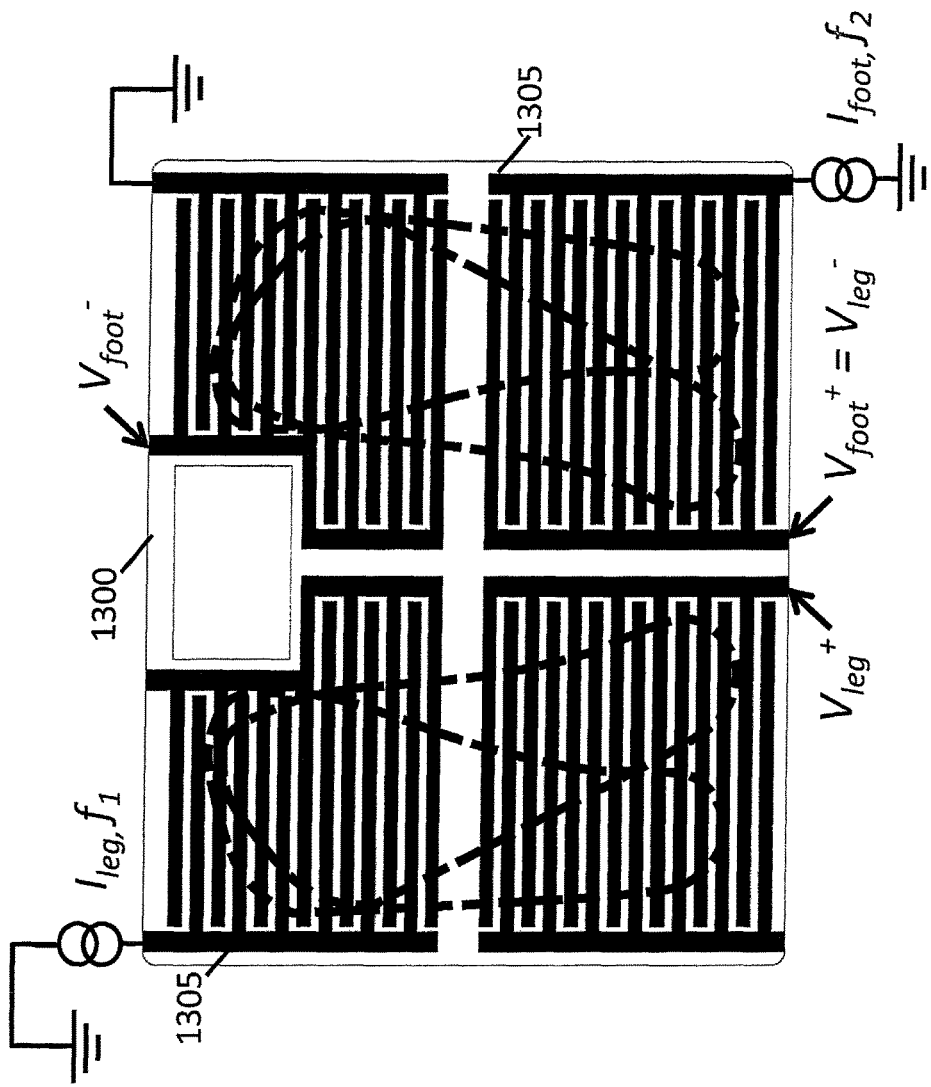

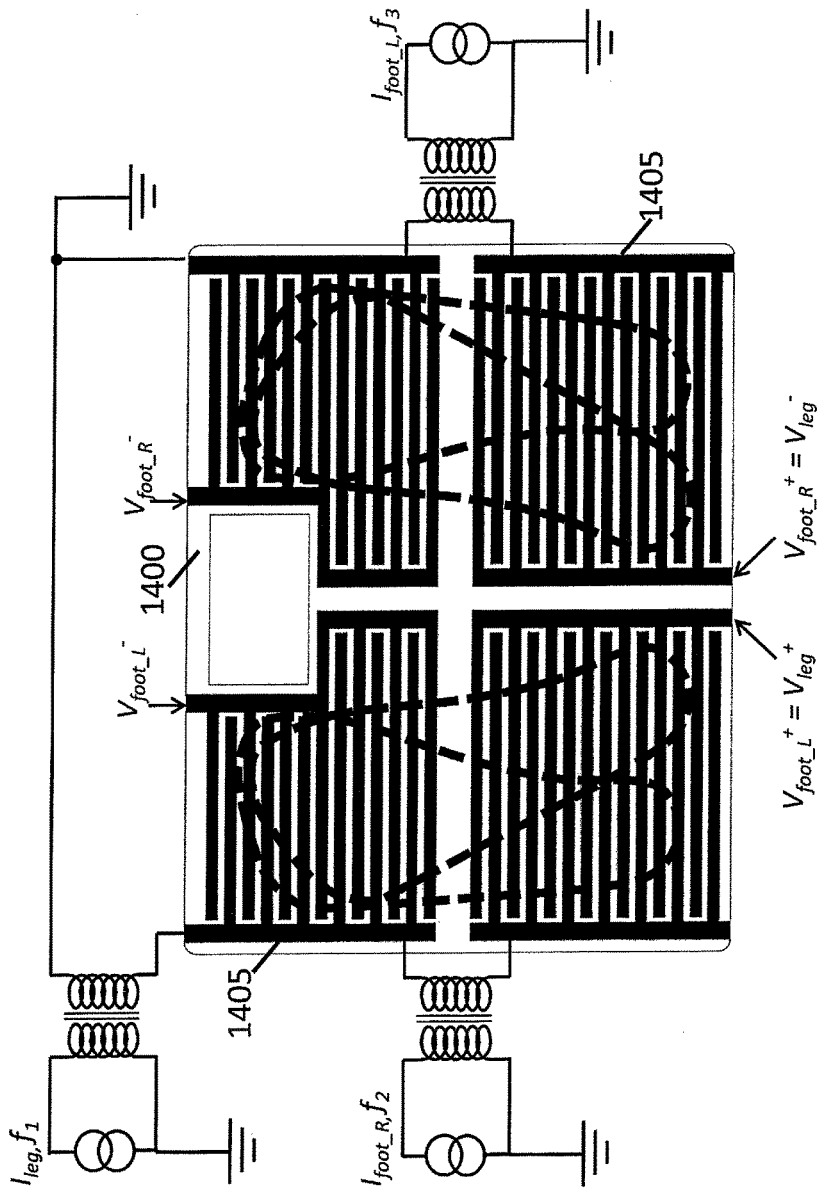

FIG.15
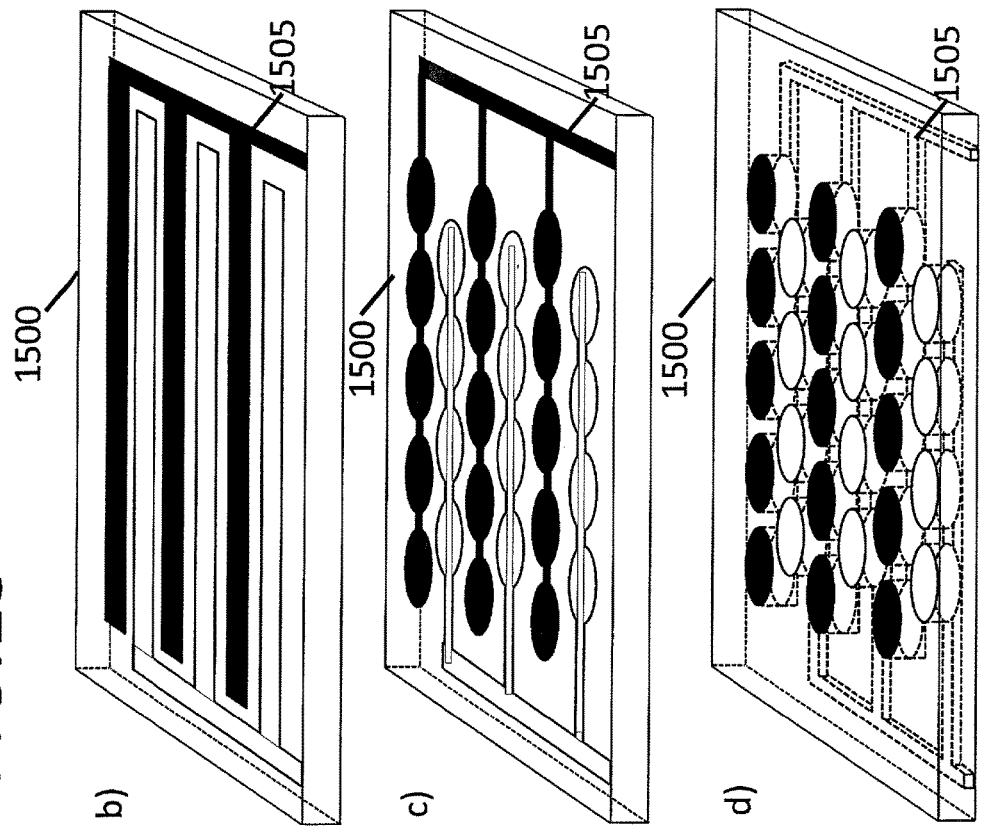
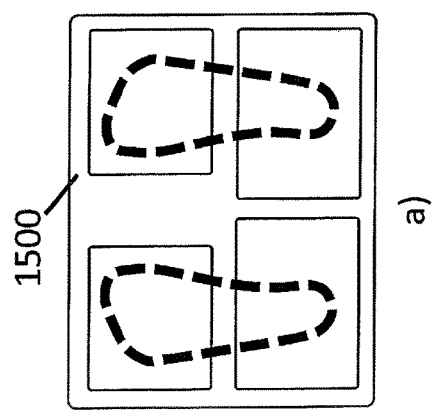

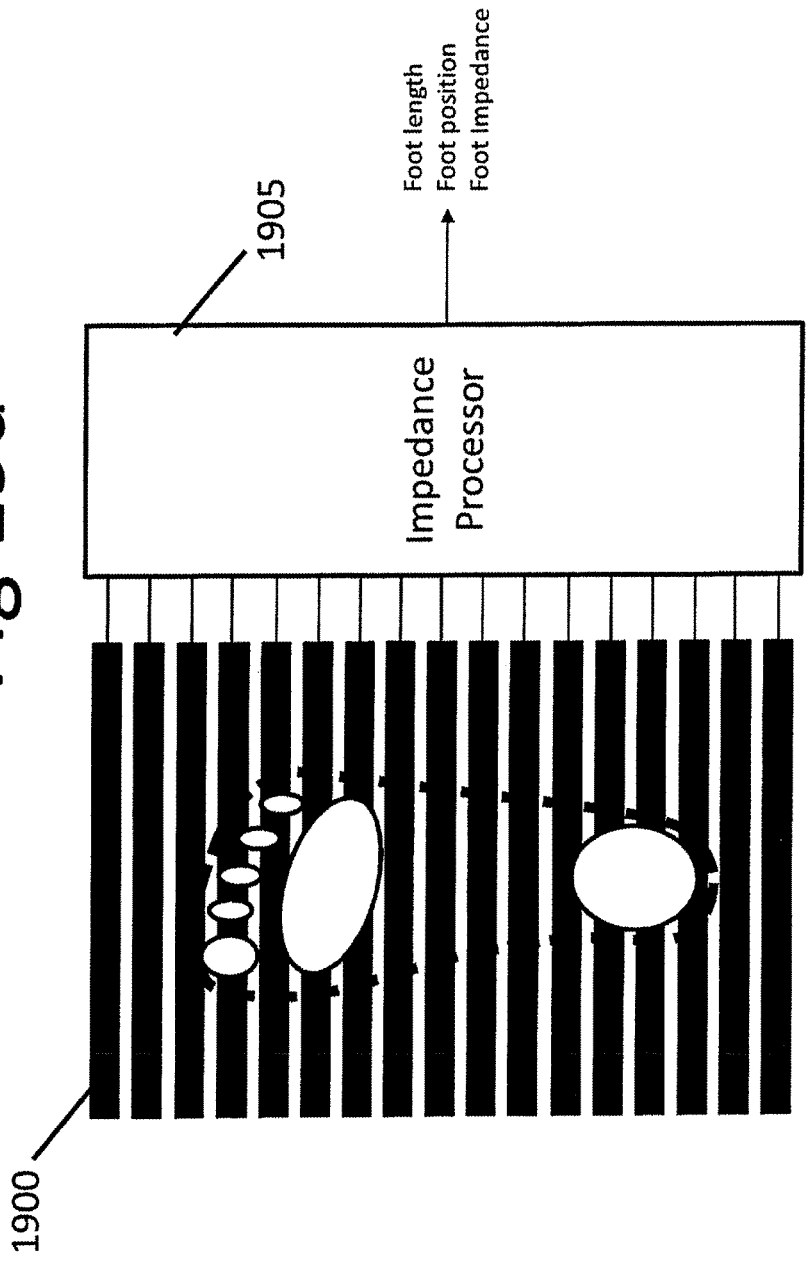

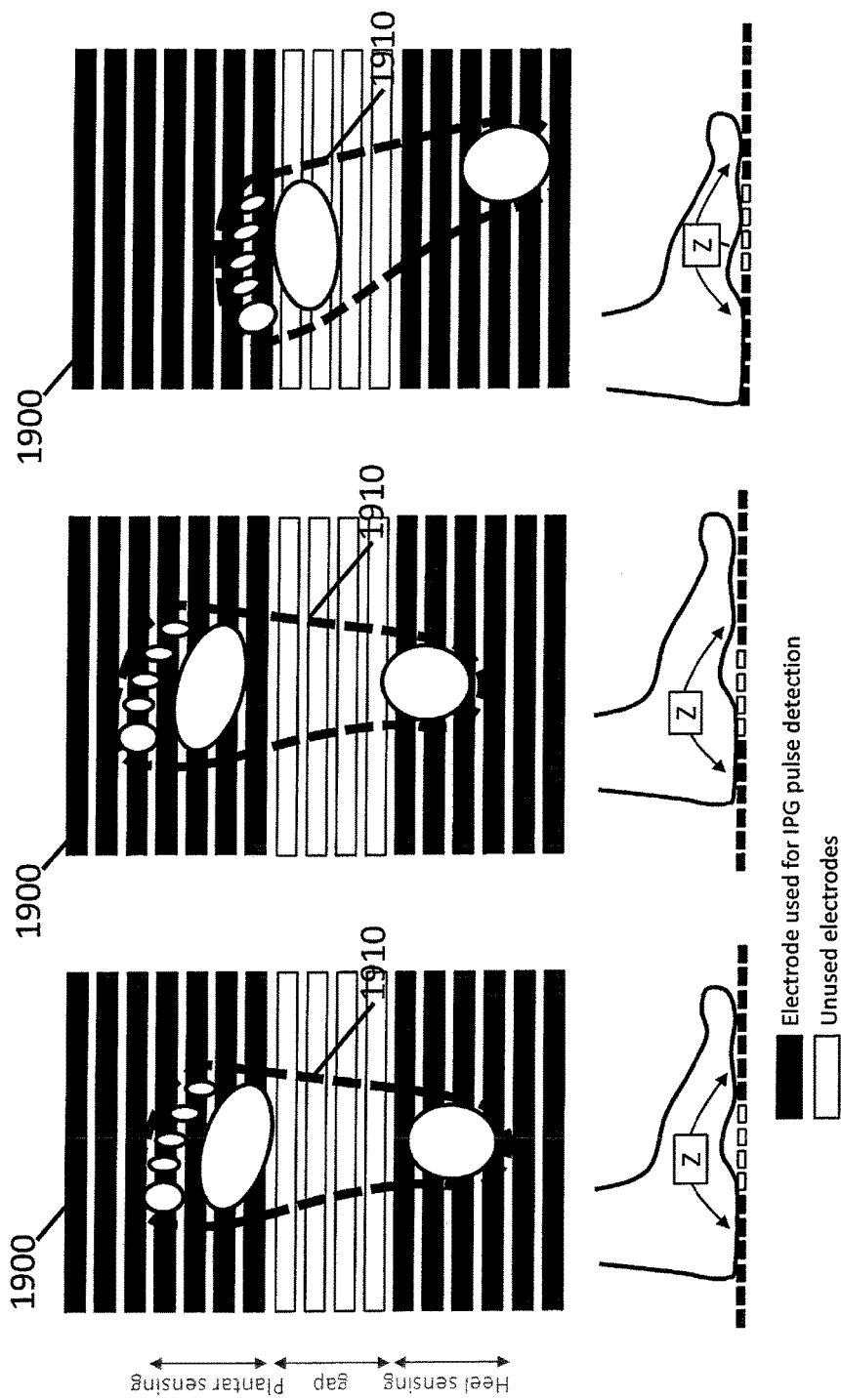

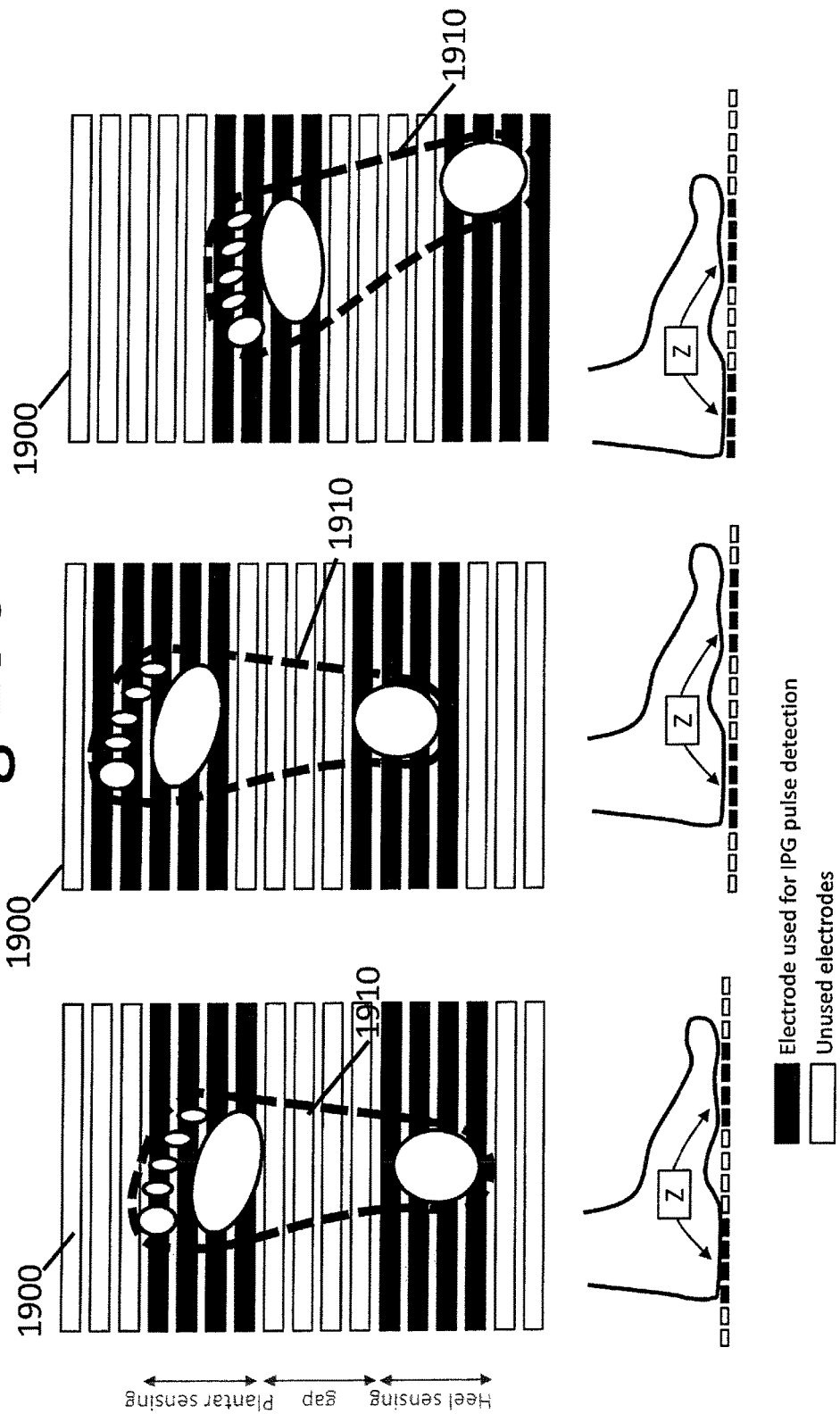

DEVICE AND METHOD HAVING AUTOMATIC USER-RESPONSIVE AND USER-SPECIFIC PHYSIOLOGICAL-METER PLATFORM

BACKGROUND

A variety of different physiological characteristics are monitored for many different applications. For instance, physiological monitoring instruments are often used to measure a number of patient vital signs, including blood oxygen level, body temperature, respiration rate and electrical activity for electrocardiogram (ECG) or electroencephalogram (EEG) measurements. For ECG measurements, a number of electrocardiograph leads may be connected to a patient's skin, and are used to obtain a signal from the patient.

Obtaining physiological signals can often require specialty equipment and intervention with medical professionals. For many applications, such requirements may be costly or burdensome. These and other matters have presented challenges to monitoring physiological characteristics.

SUMMARY OF THE DISCLOSURE

Various aspects of the present disclosure are directed toward methods, systems and apparatuses that are useful in making impedance-based measurements.

Various aspects of the present disclosure are directed toward multisensory user-specific biometric devices, systems and methods. Aspects of the present disclosure include user-interactive platforms, such as scales, large and/or full platform-area or dominating-area displays and related weighing devices, systems, and methods. Additionally, the present disclosure relates to electronic body scales that use impedance-based biometric measurements. Various other aspects of the present disclosure are directed to biometrics measurements such as body composition and cardiovascular information. Impedance measurements can be made through the feet to measure fat percentage, muscle mass percentage and body water percentage. Additionally, foot impedance-based cardiovascular measurements can be made for an ECG and sensing the properties of blood pulsations in the arteries, also known as impedance plethysmography (IPG), where both techniques can be used to quantify heart rate and/or pulse arrival timings (PAT). Cardiovascular IPG measures the change in impedance through the corresponding arteries between the sensing electrode pair segments synchronous to each heartbeat.

In certain embodiments, the present disclosure is directed to apparatuses and methods including a CPU and a memory circuit with user-corresponding data stored in the memory circuit, and a platform over which a plurality of electrodes are interleaved and configured and arranged for engaging a user. A plurality of measurement signals is obtained while a set of electrodes are concurrently contacting the user. While the plurality of electrodes is concurrently contacting a limb or other extremity of the user, a plurality of impendence-measurement signals is obtained from the plurality of electrodes. These impendence-measurement signals may (optionally) be the above-noted measurement signals. Based on biometrics of the user while approaching the platform, assessing who the user is while on the platform, and/or the plurality of measurement signals obtained from the plurality of electrodes, the CPU is used to access the user-corresponding data stored in the memory circuit, and thereby automatically recognize the user. This recognition is used for one or more of a variety of actions including, among others, transitioning from a low-power mode to a higher (power-up) mode, logging the user into the system and user-based logging of data and usages, and assessing which set of platform electrodes to use for obtaining the impendence-measurement signals. Based on a plurality of impedance-measurement signals being obtained from the electrodes while contacting the user, user-specific signals are generated and that correspond to the cardiovascular timings of the user.

In another embodiment, a plurality of impedance-measurement signals is obtained while a set of at least three electrodes are concurrently contacting a user. One of the plurality of impedance-measurement signals is obtained from two of the electrodes contacting one foot of the user with at least one other of the plurality of impedance-measurement signals being obtained between the one foot and a location of the user (e.g., along a lower limb, other foot, hand, shoulder) that does not include the one foot. A plurality of pulse characteristic signals are determined based on the plurality of impedance-measurement signals, with one of the pulse characteristic signals being extracted from one of the impedance-measurement signals and used as a timing reference to extract and process another of the pulse characteristic signals.

Another example embodiment is directed toward an apparatus that includes an impedance-measurement circuit that obtains a plurality of impedance-measurement signals via a set of electrodes while each of the electrodes is concurrently contacting a user. The set of electrodes includes a plurality of electrodes that contact one foot of the user, and includes at least one other electrode for contacting the user at a location that does not include the one foot (e.g., along a lower limb, other foot, hand, shoulder). The apparatus also includes a second circuit that determines a plurality of pulse characteristic signals based on the plurality of impedance-measurement signals. At least one of the impedance-measurement signals is obtained within the one foot and another of the impedance-measurement signals is obtained between the one foot and the other location. One of the pulse characteristic signals is extracted from one of the impedance-measurement signals and is used as a timing reference to extract and process another of the pulse characteristic signals.

In another embodiment, an apparatus includes a base unit including a platform area. The apparatus also includes a set of electrodes including a plurality of electrodes over the platform area for contacting one foot of a user and including at least one other electrode configured and arranged for contacting the user at a location along a lower limb (e.g., other foot) that does not include the one foot. Additionally, the apparatus includes pulse-processing circuitry communicatively coupled to, and configured with, the set of electrodes to obtain a plurality of (first and second) impedance-measurement signals while each of the electrodes is concurrently contacting the user and to determine a plurality of (first and second) pulse characteristic signals based on the plurality of (first and second) impedance-measurement signals. At least one of the (first) impedance-measurement signals is obtained within the one foot and another of the (second) impedance-measurement signals is obtained between the one foot and the other location. One of the (first and second) pulse characteristic signals is extracted from one of the impedance-measurement signals and is used as a timing reference to extract and process another of the pulse characteristic signals.

Another embodiment is directed to an apparatus having a base unit including a platform area, a set of electrodes and pulse-processing circuitry. The electrodes include a plurality of electrodes over the platform area for contacting a user at a limb extremity (being the hand or foot) and one or more other electrodes for contacting the user at a different location. The pulse-processing circuitry is communicatively coupled to, and configured with, the set of electrodes to obtain a plurality of (first and second) impedance-measurement signals while each of the electrodes is concurrently contacting the user and to determine a plurality of (first and second) pulse characteristic signals based on the plurality of (first and second) impedance-measurement signals. At least one of the (first) impedance-measurement signals is obtained within the limb extremity and another of the (second) impedance-measurement signals is obtained between the limb extremity and the other location. One of the (first and second) pulse characteristic signals is extracted from one of the impedance-measurement signals and is used as a timing reference to extract and process another of the pulse characteristic signals.

The above discussion/summary is not intended to describe each embodiment or every implementation of the present disclosure. The figures and detailed description that follow also exemplify various embodiments.

BRIEF DESCRIPTION OF THE DRAWINGS

Various example embodiments may be more completely understood in consideration of the following detailed description in connection with the accompanying drawings, in which:

FIG. 2 shows an example of the insensitivity to foot placement on scale electrodes with multiple excitation and sensing current paths, consistent with various aspects of the present disclosure;

FIGS. 3a-3b show example block diagrams depicting circuitry for sensing and measuring the cardiovascular time-varying IPG raw signals and steps to obtain a filtered IPG waveform, consistent with various aspects of the present disclosure;

FIG. 4 shows an example block diagram depicting signal processing steps to obtain fiducial references from the individual Leg IPG "beats," which are subsequently used to obtain fiducials in the Foot IPG, consistent with various aspects of the present disclosure;

FIG. 5 shows an example flowchart depicting signal processing to segment individual Foot IPG "beats" to produce an averaged IPG waveform of improved SNR, which is subsequently used to determine the fiducial of the averaged Foot IPG, consistent with various aspects of the present disclosure;

FIG. 7a shows examples of the Leg IPG signal with fiducials; the segmented Leg IPG into beats; and the ensemble averaged Leg IPG beat with fiducials and calculated SNR, for an exemplary low-quality recording, consistent with various aspects of the present disclosure;

FIG. 7b shows examples of the Foot IPG signal with fiducials derived from the Leg IPG fiducials; the segmented Foot IPG into beats; and the ensemble-averaged Foot IPG beat with fiducials and calculated SNR, for an exemplary low-quality recording, consistent with various aspects of the present disclosure;

FIGS. 9a-b show an example configuration to obtain the pulse transit time (PTT), using the first IPG as the triggering pulse for the Foot IPG and ballistocardiogram (BCG), consistent with various aspects of the present disclosure;

FIG. 11 shows an example graph of PTT correlations for two detection methods (white dots) Foot IPG only, and (black dots) Dual-IPG method, consistent with various aspects of the present disclosure;

FIG. 12 shows an example graph of pulse wave velocity (PWV) obtained from the present disclosure compared to the ages of 61 human test subjects, consistent with various aspects of the present disclosure;

FIG. 13 shows another example of a scale with interleaved foot electrodes to inject and sense current from one foot to another foot, and within one foot, consistent with various aspects of the present disclosure;

FIG. 14c shows another example approach to floating current sources is the use of transformer-coupled current sources, consistent with various aspects of the present disclosure;

FIGS. 15a-d show an example breakdown of a scale with interleaved foot electrodes to inject and sense current from one foot to another foot, and within one foot, consistent with various aspects of the present disclosure;

FIGS. 19a-c show example impedance as measured through different parts of the foot based on the foot position, consistent with various aspects of the present disclosure.

Figure 1:
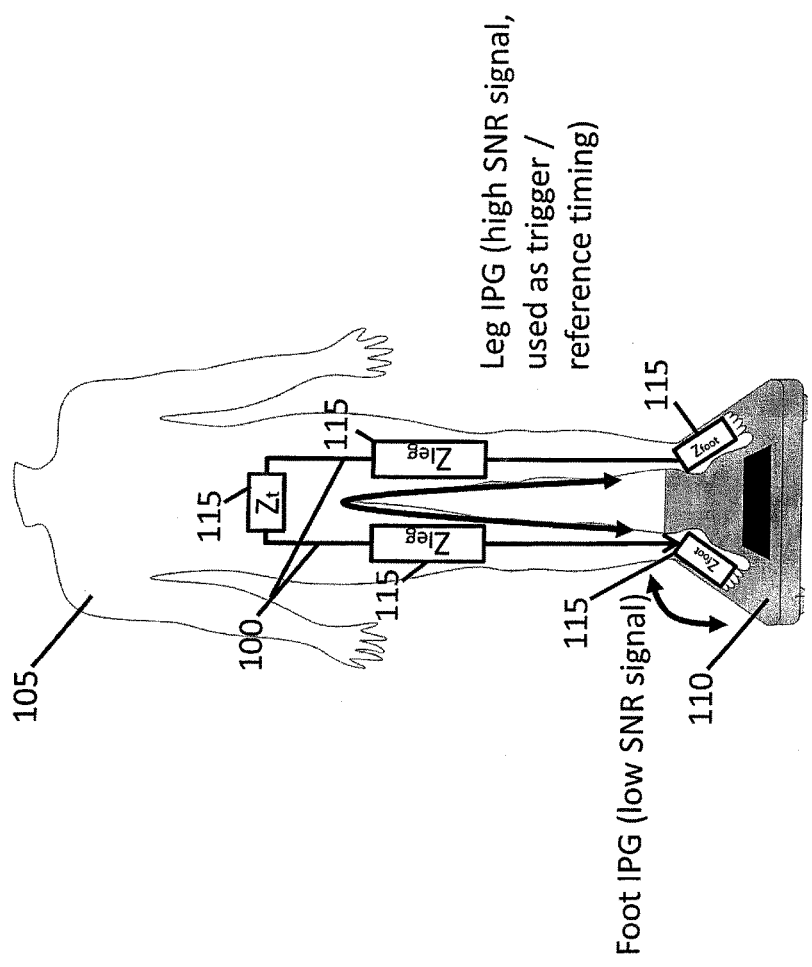
FIG. 1 shows current paths through the body for the IPG trigger pulse and Foot IPG, consistent with various aspects of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DESCRIPTION

Various aspects of the present disclosure relate to the sensing, detection, and quantification of at least two simultaneously acquired impedance-based signals. The simultaneously acquired impedance-based signals are associated with quasi-periodic electro-mechanical cardiovascular functions, and simultaneous cardiovascular signals measured by the impedance sensors, due to the beating of an individual's heart, where the measured signals are used to determine at least one cardiovascular related characteristic of the user for determining the heart activity, health, or abnormality associated with the user's cardiovascular system. The sensors can be embedded in a user platform, such as a weighing scale-based platform, where the user stands stationary on the platform, with the user's feet in contact with the platform, where the impedance measurements are obtained where the user is standing with bare feet.

Additionally, certain aspects of the present disclosure are directed toward methods that include obtaining a plurality of impedance-measurement signals while a set of electrodes are concurrently contacting a user. One of the plurality of impedance-measurement signals is obtained from two of the electrodes contacting one foot of the user and at least one other of the plurality of impedance-measurement signals being obtained between the one foot and a location of the user (e.g., along a lower limb, other foot, hand, shoulder) that does not include the one foot. Additionally, the method includes determining a plurality of pulse characteristic signals based on the plurality of impedance-measurement signals, wherein one of the pulse characteristic signals is extracted from one of the impedance-measurement signals and is used as a timing reference to extract and process another of the pulse characteristic signals.

In certain embodiments, the plurality of impedance-measurement signals includes at least two impedance-measurement signals between the one foot and the other location. The plurality of pulse characteristic signals are determined by assessing, as part of a signal optimization process, impedance-measurement signals including the at least two other impedance-measurement signals. Further, in certain embodiments, a signal is obtained, based on the timing reference, which is indicative of synchronous information and that corresponds to information in a BCG. Additionally, the methods can include conveying modulated current between selected ones of the electrodes. The plurality of impedance-measurement signals may, for example, be carried out in response to current conveyed between selected ones of the electrodes. Additionally, the methods, consistent with various aspects of the present disclosure, include a step of providing an IPG measurement within the one foot. Additionally, in certain embodiments, the two electrodes contacting one foot of the user are configured in an inter-digitated pattern of positions over a base unit that contains circuitry communicatively coupled to the inter-digitated pattern. The circuitry uses the inter-digitated pattern of positions for the step of determining a plurality of pulse characteristic signals based on the plurality of impedance-measurement signals, and for providing an IPG measurement within the one foot.

For embodiments involving a weighing scale or other platform that the user, and similarly-venued personnel (e.g., co-workers, friends, roommates, colleagues), would use in the home, office or other such venue on a regular and frequent basis, the present disclosure is directed to a substantially-enclosed apparatus, as would be a weighing scale, wherein the apparatus includes a platform which is part of a housing or enclosure. The platform includes a surface area with electrodes that are interleaved and configured and arranged for engaging a user as he or she steps onto the platform. Within the housing is a CPU (e.g., one or more computer processor circuits) and a memory circuit with user-corresponding data stored in the memory circuit. The platform, over which the electrodes are interleaved, are integrated and communicatively connected with the CPU. The CPU is programmed with modules as a set of integrated circuitry which is configured and arranged for automatically obtaining a plurality of measurement signals from the plurality of electrodes. As is advantageous for operation by a battery circuit (with a limited supply of energy), this integrated circuitry operates in a reduced power-consumption mode and at least one higher power-consumption mode of operation. The CPU and the memory circuit are configured and arrange with the electrodes to operate as follows: while the plurality of electrodes are concurrently contacting a limb of the user, operating the integrated circuitry and therefrom automatically obtaining the plurality of measurement signals from the plurality of electrodes; before obtaining a plurality of measurement signals by operating the circuitry, using a signal-sense circuit to sense wireless-signals indicative of the user approaching the platform and, in response, causing the circuitry to transition from the reduced power-consumption mode of operation and at least one higher power-consumption mode of operation; and after the circuitry is operating in the at least one higher power-consumption mode of operation, causing the CPU to access the user-corresponding data stored in the memory circuit and thereafter cause a plurality of impedance-measurement signals to be obtained by using the plurality of electrodes while they are contacting the user via the platform and, therefrom, generating signals corresponding to cardiovascular timings of the user.

The platform apparatus can also include a camera configured and arranged to be activated in response to a motion detection indication, such as from a PIR circuit and a responsive CPU module that evaluates the amount of radiation received by the PIR circuit. The camera is configured to capture at least one image of the user (whether still image(s) or a short video) while the user is on the platform or approaching the platform (as the user's motion is sensed and detected). The CPU then stores the user image(s) in the memory circuit for retrieval at a later time for verification (e.g., administrative, medical or security personnel) of correspondence between the user and biometric or physiological data stored as being specific to the user. The CPU can also be configured to permit remote access to the memory circuit by an authorized agent of medical or security personnel by using an authorized access protocol.

Consistent with some of the above aspects, in specific implementations, the platform apparatus has a signal-sense circuit configured with or as a passive infrared (PIR) circuit, and the CPU programmed to sense the user approaching the platform. The CPU wakes up in response to the signal-sense circuit and to the motion detection indication as provided and determined by the CPU. When equipped with a camera, the camera is activated in response to the motion detection and captures user images while the user is approaching the platform or while the user is on the platform. Further, a user-output device can be included in the form of one of a speaker, a display visible through the platform and/or a foot-tactile vibration circuit. The foot-tactile vibration circuit is responsive to the CPU and wherein the user-output device is configured and arranged to communicate with the user while the user is engaging the platform. Thus, in certain more-important applications such as those pertaining to provision of medical opinions or more critical bio-identification applications, the platform apparatus permits access to the user-specific data stored and logged in the memory circuit by an authorized agent of medical or security personnel by using an authorized access protocol; whereas other user-specific data pertinent to the user, such as impedance measurements performed while the user is on the platform apparatus, is provided as feedback to the user concurrent with the use.

In other related embodiments, the platform apparatus's signal-sense circuit is configured with the CPU to effect a learning of which user is about to step on, or has stepped on, the platform in preparation for selecting the appropriate electrodes for obtaining the plurality of impedance-measurement signals. These learnings, which can be stored in and retrieved from the memory circuit for comparison to previous logs or recordings. For example, selecting the appropriate electrodes can be based on user-recognition/identification and/or measurement results that indicate one or more of the following user-specific attributes: foot impedance, foot length, and type of arch. Any one or more of these can be used as an indication of a level of confidence of as identifying or corresponding to bio-metric attributes specific to the user.

In medical (and security) applications, for example, the impedance measurements obtained from the plurality of interleaved electrodes can then be used to provide various cardio-related information that is user-specific including, as non-limiting examples, synchronous information obtained from the user and that corresponds to information in a ballistocardiogram (BCG) and an impedance plethysmography (IPG) measurements. By ensuring that the user, for whom such data was obtained, matches other bio-metric data as obtained concurrently for the same user, medical (and security) personnel can then assess, diagnose and/or identify with high degrees of confidence and accuracy.

Other embodiments of the present disclosure are directed toward an apparatus that includes an impedance-measurement circuit that obtains a plurality of impedance-measurement signals via a set of electrodes while each of the electrodes is concurrently contacting a user (e.g., with the electrodes being part of the impedance-measurement circuit). The set of electrodes includes a plurality of electrodes for contacting one foot of the user and including at least another electrode for contacting the user at a location (e.g., along a lower limb, other foot, hand, shoulder) that does not include the one foot. The apparatus also includes a second circuit that determines a plurality of pulse characteristic signals based on the plurality of impedance-measurement signals. At least one of the impedance-measurement signals are obtained within the one foot and another of the impedance-measurement signals is obtained between the one foot and the other location. One of the pulse characteristic signals is extracted from one of the impedance-measurement signals and is used as a timing reference to extract and process another of the pulse characteristic signals.

In certain embodiments, the second circuit determines the pulse characteristic signals by comparing and assessing the impedance-measurement signals as part of a signal optimization process. The impedance-measurement signals include a foot impedance-measurement signal within the one foot, and at least two other impedance-measurement signals are measured between the one foot and the other location. The second circuit also determines the pulse characteristic signals by assessing, as part of a signal optimization process, each of the foot impedance-measurement signals and the at least two other impedance-measurement signals.

Other embodiments of the present disclosure are directed toward apparatuses that include a base unit including a platform area. The apparatus also includes a set of electrodes including a plurality of electrodes over the platform area for contacting one foot of a user, and at least one other electrode for contacting the user at a location along a lower limb that does not include the one foot (e.g., other foot). Additionally, the apparatus includes pulse-processing circuitry communicatively coupled to, and configured with, the set of electrodes to obtain a plurality of (first and second) impedance-measurement signals while each of the electrodes is concurrently contacting the user and. The pulse-processing circuitry and electrodes also determine a plurality of (first and second) pulse characteristic signals based on the plurality of (first and second) impedance-measurement signals. At least one of the (first) impedance-measurement signals is obtained within the one foot and another of the (second) impedance-measurement signals is obtained between the one foot and the other location. One of the (first and second) pulse characteristic signals is extracted from one of the impedance-measurement signals and is used as a timing reference to extract and process another of the pulse characteristic signals.

In certain embodiments, the base unit houses the pulse-processing circuitry, and the lower limb location of the user is on the other foot. Further, the pulse characteristic signals can indicate pulse arrival times. Additionally, in certain embodiments, the set of electrodes includes at least four electrodes. In these embodiments, the pulse-processing circuitry is configured to obtain at least four impedance-measurement signals while each of the electrodes is concurrently contacting the user. The pulse-processing circuitry also determines the plurality of pulse characteristic signals by comparing at least two of the plurality of impedance-measurement signals and selecting one of the compared plurality of impedance-measurement signals over another of the compared plurality of impedance-measurement signals. Further, the pulse-processing circuitry can obtain a signal indicative of synchronous information based on the timing reference. Additionally, the pulse-processing circuitry can obtain a signal indicative of synchronous information based on the timing reference. The signal containing (or indicative of) synchronous information may correspond to information in a BCG or impedance cardiogram. Further, the pulse-processing circuitry and the set of electrodes can introduce an injection impedance signal to the user and to sense, in response, a return impedance signal.

Other embodiments of the present disclosure are directed to a plurality of electrodes that operate with pulse-processing circuitry to provide an IPG measurement within the one foot. The electrodes can be configured in an inter-digitated pattern of positions over the platform. The pulse-processing circuitry can use the inter-digitated pattern of positions to provide an IPG measurement within the one foot.

Certain embodiments of the present disclosure employ current-sourcing circuitry for presenting a plurality of current-injection signals to respective ones of the set of electrodes, with at least one of the current-injection signals modulated for current differentiation. Two injection electrodes impose current to the user from the current-sourcing circuitry. The pulse-processing circuitry senses the current-injection signals in two distinct body segments of the user. In certain more specific embodiments, the two distinct body segments respectively include a foot segment of the user and a segment including the legs of the user. The pulse-processing circuitry can provide leg and foot impedance measurements based on synchronous demodulation of the current-injection signals.

In some embodiments, the set of electrodes includes an electrode pattern element and are characterized as having a resistivity lower than 300 ohms/square and including at least one of indium tin oxide (ITO), stainless steel, aluminum and tantalum. Additionally, certain embodiments of the present disclosure employ a weighing scale, in which the base unit is integral with a housing that encloses the weighing scale and the pulse-processing circuitry. The platform area of the base unit provides a user-standing area sufficient for the user to stand with both of the feet on the platform area. The set of electrodes may include a pattern of interleaved Kelvin electrode pairs for the one foot. In certain more specific embodiments, the pattern of interleaved Kelvin electrode pairs mitigate sensitivity to foot placement on the platform area.

In certain embodiments, the electrodes include a pattern of at least two interleaved Kelvin electrode pairs for the one foot that mitigate sensitivity to foot placement on the platform area, thereby mitigating impedance-measurement interference caused by movements of the user. Certain embodiments of the present disclosure can include BCG sensing circuitry and an electrode pattern element that defines the plurality of electrodes for the one foot. The pulse-processing circuitry can be configured with the BCG sensing circuitry and the electrode pattern element to provide data for measuring arterial pulse wave velocity ("aPWV data") and, in response, to augment the aPWV data with data obtained by BCG sensing.

In certain embodiments, the lower limb location is the other foot. In these such embodiments, the set of electrodes includes a pattern of at least two interleaved Kelvin electrode pairs for the one foot which are configured to mitigate sensitivity to foot placement on the platform area, thereby mitigating impedance-measurement interference caused by movements of the user. Additionally, in certain embodiments the pulse-processing circuitry determines the plurality of pulse characteristic signals within 60 seconds from when the user initially stands on the platform area.

Apparatuses, consistent with the present disclosure, can include a base unit having a platform area, a set of electrodes and pulse-processing circuitry. The electrodes include a plurality of electrodes configured over the platform area for contacting a user at a limb extremity, being the hand or foot, and at least one other electrode for contacting the user at a different location. The pulse-processing circuitry is communicatively coupled to, and configured with, the set of electrodes to obtain a plurality of (first and second) impedance-measurement signals while each of the electrodes is concurrently contacting the user and to determine a plurality of (first and second) pulse characteristic signals based on the plurality of (first and second) impedance-measurement signals. Additionally, at least one of the (first) impedance-measurement signals are obtained within the limb extremity and another of the (second) impedance-measurement signals are obtained between the limb extremity and the other location. One of the (first and second) pulse characteristic signals is extracted from one of the impedance-measurement signals and is used as a timing reference to extract and process another of the pulse characteristic signals.

In certain embodiments, the set of electrodes includes a pattern of interleaved Kelvin electrode pairs for the limb extremity. Further, the set of electrodes can include a pattern of at least two interleaved Kelvin electrode pairs for the limb extremity which are configured to mitigate sensitivity to placement of the limb extremity on the platform area, thereby mitigating impedance-measurement interference caused by movements of the user.

Additionally, certain embodiments use a 4-electrode bio-electronal impedance analysis (BIA) scale, where foot-to-foot IPG uses a Kelvin connection (as for standard BIA). Additionally, certain embodiments of the present disclosure use an impedance signal other than foot-to-foot as reference. It is possible to use the same approach using an impedance signal between the hand and the foot.

Turning now to the figures, FIG. 1 shows current paths 100 through the body of a user 105 standing on a scale 110 for the IPG trigger pulse and Foot IPG, consistent with various aspects of the present disclosure. Impedance measurements 115 are measured when the user 105 is standing and wearing clothing articles over the feet such as socks or shoes, within the practical limitations of capacitive-based impedance sensing, with energy limits considered safe for human use. The measurements 115 can also be made with non-clothing material placed between the user's bare feet and contact electrodes, such as thin films or sheets of plastic, glass, paper or wax paper, whereby the electrodes operate within energy limits considered safe for human use. The IPG measurements also can be sensed in the presence of callouses on the user's feet that normally diminish the quality of the signal.

As shown in FIG. 1, the user 105 is standing on a scale 110, where the tissues of the user's body will be modeled as a series of impedance elements, and where the time-varying impedance elements change in response to cardiovascular and non-cardiovascular movements of the user. ECG and IPG measurements can be sensed through the feet and can be challenging to take due to small impedance signals with (1) low SNR, and because they are (2) frequently masked or distorted by other electrical activity in the body such as the muscle firings in the legs to maintain balance. The human body is unsteady while standing still, and constant changes in weight distribution occur to maintain balance. As such, cardiovascular signals that are measured with weighing scale-based sensors typically yield signals with poor SNR, such as the Foot IPG and standing BCG. Thus, such scale-based signals require a stable and high quality synchronous timing reference, to segment individual heartbeat-related signals for signal averaging to yield an averaged signal with higher SNR versus respective individual measurements.

The ECG can be used as the reference (or trigger) signal to segment a series of heartbeat-related signals measured by secondary sensors (optical, electrical, magnetic, pressure, microwave, piezo, etc.) for averaging a series of heartbeat-related signals together, to improve the SNR of the secondary measurement. The ECG has an intrinsically high SNR when measured with body-worn gel electrodes, or via dry electrodes on handgrip sensors. In contrast, the ECG has a low SNR when measured using foot electrodes while standing on said scale platforms; unless the user is standing perfectly still to eliminate electrical noises from the leg muscles firing due to body motion. As such, ECG measurements at the feet while standing are considered to be an unreliable trigger signal (low SNR). Therefore, it is often difficult to obtain a reliable cardiovascular trigger reference timing when using ECG sensors incorporated in base scale platform devices. Both Inan, et al. (IEEE Transactions on Information Technology in Biomedicine, 14:5, 1188-1196, 2010) and Shin, et al. (Physiological Measurement, 30, 679-693, 2009) have shown that the ECG component of the electrical signal measured between the two feet while standing was rapidly overpowered by the electromyogram (EMG) signal resulting from the leg muscle activity involved in maintaining balance.

The accuracy of cardiovascular information obtained from weighing scale platforms is also influenced by measurement time. The number of beats obtained from heartbeat-related signals for signal averaging is a function of measurement time and heart rate. The Mayo Clinic cites that typical resting heart rates range from 60 to 100 beats per minute. Therefore, short signal acquisition periods may yield a low number of beats to average, which may cause measurement uncertainty, also known as the standard error in the mean (SEM). SEM is the standard deviation of the sample mean estimate of a population mean. Where, SE is the standard error in the samples N, which is related to the standard error or the population S.

$$SE = \frac{S}{\sqrt{N}}$$

For example, a five second signal acquisition period may yield a maximum of five to eight beats for ensemble averaging, while a 10 second signal acquisition could yield 10-16 beats. However, the number of beats available for averaging and SNR determination is usually reduced for the following factors; (1) truncation of the first and last ensemble beat in the recording by the algorithm, (2) triggering beats falsely missed by triggering algorithm, (3) cardiorespiratory variability, (4) excessive body motion corrupting the trigger and Foot IPG signal, and (5) loss of foot contact with the measurement electrodes.

Sources of noise can require multiple solutions for overall SNR improvements for the signal being averaged. Longer measurement times increase the number of beats lost to truncation, false missed triggering, and excessive motion. Longer measurement times also reduce variability from cardiorespiratory effects. Therefore, if shorter measurement times (e.g., less than 30 seconds) are desired for scale-based sensor platforms, sensing improvements need to tolerate body motion and loss of foot contact with the measurement electrodes.

The human cardiovascular system includes a heart with four chambers, separated by valves that return blood to the heart from the venous system into the right side of the heart, through the pulmonary circulation to oxygenate the blood, which then returns to the left side of the heart, where the oxygenated blood is pressurized by the left ventricles and is pumped into the arterial circulation, where blood is distributed to the organs and tissues to supply oxygen. The cardiovascular or circulatory system is designed to ensure maintenance of oxygen availability and is often the limiting factor for cell survival. The heart normally pumps five to six liters of blood every minute during rest and maximum cardiac output during exercise can increase up to seven-fold, by modulating heart rate and stroke volume. The factors that affect heart rate include the degree of autonomic innervation, fitness level, age and hormones. Factors affecting stroke volume include heart size, fitness level, contractility or pre-ejection period, ejection duration, preload or end-diastolic volume, afterload or systemic resistance. The cardiovascular system is constantly adapting to maintain a homeostasis (set point) that minimizes the work done by the heart to maintain cardiac output. As such, blood pressure is continually adjusting to minimize work demands during rest. Cardiovascular disease encompasses a variety of abnormalities in (or that affect) the cardiovascular system that degrade the efficiency of the system, which include but are not limited to chronically elevated blood pressure, elevated cholesterol levels, edema, endothelial dysfunction, arrhythmias, arterial stiffening, atherosclerosis, vascular wall thickening, stenosis, coronary artery disease, heart attack, stroke, renal dysfunction, enlarged heart, heart failure, diabetes, obesity and pulmonary disorders.

Each cardiac cycle results in a pulse of blood being delivered into the arterial tree. The heart completes cycles of atrial systole, delivering blood to the ventricles, followed by ventricular systole delivering blood into the lungs and the systemic arterial circulation, where the diastole cycle begins. In early diastole the ventricles relax and fill with blood, then in mid-diastole the atria and ventricles are relaxed and the ventricles continue to fill with blood. In late diastole, the sinoatrial node (the heart's pacemaker) depolarizes then contracting the atria, the ventricles are filled with more blood and the depolarization then reaches the atrioventricular node and enters the ventricular side beginning the systole phase. The ventricles contract and the blood is pumped from the ventricles to the arteries.

The ECG is the measurement of the heart's electrical activity and can be described in five phases. The P-wave represents atrial depolarization, the PR interval is the time between the P-wave and the start of the QRS complex. The QRS wave complex represents ventricular depolarization. The QRS complex is the strongest wave in the ECG and is frequently used as the de facto timing reference for the cardiovascular cycle. Atrial repolarization is masked by the QRS complex. The ST interval then follows which represents the period of zero potential between ventricular depolarization and repolarization. The cycle concludes with the T-wave representing ventricular repolarization.

The blood ejected into the arteries creates vascular movements due to the blood's momentum. The blood mass ejected by the heart first travels headward in the ascending aorta and travels around the aortic arch then travels down the descending aorta. The diameter of the aorta increases significantly during the systole phase due to the high compliance (low stiffness) of the aortic wall. Blood traveling in the descending aorta then bifurcates in the iliac branch which then transitions into a stiffer arterial region due to the muscular artery composition of the leg arteries. The blood pulsation continues down the leg and foot. All along the way, the arteries branch into arteries of smaller diameter until reaching the capillary beds where the pulsatile blood flow turns into steady blood flow, delivering oxygen to the tissues. The blood then returns to the venous system terminating in the vena cava, where blood returns to the right atrium of the heart for the subsequent cardiac cycle.

Surprisingly, high quality simultaneous recordings of the Leg IPG and Foot IPG are attainable in a practical manner (e.g., a user operating the device correctly simply by standing on the impedance body scale foot electrodes), and can be used to obtain reliable trigger fiducial timings from the Leg IPG signal. This acquisition can be far less sensitive to motion-induced noise from the Leg EMG that often compromises Leg ECG measurements. Furthermore, it has been discovered that interleaving the two Kelvin electrode pairs for a single foot, result in a design that is insensitive to foot placement within the boundaries of the overall electrode area. As such, the user is no longer constrained to comply with accurate foot placement on conventional single foot Kelvin arrangements, which are highly prone to introducing motion artifacts into the IPG signal, or result in a loss of contact if the foot is slightly misaligned. Interleaved designs begin when one or more electrode surfaces cross over a single imaginary boundary line separating an excitation and sensing electrode pair. The interleaving is configured to maintain uniform foot surface contact area on the excitation and sensing electrode pair, regardless of the positioning of the foot over the combined area of the electrode pair.

Various aspects of the present disclosure include a weighing scale platform (e.g., scale 110) of an area sufficient for an adult of average size to stand comfortably still and minimize postural swaying. The nominal scale length (same orientation as foot length) is 12 inches and the width is 12 inches. The width can be increased to be consistent with the feet at shoulder width or slightly broader (e.g., 14 to 18 inches, respectively).

Figure 1A:
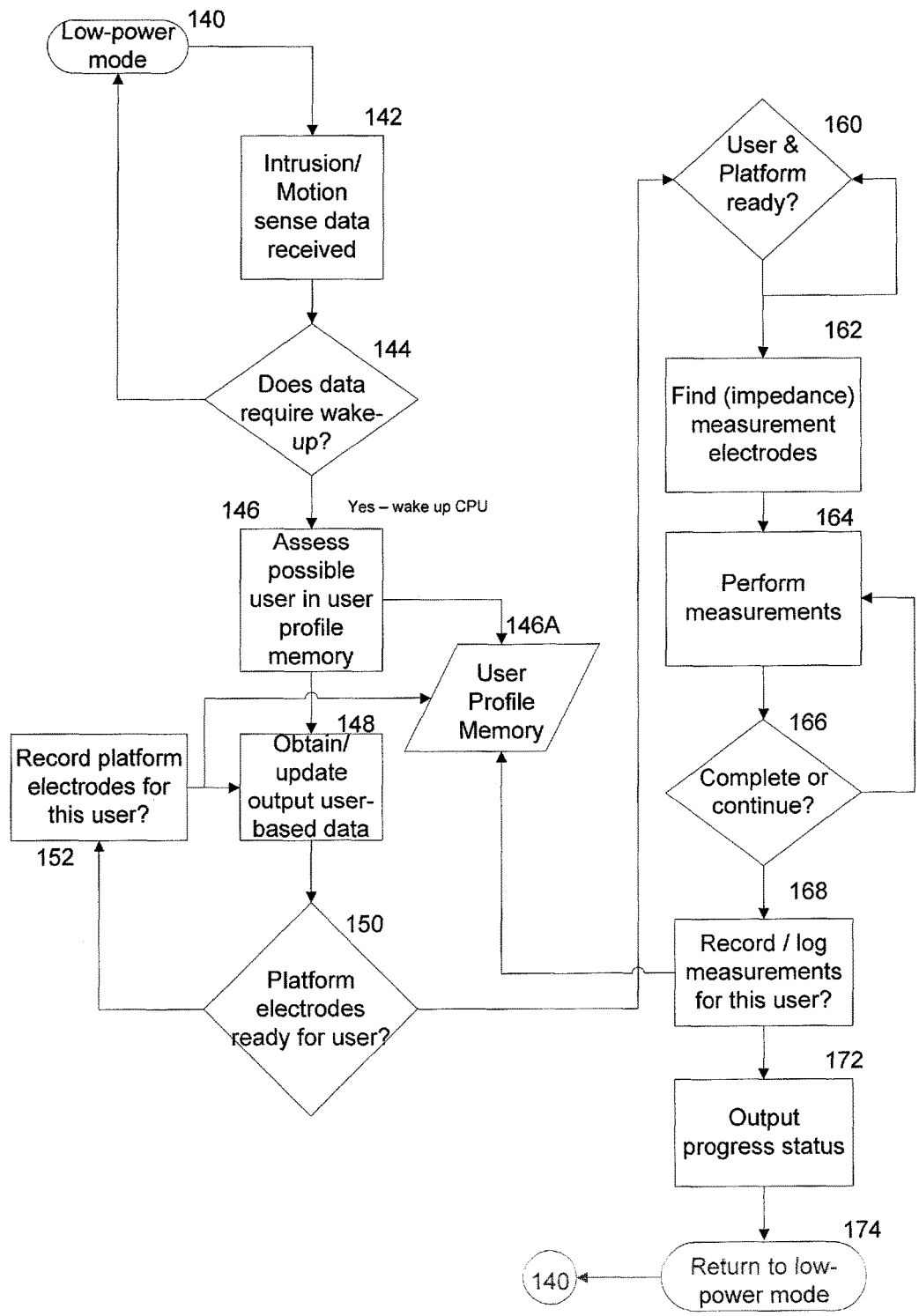
FIG. 1a is a flow chart illustrating an example manner in which a user-specific physiologic meter/scale may be programmed to provide features consistent with aspects of the present disclosure.

FIG. 1*a* is a flow chart depicting an example manner in which a user-specific physiologic meter or scale may be programmed in accordance with the present disclosure. This flow chart uses a computer processor circuit (or CPU) along with a memory circuit shown herein as user profile memory 146*a*. The CPU operates in a low-power consumption mode, which may be in off mode or a low-power sleep mode, and at least one other higher power consumption mode of operation. As exemplary circuits for transitioning between such a low-power and higher power modes, the CPU can be integrated with presence and/or motion sense circuits, such as a PIR circuit and/or gyro PIR circuit. In a typical application, the PIR circuit provides a constant flow of data indicative of amounts of radiation sensed in a field of view directed by the PIR circuit. For instance, the PIR circuit can be installed behind a transparent upper surface of the platform (such as through the display screen of the platform apparatus) and installed at an angle so that the motion of the user, as the user approaches the platform apparatus, can be sensed. Radiation from the user, upon reaching a certain detectable level, wakes up the CPU which then transitions from the low-power mode, as depicted in block 140, to a regular mode of operation. In alternative embodiments, the low-power mode of operation is transitioned from a response to another remote/wireless input used as a presence to awaken the CPU. In other embodiments, motion can be sensed with a single integrated microphone or microphone array, to detect the sounds of a user approaching, or user motion can be detected by an accelerometer integrated in the scale.

Accordingly, from block 140, flow proceeds to block 142 where the user or other intrusion is sensed as data received at the platform apparatus. At block 144, the circuitry assesses whether the received data qualifies as requiring a wake up. If not, flow turns to block 140. If however, wake up is required, flow proceeds from block 144 to block 146 where the CPU assesses whether a possible previous user has approached the platform apparatus. This assessment is performed by the CPU accessing the user profile memory 146A and comparing data stored therein for one or more such previous users with criteria corresponding to the received data that caused the wake up. Such criteria might include, for example, the time of the day (early morning or late morning), the pace at which the user approached the platform apparatus as sensed by the motion detection circuitry, the height of the user as indicated by the motion sensing circuitry and/or a camera installed and integrated with the CPU, and/or more sophisticated bio-metric data provided by the user and/or automatically by the circuitry in the platform apparatus.

As discussed herein, such sophisticated circuitry can include one or more of the following user-specific attributes: foot length, type of foot arch, weight of user, and/or manner and speed at which the user steps onto the platform apparatus, or sounds made by the user's motion or by speech. As is also conventional, facial or body-feature recognition may also be used in connection with the camera and comparisons of images therefrom to images in the user profile memory.

From block 146, flow proceeds to block 148 where the CPU obtains and/or updates user corresponding data in the user profile memory. As a learning program is developed in the user profile memory, each access and use of the platform apparatus is used to expand on the data and profile for each such user. From block 148, flow proceeds to block 150 where a decision is made regarding whether the set of electrodes at the upper surface of the platform are ready for the user, such as may be based on the data obtained from the user profile memory. For example, delays may ensue from the user moving his or her feet about the upper surface of the platform apparatus, as may occur while certain data is being retrieved by the CPU (whether internally or from an external source such as a program or configuration data updates from the Internet cloud) or when the user has stepped over a certain area configured for providing display information back to the user. If the electrodes are not ready for the user, flow proceeds from block 150 to block 152 to accommodate this delay.

Once the CPU determines that the electrodes are ready for use while the user is standing on the platform surface, flow proceeds to block 160. Stabilization of the user on the platform surface may be ascertained by injecting current through the electrodes via the interleaved arrangement thereof. Where such current is returned via other electrodes for a particular foot and/or foot size, and is consistent for a relatively brief period of time, for example, a few seconds, the CPU can assume that the user is standing still and ready to use the electrodes and related circuitry.

At block 160, a decision is made that both the user and the platform apparatus are ready for measuring impedance and certain segments of the user's body, including at least one foot.

The remaining flow of FIG. 1*a* includes the application and sensing of current through the electrodes for finding the optimal electrodes (162) and for performing impedance measurements (block 164). These measurements are continued until completed at block 166 and all such useful measurements are recorded and are logged in the user profile memory for this specific user, at block 168. At block 172, the CPU generates output data to provide feedback as to the completion of the measurements and, as can be indicated as a request via the user profile for this user, as an overall report on the progress for the user and relative to previous measurements made for this user has stored in the user profile memory. Such feedback may be shown on the display, through a speaker with co-located apertures in the platforms housing for audible reception by the user, and/or by vibration circuitry which, upon vibration under control of the CPU, the user can sense through one or both feet while standing on the scale. From this output at block 172, flow returns to the low power mode as indicated at block 174 with the return to the beginning of the flow at the block 140.

FIG. 2 shows an example of the insensitivity to foot placement 200 on scale electrode pairs 205/210 with multiple excitation paths 220 and sensing current paths 215, consistent with various aspects of the present disclosure. An aspect of the platform is that it has a thickness and strength to support a human adult of at least 200 pounds without fracturing, and another aspect of the device platform is comprised of at least six electrodes, where the first electrode pair 205 is solid and the second electrode pair 210 are interleaved. Another aspect is the first and second interleaved electrode pairs 205/210 are separated by a distance of at least 40+/−5 millimeters, where the nominal separation of less than 40 millimeters has been shown to degrade the single Foot IPG signal. Another key aspect is the electrode patterns are made from materials with low resistivity such as stainless steel, aluminum, hardened gold, ITO, index matched ITO (IMITO), carbon printed electrodes, conductive tapes, silver-impregnated carbon printed electrodes, conductive adhesives, and similar materials with resistivity lower than 300 ohms/sq. In the certain embodiments, the resistivity is below 150 ohms/sq. The electrodes are connected to the electronic circuitry in the scale by routing the electrodes around the edges of the scale to the surface below, or through at least one hole in the scale (e.g., a via hole).

Suitable electrode arrangements for dual Foot IPG measurements can be realized in other embodiments. In certain embodiments, the interleaved electrodes are patterned on the reverse side of a thin piece (e.g., less than 2 mm) of high-ion-exchange (HIE) glass, which is attached to a scale substrate and used in capacitive sensing mode. In certain embodiments, the interleaved electrodes are patterned onto a thin piece of paper or plastic which can be rolled up or folded for easy storage. In certain embodiments, the interleaved electrodes are integrated onto the surface of a tablet computer for portable IPG measurements. In certain embodiments, the interleaved electrodes are patterned onto a kapton substrate that is used as a flex circuit.

In certain embodiments, the scale area has a length of 10 inches with a width of eight inches for a miniature scale platform. Alternatively, the scale may be larger (up to 36 inches wide) for use in bariatric class scales. In certain embodiments, the scale platform with interleaved electrodes is incorporated into a floor tile that can be incorporated into a room such as a bathroom. In certain embodiments, the scale folds in half with a hinge for improved portability and storage. Alternatively, the scale platform is comprised of two separable halves, one half for the left foot and the other half for the right foot, for improved portability and storage. In certain embodiments for ambulatory measurements, the interleaved excitation and sensing electrode pairs are incorporated into a shoe insert for the detection of heart rate and a corresponding pulse arrival time (PAT). Alternatively, the interleaved excitation and sensing electrode pairs are incorporated into a pair of socks, to be worn for the detection of heart rate and a corresponding PAT.

In the present disclosure, the leg and foot impedance measurements can be simultaneously carried out using a multi-frequency approach, in which the leg and foot impedances are excited by currents modulated at two different frequencies, and the resulting voltages are selectively measured using a synchronous demodulator as shown in FIG. 3a. This homodyning approach can be used to separate signals (in this case, the voltage drop due to the imposed current) with very high accuracy and selectivity.

This measurement configuration is based on a four-point configuration in order to minimize the impact of the contact resistance between the electrode and the foot, a practice well-known in the art of impedance measurement. In this configuration the current is injected from a set of two electrodes (the "injection" and "return" electrodes), and the voltage drop resulting from the passage of this current through the resistance is sensed by two separate electrodes (the "sense" electrodes), usually located in the path of the current. Since the sense electrodes are not carrying any current (by virtue of their connection to a high-impedance differential amplifier), the contact impedance does not significantly alter the sensed voltage.

In order to sense two distinct segments of the body (the legs and the foot), two separate current paths are defined by way of electrode positioning. Therefore two injection electrodes are used, each connected to a current source modulated at a different frequency. The injection electrode for leg impedance is located under the plantar region of the left foot, while the injection electrode for the Foot IPG is located under the heel of the right foot. Both current sources share the same return electrode located under the plantar region of the right foot. This is an illustrative example. Other configurations may be used.

The sensing electrodes can be localized so as to sense the corresponding segments. Leg IPG sensing electrodes are located under the heels of each foot, while the two foot sensing electrodes are located under the heel and plantar areas of the right foot. The inter-digitated nature of the right foot electrodes ensures a four-point contact for proper impedance measurement, irrespectively of the foot position, as already explained.

Figure 3B:
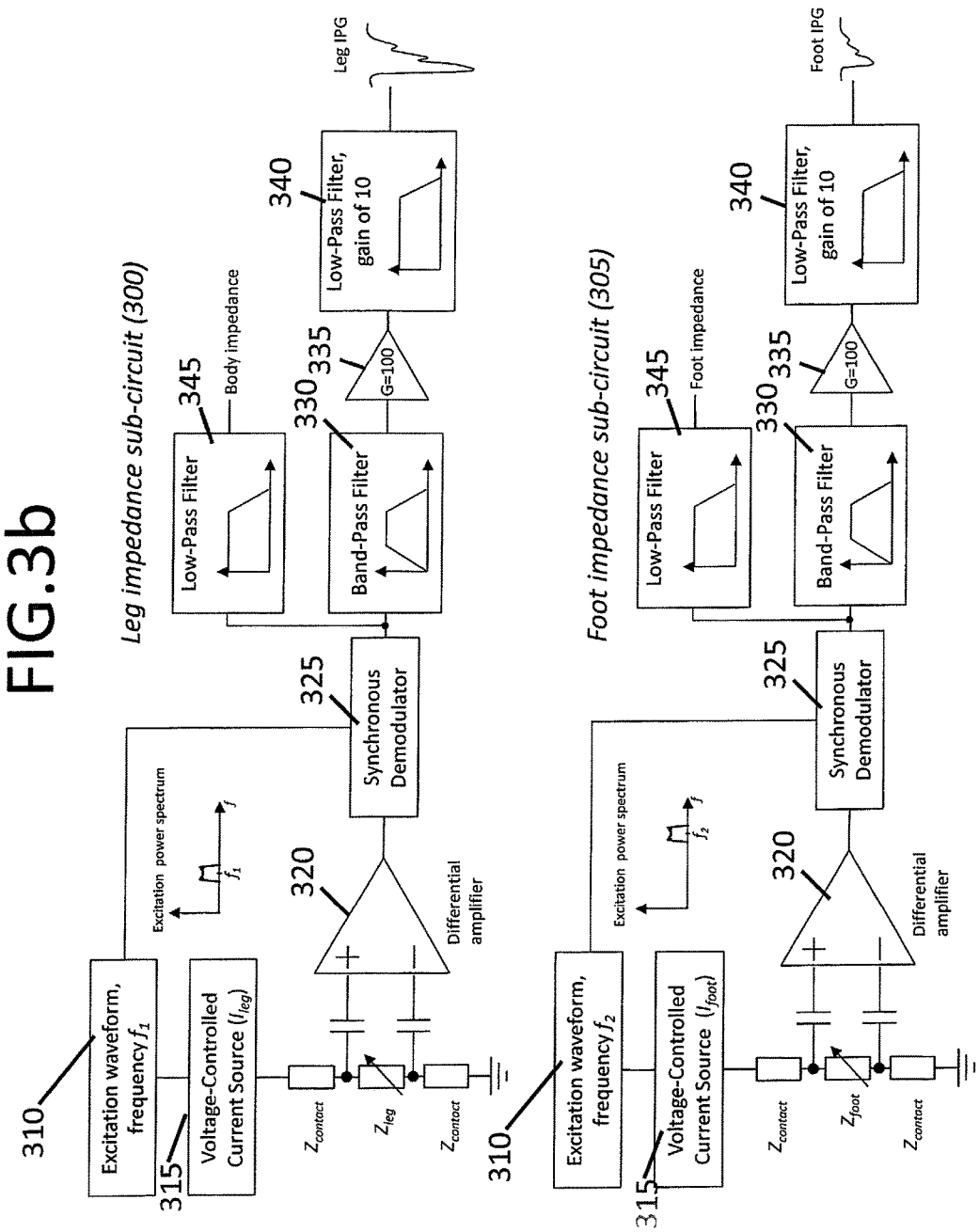

FIGS. 3a-3b show example block diagrams depicting the circuitry for sensing and measuring the cardiovascular time-varying IPG raw signals and steps to obtain a filtered IPG waveform, consistent with various aspects of the present disclosure. The example block diagrams shown in FIGS. 3a-3b are separated in to a leg impedance sub-circuit 300 and a foot impedance sub-circuit 305.

Excitation is provided by way of an excitation waveform circuit 310. The excitation waveform circuit 310 provides an excitation signal by way of a various types of frequency signals (as is shown in FIG. 3a) or, more specifically, a square wave signal (as shown in FIG. 3b). As is shown in FIG. 3b, the square wave signal is a 5 V at a frequency between 15,625 Hz and 1 MHz is generated from a quartz oscillator (such as an ECS-100AC from ECS International, Inc.) divided down by a chain of toggle flip-flops (e.g. a CD4024 from Texas Instruments, Inc.), each dividing stage providing a frequency half of its input (i.e., 1 Mhz, 500 kHz, 250 kHz, 125 kHz, 62.5 kHz, 31.250 kHz and 15.625 kHz). This (square) wave is then AC-coupled, scaled down to the desired amplitude and fed to a voltage-controlled current source circuit 315. The generated current is passed through a decoupling capacitor (for safety) to the excitation electrode, and returned to ground through the return electrode (grounded-load configuration). Amplitudes of 1 and 4 mA peak-to-peak are typically used for Leg and Foot IPGs, respectively.

The voltage drop across the segment of interest (legs or foot) is sensed using an instrumentation differential amplifier (e.g., Analog Devices AD8421) 320. The sense electrodes on the scale are AC-coupled to the input of the differential amplifier 320 (configured for unity gain), and any residual DC offset is removed with a DC restoration circuit (as exemplified in Burr-Brown App Note Application Bulletin, SBOA003, 1991, or Burr-Brown/Texas Instruments INA118 datasheet).

The signal is then demodulated with a synchronous demodulator circuit 325. The demodulation is achieved in this example by multiplying the signal by 1 or −1 synchronously with the current excitation. Such alternating gain is provided by an operational amplifier and an analog switch (SPST), such as an ADG442 from Analog Devices). More specifically, the signal is connected to both positive and negative inputs through 10 kOhm resistors. The output is connected to the negative input with a 10 kOhm resistor as well, and the switch is connected between the ground and the positive input. When open, the gain of the stage is unity. When closed (positive input grounded), the stage acts as an inverting amplifier of the gain −1. Alternatively, other demodulators such as analog multipliers or mixers can be used.

Once demodulated, the signal is band-pass filtered (0.4-80 Hz) with a first-order band-pass filter circuit 330 before being amplified with a gain of 100 with a non-inverting amplifier circuit 335 (e.g., using an LT1058 operational amplifier from Linear Technologies). The amplified signal is further amplified by 10 and low-pass filtered (cut-off at 30 Hz) using a low-pass filter circuit 340 such as 2-pole Sallen-Key filter stage with gain. The signal is then ready for digitization and further processing. In certain embodiments, the amplified signal can be passed through an additional low-pass filter circuit 345 to determine body or foot impedance.

In certain embodiments, the generation of the excitation voltage signal, of appropriate frequency and amplitude, is carried out by a microcontroller, such as MSP430 (Texas Instruments, Inc.). The voltage waveform can be generated using the on-chip timers and digital input/outputs or pulse width modulation (PWM) peripherals, and scaled down to the appropriate voltage through fixed resistive dividers, active attenuators/amplifiers using on-chip or off-chip operational amplifiers, as well as programmable gain amplifiers or programmable resistors. Alternatively, the waveforms can be directly generated by on- or off-chip digital-to-analog converters (DACs).

In certain embodiments, the shape of the excitation is not square, but sinusoidal. Such configuration would reduce the requirements on bandwidth and slew rate for the current source and instrumentation amplifier. Harmonics, potentially leading to higher electromagnetic interference (EMI), would also be reduced. Such excitation may also reduce electronics noise on the circuit itself. Lastly, the lack of harmonics from sine wave excitation may provide a more flexible selection of frequencies in a multi-frequency impedance system, as excitation waveforms have fewer opportunities to interfere between each other. Due to the concentration of energy in the fundamental frequency, sine wave excitation could also be more power-efficient.

In certain embodiments, the shape of the excitation is not square, but trapezoidal. While not as optimal as a sinusoidal wave, trapezoidal waves (or square waves whose edges have been smoothed out by a limited bandwidth or slew rate) still provide an advantage in term of EMI and electronic noise due to the reduced harmonics.

To further reduce potential EMI, other strategies may be used, such as by dithering the square wave signal (i.e., introducing jitter in the edges following a fixed or random pattern) which leads to so-called spread spectrum signals, in which the energy is not localized at one specific frequency (or a set of harmonics), but rather distributed around a frequency (or a set of harmonics). An example of a spread-spectrum circuit suitable for Dual-IPG measurement is shown in FIG. 3b. Because of the synchronous demodulation scheme, phase-to-phase variability introduced by spread-spectrum techniques will not affect the impedance measurement. Such a spread-spectrum signal can be generated by, but not limited to, specialized circuits (e.g., Maxim MAX31C80, SiTime SiT9001), or generic microcontrollers (see Application Report SLAA291, Texas Instruments, Inc.). These spread-spectrum techniques can be combined with clock dividers to generate lower frequencies as well.

As may be clear to one skilled in the art, these methods of simultaneous measurement of impedance in the leg and foot can be used for standard Body Impedance Analysis (BIA), aiming at extracting relative content of total water, free-water, fat mass and others. Impedance measurements for BIA are typically done at frequencies ranging from kilohertz up to several megahertz. The multi-frequency measurement methods described above can readily be used for such BIA, provided the circuit can be modified so that the DC component of the impedance is not canceled by the instrumentation amplifier (no DC restoration circuit used). The high-pass filter can be implemented after the instrumentation amplifier, enabling the measurement of the DC component used for BIA. This multi-frequency technique can also be combined with traditional sequential measurements often used for BIA, in which the impedance is measured at several frequencies sequentially. These measurements can be repeated in several body segments for segmental BIAs, using a switch matrix to drive the current into the desired body segments.

Figure 14A:
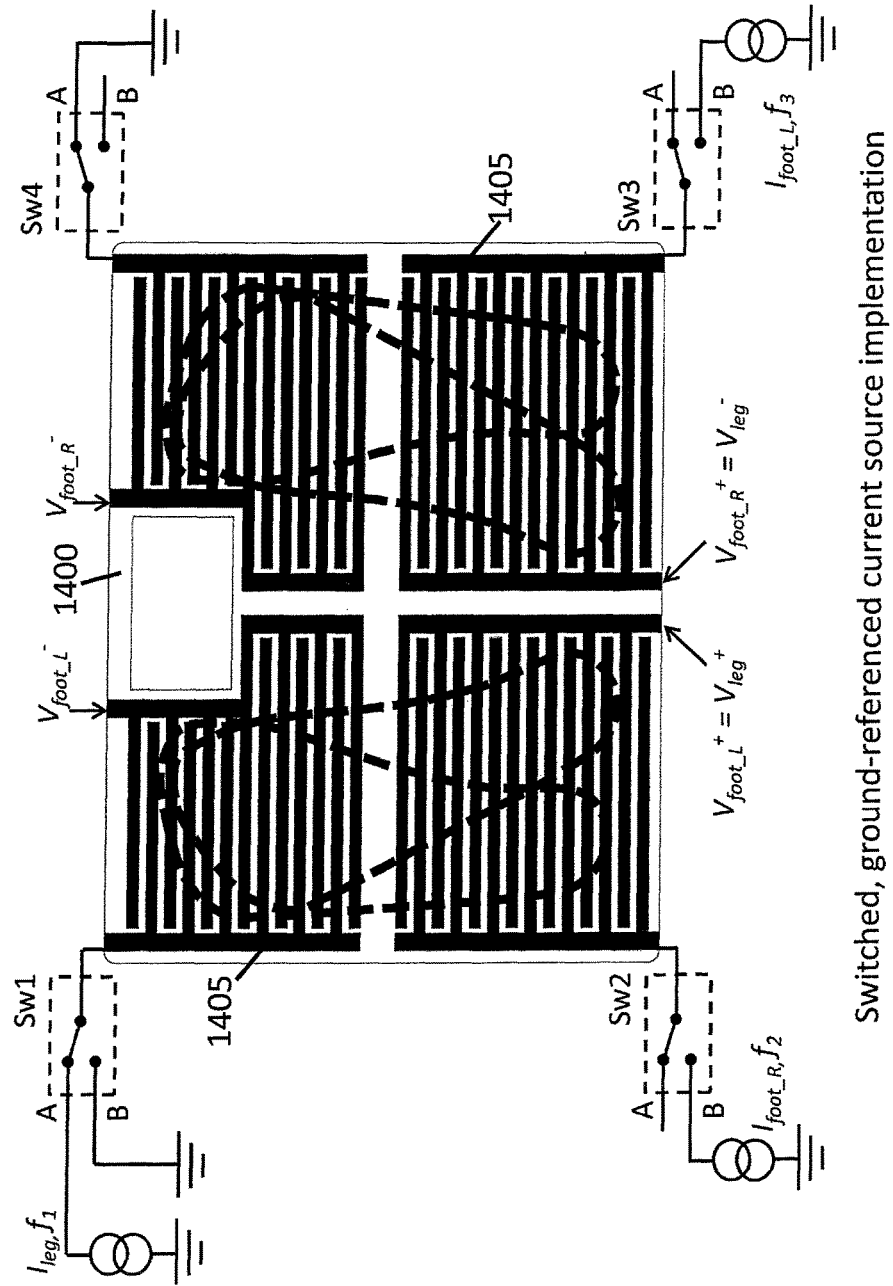
FIG. 14a shows another example of a scale with interleaved foot electrodes to inject and sense current from one foot to another foot, and measure Foot IPG signals in both feet, consistent with various aspects of the present disclosure.

While FIG. 2 shows a circuit and electrode configuration suitable to measure two different segments (legs and one foot), this approach is not readily extendable to more segments due to the shared current return electrode (ground). To overcome this limitation, and in particular provide simultaneous measurements in both feet, the system can be augmented with analog switches to provide time-multiplexing of the impedance measurements in the different segments. This multiplexing can either be a one-time sequencing (each segment is measured once), or interleaved at a high-enough frequency that the signal can be simultaneously measured on each segment. The minimum multiplexing rate for proper reconstruction is twice the bandwidth of the measured signal, based on signal processing theory, which equals to about 100 Hz for the impedance signal considered here. The rate must also allow for the signal path to settle in between switching, usually limiting the maximum multiplexing rate. Referring to FIG. 14a, one cycle might start the measurement of the leg impedance and left foot impedances (similarly to previously described, sharing a common return electrode), but then follow with a measurement of the right foot after reconfiguring the switches. Typical switch configurations for the various measurements are shown in the table below.

|  | Switch #1 (Sw1) | Switch #2 (Sw2) | Switch #3 (Sw3) | Switch #4 (Sw4) |
| --- | --- | --- | --- | --- |
| Legs | A | A or B | A or B | A |
| Right Foot | A | A or B | B | A |
| Left Foot | B | B | A or B | B |

Since right and left feet are measured sequentially, one should note that a unique current source (at the same frequency) may be used to measure both, providing that the current source is not connected to the two feet simultaneously through the switches, in which case the current would be divided between two paths. One should also note that a fully-sequential measurement, using a single current source (at a single frequency) successively connected to the three different injection electrodes, could be used as well, with the proper switch configuration sequence (no split current path).

In certain embodiments, the measurement of various body segments, and in particular the legs, right foot and left foot, is achieved simultaneously due to as many floating current sources as segments to be measured, running at separate frequency so they can individually be demodulated. Such configuration is exemplified in FIG. 14b for three segments (legs, right and left feet). Such configuration has the advantage to provide true simultaneous measurements without the added complexity of time-multiplexing/demultiplexing, and associated switching circuitry. An example of such floating current source can be found in Plickett, et al., Physiological Measurement, 32 (2011). Another approach to floating current sources is the use of transformer-coupled current sources (as depicted in FIG. 14c). Using transformers to inject current into the electrodes enables the use of simpler, grounded-load current sources on the primary, while the electrodes are connected to the secondary. Turn ratio would typically be 1:1, and since frequencies of interest for impedance measurement are typically in the 10-1000 kHz (occasionally 1 kHz for BIA), relatively small transformers can be used. In order to limit the common mode voltage of the body, one of the electrodes in contact with the foot can be grounded.

While certain embodiments presented in the above specification have used current sources for excitation, it should be clear to a person skilled in the art that the excitation can also be performed by a voltage source, where the resulting injection current is monitored by a current sense circuit so that impedance can still be derived by the ratio of the sensed voltage (on the sense electrodes) over the sensed current (injected in the excitation electrodes).

It should be noted that broadband spectroscopy methods could also be used for measuring impedances at several frequencies. Such technique has the advantage of lower EMI and simultaneous measurement of impedances at numerous frequencies. These methods typically use a chirp signal, a noise signal or an impulse signal to excite the load (impedance) at many frequencies simultaneously, while sampling the resulting response at high frequency so as to allow the computation (usually in the frequency domain) of the impedance over the desired frequency range. Combined with time-multiplexing and current switching described above, multi-segment broadband spectroscopy can be readily achieved.

Various aspects of the present disclosure are directed toward robust timing extraction of the blood pressure pulse in the foot which is achieved by means of a two-step processing. In a first step, the usually high-SNR Leg IPG is used to derive a reference (trigger) timing for each heart pulse. In a second step, a specific timing in the lower-SNR Foot IPG is extracted by detecting its associated feature within a restricted window of time around the timing of the Leg IPG. Such guided detection leads to a naturally more robust detection of foot timings.

Figure 3C:
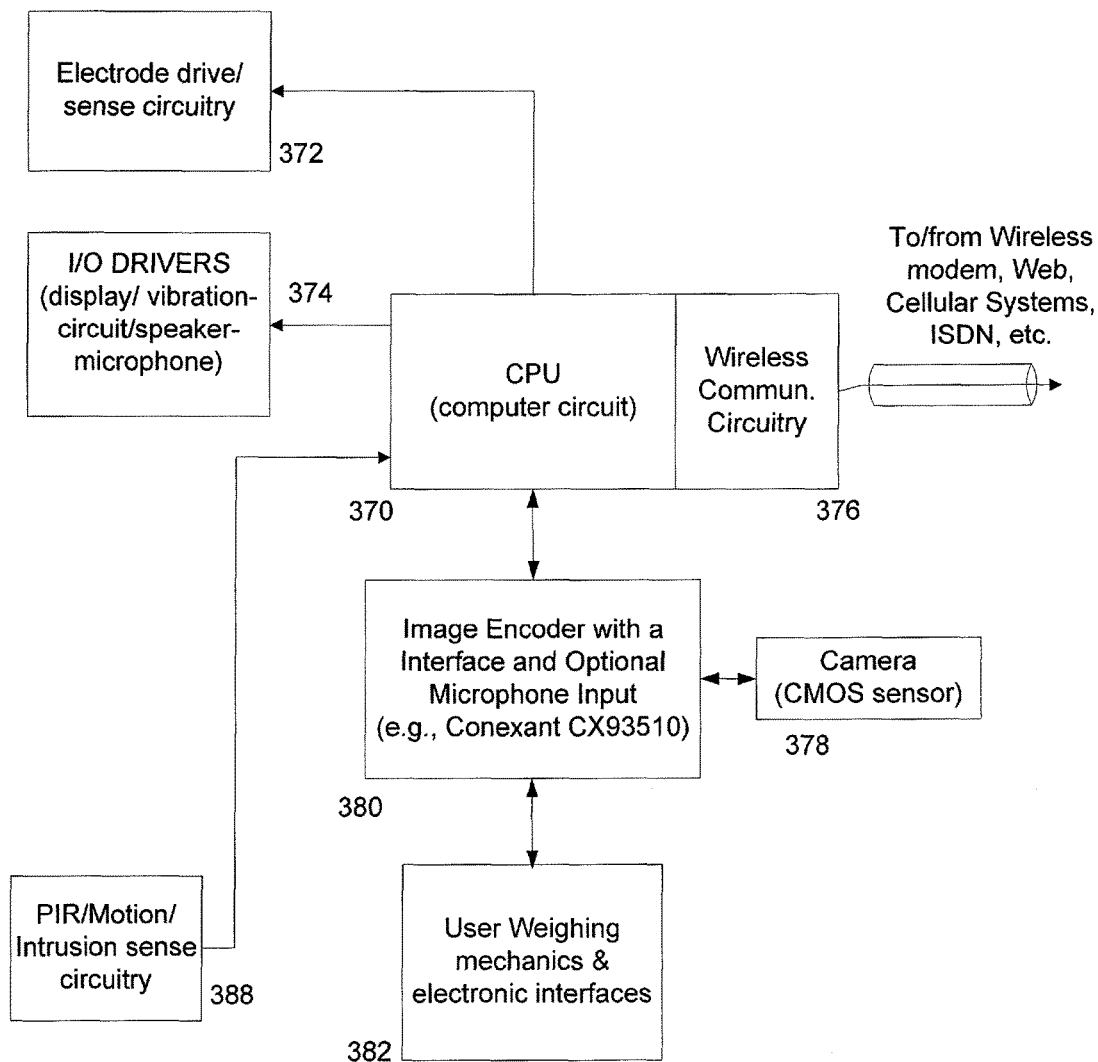
FIG. 3c depicts an example block diagram of circuitry for operating core circuits and modules, including for example those of FIGS. 3a-3b, used in various specific embodiments of the present disclosure.

Consistent with yet further embodiments of the present disclosure, FIG. 3c depicts an example block diagram of circuitry for operating core circuits and modules, including, for example, the operation of the CPU as in FIG. 1a with the related more specific circuit blocks/modules in FIGS. 3A-3B. As shown in the center of FIG. 3c, the main computer circuit 370 is shown with other previously-mentioned circuitry in a generalized manner without showing some of the detailed circuitry such as for amplification and current injection/sensing (372). The computer circuit 370 can be used as a control circuit with an internal memory circuit (or as integrated with the memory circuit for the user profile memory 146A of FIG. 1a) for causing, processing and/or receiving sensed input signals as at block 372. As discussed, these sensed signals can be responsive to injection current and/or these signals can be sensed at least for initially locating positions of the foot or feet on the platform area, by less complex grid-based sense circuitry surrounding the platform area as is convention in capacitive touch-screen surfaces which, in certain embodiments, the platform area includes.

As noted, the memory circuit can be used not only for the user profile memory, but also as to provide configuration and/or program code and/or other data such as user-specific data from another authorized source such as from a user monitoring his/her logged data and/or profile from a remote desk-top. The remote device or desk-top can communicate with and access such data via a wireless communication circuit 376 via a wireless modem, router, ISDN channel, cellular systems, Bluetooth and/or other broadband pathway or private channel. For example, the wireless communication circuit 376 can provide an interface between an app on the user's cellular telephone/tablet (e.g., phablet, IPhone and/or IPad) and the platform apparatus, wherefrom the IPhone can be the output/input interface for the platform (scale) apparatus including, for example, an output display, speaker and/or microphone, and vibration circuitry; each of these I/O aspects and components being discussed herein in connection with other example embodiments.

A camera 378 and image encoder circuit 380 (with compression and related features) can also be incorporated as an option. As discussed above, the weighing scale components, as in block 382, are also optionally included in the housing which encloses and/or surrounds the platform apparatus.

For long-lasting battery life in the platform apparatus (batteries not shown), at least the CPU 370, the wireless communication circuit 376, and other current draining circuits are inactive unless and until activated in response to the intrusion/sense circuitry 388. As shown, one specific implementation employs a Conexant chip (e.g., CX93510) to assist in the low-power operation. This type of circuitry is specifically designed for motion sensors configured with a camera for visual verification and image and video monitoring applications (such as by supporting JPEG and MJPEG image compression and processing for both color and black and white images). When combined with an external CMOS sensor, the chip retrieves and stores compressed JPEG and audio data in an on-chip memory circuit (e.g., 256 KB/128 KB frame buffer) so as to alleviate the necessity of external memory. The chip uses a simple register set via the microprocessor interface and allows for wide flexibility in terms of compatible operation with another microprocessor.

In one specific embodiment, a method of using the platform with the plurality of electrodes are concurrently contacting a limb of the user, includes operating such to automatically obtain measurement signals from the plurality of electrodes. As noted above, these measurement signals might initially be through less complex (e.g., capacitive grid-type) sense circuitry. Before or while obtaining a plurality of measurement signals by operating the circuitry, the signal-sense circuitry 388 is used to sense wireless-signals indicative of the user approaching the platform and, in response, causing the CPU circuitry 370 to transition from a reduced power-consumption mode of operation and at least one higher power-consumption mode of operation. After the circuitry is operating in the higher power-consumption mode of operation, the CPU accesses the user-corresponding data stored in the memory circuit and thereafter causes a plurality of impedance-measurement signals to be obtained by using the plurality of electrodes while they are contacting the user via the platform; therefrom, the CPU generates signals corresponding to cardiovascular timings of the user.

This method can employ the signal-sense circuit as a passive infrared detector and with the CPU programmed (as a separate module) to evaluate whether radiation from the passive infrared detector is indicative of a human. For example, sensed levels of radiation that would correspond to a live being that has a size which is less than a person of a three-foot height, and/or not being sensed as moving for more than a couple seconds, can be assessed as being a non-human.

Accordingly, as the user is recognized as being human, the CPU is activated and begins to attempt the discernment process of which user might be approaching. This is performed by the CPU accessing the user-corresponding data stored in the memory circuit (the user profile memory). If the user is recognized based on parameters such as discussed above (e.g., time of morning, speed of approach, etc.), the CPU can also select one of a plurality of different types of user-discernible visual/audible/tactile information and for presenting the discerned user with visual/audible/tactile information that was retrieved from the memory as being specific to the user. For example, user-selected visual/audible data can be outputted for the user. Also, responsive to the motion detection indication, the camera can be activated to capture at least one image of the user while the user is approaching the platform (and/or while the user is on the platform to log confirmation of the same user with the measured impedance information). As shown in block 374 of FIG. 3c, where a speaker is also integrated with the CPU, the user can simply command the platform apparatus to start the process and activation proceeds accordingly.

In another such method, the circuitry of FIG. 3c is used with the plurality of electrodes being interleaved and engaging the user, as a combination weighing scale (via block 382) and a physiologic user-specific impedance-measurement device. By using the impedance-measurement signals and obtaining at least two impedance-measurement signals between one foot of the user and another location of the user, the interleaved electrodes assist the CPU in providing measurement results that indicate one or more of the following user-specific attributes as being indicative or common to the user: foot impedance, foot length, and type of arch, and wherein one or more of the user-specific attributes are accessed, by being read or stored, in the memory circuit and identified as being specific to the user. This information can be later retrieved by the user, medical and/or security personnel, according to a data-access authorization protocol as might be established upon initial configuration for the user.

Figure 3D:
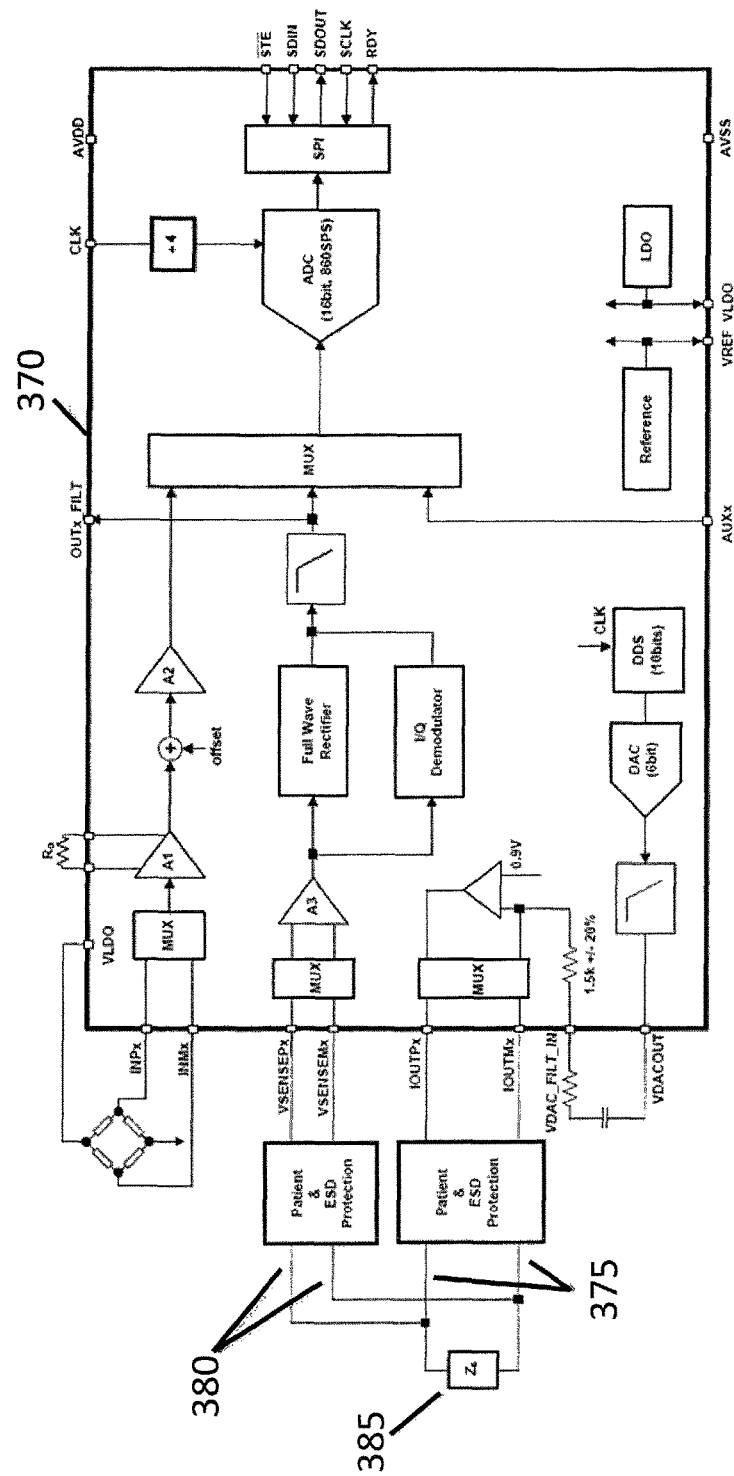
FIG. 3d shows an exemplary block diagram depicting the circuitry for interpreting signals received from electrodes.

FIG. 3d shows an exemplary block diagram depicting the circuitry for interpreting signals received from electrodes (e.g., 372 of FIG. 3c), and/or CPU 370 of FIG. 3c. The input electrodes 375 transmit various electrical signals through the patient's body (depending on the desired biometric and physiological test to be conducted) and output electrodes 380 receive the modified signal as affected by a user's electrical impedance 385. Once received by the output electrodes 380, the modified signal is processed by processor circuitry 370 based on the selected test. Signal processing conducted by the processor circuitry 370 is discussed in more detail above (with regard to FIGS. 3a-b). In certain embodiments of the present disclosure, the circuitry within 370 is provided by Texas Instruments part # AFE4300.

FIG. 4 shows an example block diagram depicting signal processing steps to obtain fiducial references from the individual Leg IPG "beats," which are subsequently used to obtain fiducials in the Foot IPG, consistent with various aspects of the present disclosure. In the first step, as shown in block 400, the Leg IP and the Foot IPG are simultaneously measured. As shown at 405, the Leg IPG is low-pass filtered at 20 Hz with an 8-pole Butterworth filter, and inverted so that pulses have an upward peak. The location of the pulses is then determined by taking the derivative of this signal, integrating over a 100 ms moving window, zeroing the negative values, removing the large artifacts by zeroing values beyond 15× the median of the signal, zeroing the values below a threshold defined by the mean of the signal, and then searching for local maxima. Local maxima closer than a defined refractory period of 300 ms to the preceding ones are dismissed. The result is a time series of pulse reference timings.

As is shown in 410, the foot IPG is low-pass filtered at 25 Hz with an 8-pole Butterworth filter and inverted (so that pulses have an upward peak). Segments starting from the timings extracted (415) from the Leg IPG (reference timings) and extending to 80% of the previous pulse interval, but no longer than one second, are defined in the Foot IPG. This defines the time windows where the Foot IPG is expected to occur, avoiding misdetection outside of these windows. In each segment, the derivative of the signal is computed, and the point of maximum positive derivative (maximum acceleration) is extracted. The foot of the IPG signal is then computed using an intersecting tangent method, where the fiducial (420) is defined by the intersection between a first tangent to the IPG at the point of maximum positive derivative and a second tangent to the minimum of the IPG on the left of the maximum positive derivative within the segment.

The time series resulting from this two-step extraction is then used in conjunction with another signal to facilitate additional processing. In the present disclosure, these timings are used as reference timings to improve the SNR of BCG signals to subsequently extract intervals between a timing of the BCG (typically the I-wave) and the Foot IPG for the purpose of computing the PWV, as previously disclosed in U.S. 2013/0310700 (Wiard). In certain embodiments, the timings of the Leg IPG are used as reference timings to improve the SNR of BCG signals, and the foot IPG timings are used to extract intervals between timing fiducials of the improved BCG (typically the I-wave) and the Foot IPG for the purpose of computing the PTT and the (PWV).

In certain embodiments, the processing steps include an individual pulse SNR computation after individual timings have been extracted, either in Leg IPG or Foot IPG. Following the computation of the SNRs, pulses with a SNR below a threshold value are eliminated from the time series, in order to prevent propagating noise in subsequent processing steps. The individual SNRs may be computed in a variety of methods known to a person skilled in the art. For instance, an estimated pulse can be computed by ensemble averaging segments of signal around the pulse reference timing. The noise associated with each pulse is defined as the difference between the pulse and the estimated pulse. The SNR is then the ratio of the root-mean-square (RMS) value of the estimated pulse over the RMS value of the noise for that pulse.

In certain embodiments, the time interval between the Leg IPG pulses, (as detected by the above-mentioned methods), and the Foot IPG pulses, also detected by the above-mentioned methods, is extracted. The Leg IPG measuring a pulse occurring earlier in the legs compared to the pulse from the Foot IPG, the interval between these two is related to the propagation speed in the lower body, i.e., the peripheral vasculature. This provides complementary information to the interval extracted between the BCG and the Foot IPG for instance, and can be used to decouple central versus peripheral vascular properties. It is also complementary to information derived from timings between the BCG and the Leg ICG.

FIG. 5 shows an example flowchart depicting signal processing to segment individual Foot IPG "beats" to produce an averaged IPG waveform of improved SNR, which is subsequently used to determine the fiducial of the averaged Foot IPG, consistent with various aspects of the present disclosure. Similar to the method shown in FIG. 4, the Leg IP and the Foot IPG are simultaneously measured (500), the Leg IPG is low-pass filtered (505), the foot IPG is low-pass filtered (510), and segments starting from the timings extracted (515) from the Leg IPG (reference timings). The segments of the Foot IPG extracted based on the Leg IPG timings are ensemble-averaged (520) to produce a higher SNR Foot IPG pulse. From this ensemble-averaged signal, the start of the pulse is extracted using the same intersecting tangent approach as described earlier. This approach enables the extraction of accurate timings in the Foot IPG even if the impedance signal is dominated by noise, as shown in FIG. 7b. These timings can then be used together with timings extracted from the BCG for the purpose of computing the PTT and (PWV). Timings derived from ensemble-averaged waveforms and individual waveforms can also be both extracted, for the purpose of comparison, averaging and error-detection.

Specific timings can be extracted from the IPG pulses (from either leg or foot) are related (but not limited) to the peak of the pulse, to the minimum preceding the peak, or to the maximum second derivative (maximum rate of acceleration) preceding the point of maximum derivative. An IPG pulse and the extraction of a fiducial (525) in the IPG can also be performed by several other signal processing methods, including (but not limited to) template matching, cross-correlation, wavelet-decomposition, or short window Fourier transform.

Figure 6B:
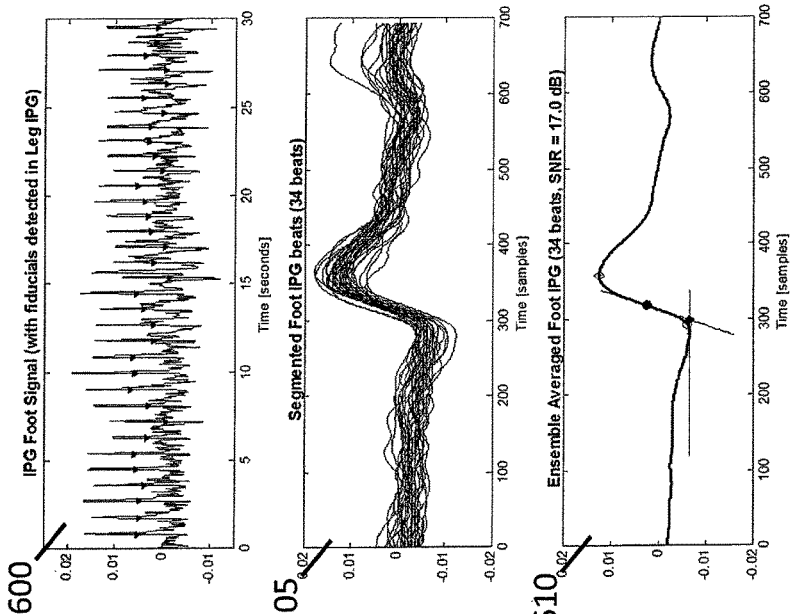
FIG. 6b shows examples of the Foot IPG signal with fiducials derived from the Leg IPG fiducials; the segmented Foot IPG into beats; and the ensemble-averaged Foot IPG beat with fiducials and calculated SNR, for an exemplary high-quality recording, consistent with various aspects of the present disclosure.
Figure 6A:
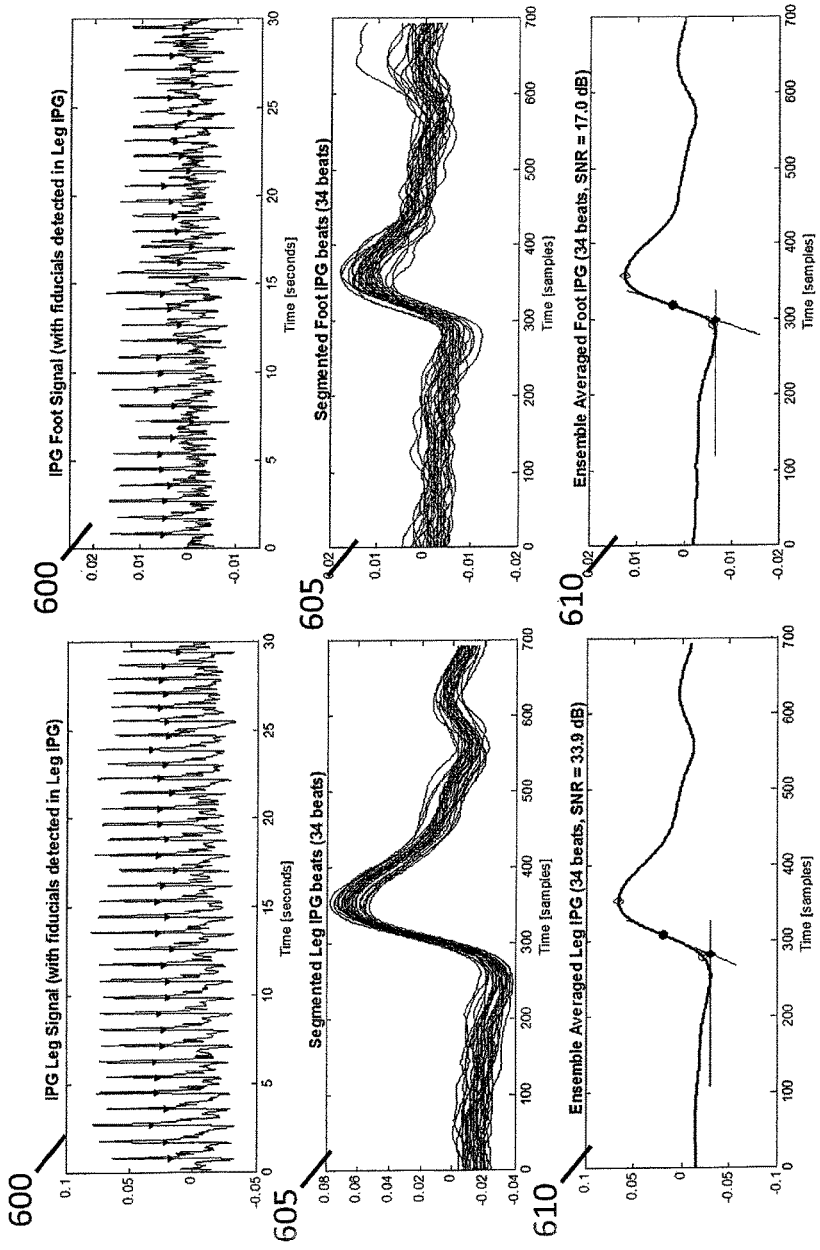
FIG. 6a shows examples of the Leg IPG signal with fiducials; the segmented Leg IPG into beats; and the ensemble-averaged Leg IPG beat with fiducials and calculated SNR, for an exemplary high-quality recording, consistent with various aspects of the present disclosure.

FIG. 6a shows examples of the Leg IPG signal with fiducials (plot 600); the segmented Leg IPG into beats (plot 605); and the ensemble-averaged Leg IPG beat with fiducials and calculated SNR (plot 610), for an exemplary high-quality recording, consistent with various aspects of the present disclosure. Additionally, FIG. 6b shows examples of the Foot IPG signal with fiducials derived from the Leg IPG fiducials (plot 600); the segmented Foot IPG into beats (plot 605); and the ensemble-averaged Foot IPG beat with fiducials and calculated SNR (plot 610), for an exemplary high-quality recording, consistent with various aspects of the present disclosure. FIG. 7a shows examples of the Leg IPG signal with fiducials (plot 700); the segmented Leg IPG into beats (plot 705); and the ensemble averaged Leg IPG beat with fiducials and calculated SNR (plot 710), for an exemplary low-quality recording, consistent with various aspects of the present disclosure. FIG. 7b shows examples of the Foot IPG signal with fiducials derived from the Leg IPG fiducials (plot 700); the segmented Foot IPG into beats (plot 705); and the ensemble-averaged Foot IPG beat with fiducials and calculated SNR (plot 710), for an exemplary low-quality recording, consistent with various aspects of the present disclosure.

Figure 8:
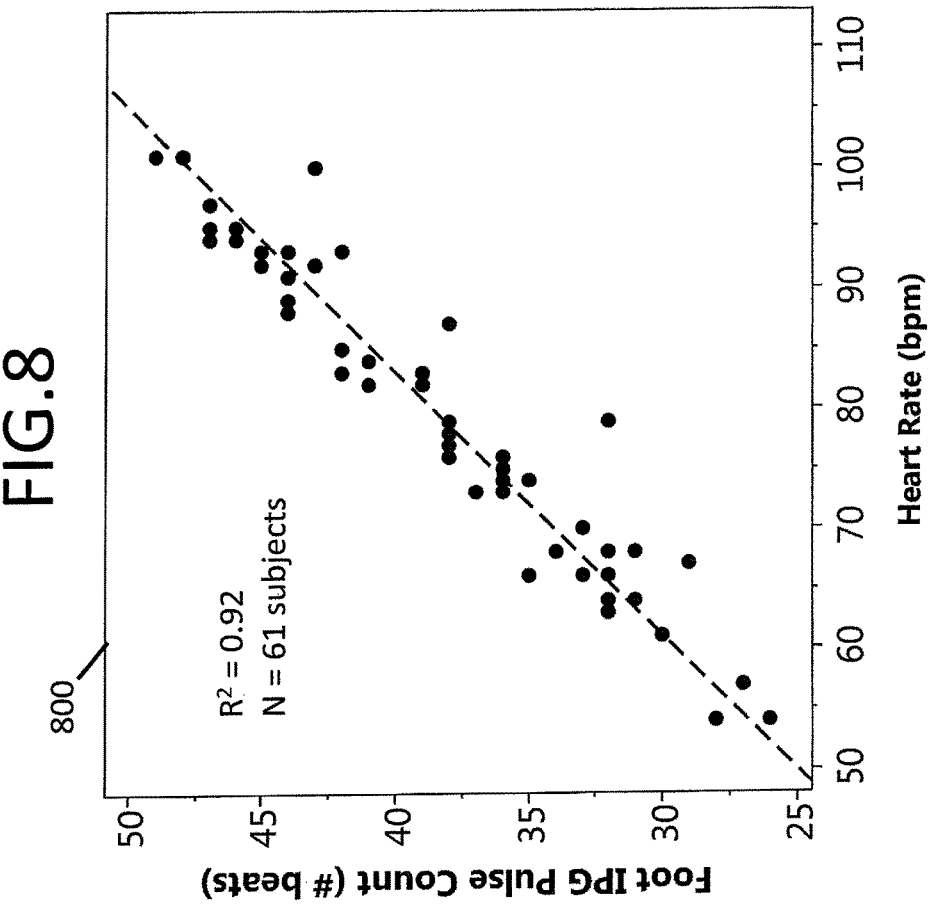
FIG. 8 shows an example correlation plot for the reliability in obtaining the low SNR Foot IPG pulse for a 30-second recording, using the first impedance signal as the trigger pulse, from a study including 61 test subjects with various heart rates, consistent with various aspects of the present disclosure.

FIG. 8 shows an example correlation plot 800 for the reliability in obtaining the low SNR Foot IPG pulse for a 30-second recording, using the first impedance signal as the trigger pulse, from a study including 61 test subjects with various heart rates, consistent with various aspects of the present disclosure.

In certain embodiments, a dual-Foot IPG is measured, allowing the detection of blood pressure pulses in both feet. Such information can be used for diagnostic of peripheral arterial diseases (PAD) by comparing the relative PATs in both feet to look for asymmetries. It can also be used to increase the robustness of the measurement by allowing one foot to have poor contact with electrodes (or no contact at all). SNR measurements can be used to assess the quality of the signal in each foot, and to select the best one for downstream analysis. Timings extracted from each foot can be compared and set to flag potentially inaccurate PWV measurements due to arterial peripheral disease, in the event these timings are different by more than a defined threshold. Alternatively, timings from both feet can be pooled to increase the overall SNR if their difference is below a defined threshold.

In certain embodiments, the disclosure is used to measure a PWV, where the IPG is augmented by the addition of BCG sensing into the weighing scale to determine characteristic fiducials between the BCG and Leg IPG trigger, or the BCG and Foot IPG. The BCG sensors are comprised typically of the same strain gage set used to determine the bodyweight of the user. The load cells are typically wired into a bridge configuration to create a sensitive resistance change with small displacements due to the ejection of the blood into the aorta, where the circulatory or cardiovascular force produce movements within the body on the nominal order of 1-3 Newtons. BCG forces can be greater than or less than the nominal range in cases such as high or low cardiac output.

Figure 10:
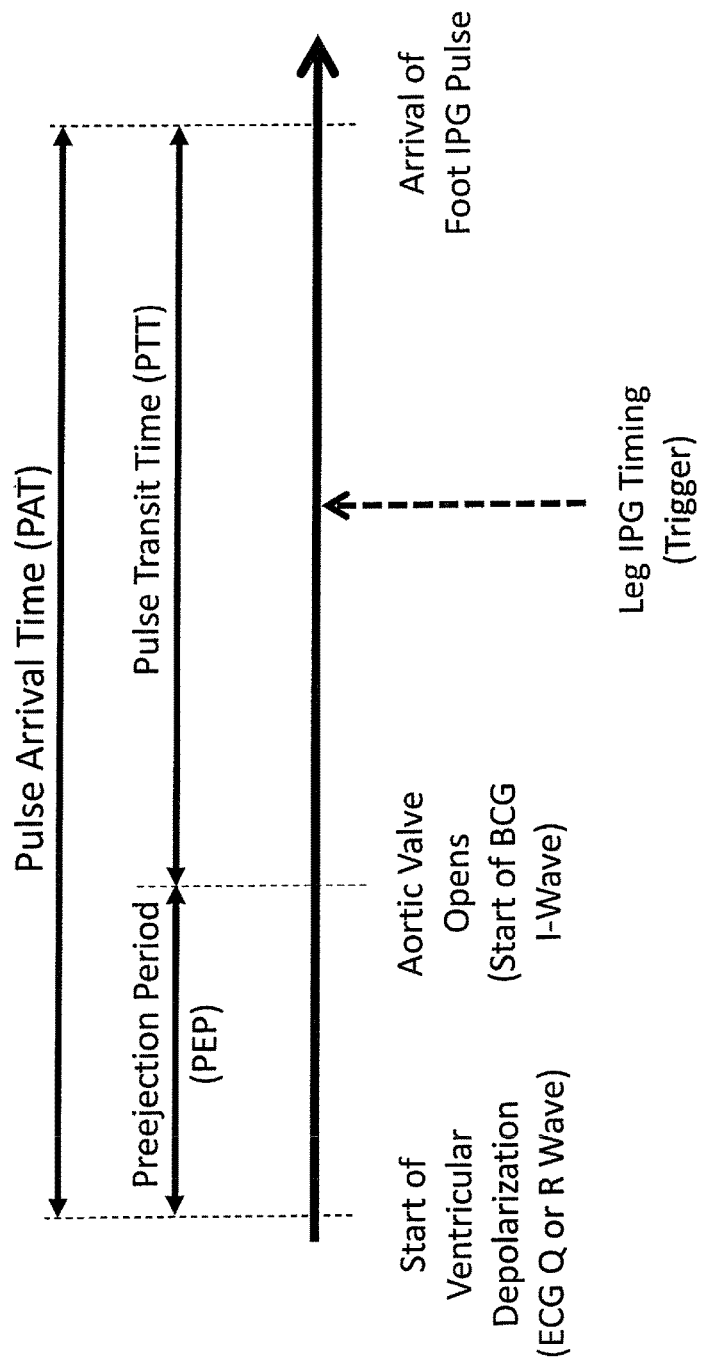
FIG. 10 shows nomenclature and relationships of various cardiovascular timings, consistent with various aspects of the present disclosure.

FIGS. 9a-b show example configurations to obtain the PTT, using the first IPG as the triggering pulse for the Foot IPG and BCG, consistent with various aspects of the present disclosure. The I-wave of the BCG 900 as illustrated normally depicts the headward force due to cardiac ejection of blood into the ascending aorta which can be used as a timing fiducial indicative of the pressure pulse initiation of the user's proximal aorta relative to the user's heart. The J-wave is also indicative of timings in the systole phase and also incorporates information related to the strength of cardiac ejection and the ejection duration. The K-Wave also provides systolic and vascular information of the user's aorta. The characteristic timings of these and other BCG waves can be used as fiducials that can be related to fiducials of the IPG signals of the present disclosure. FIG. 10 shows nomenclature and relationships of various cardiovascular timings, consistent with various aspects of the present disclosure.

FIG. 11 shows an example graph 1100 of PTT correlations for two detection methods (white dots) Foot IPG only, and (black dots) Dual-IPG method, consistent with various aspects of the present disclosure.

FIG. 12 shows an example graph 1200 of PWV obtained from the present disclosure compared to the ages of 61 human test subjects, consistent with various aspects of the present disclosure.

Figure 14B:
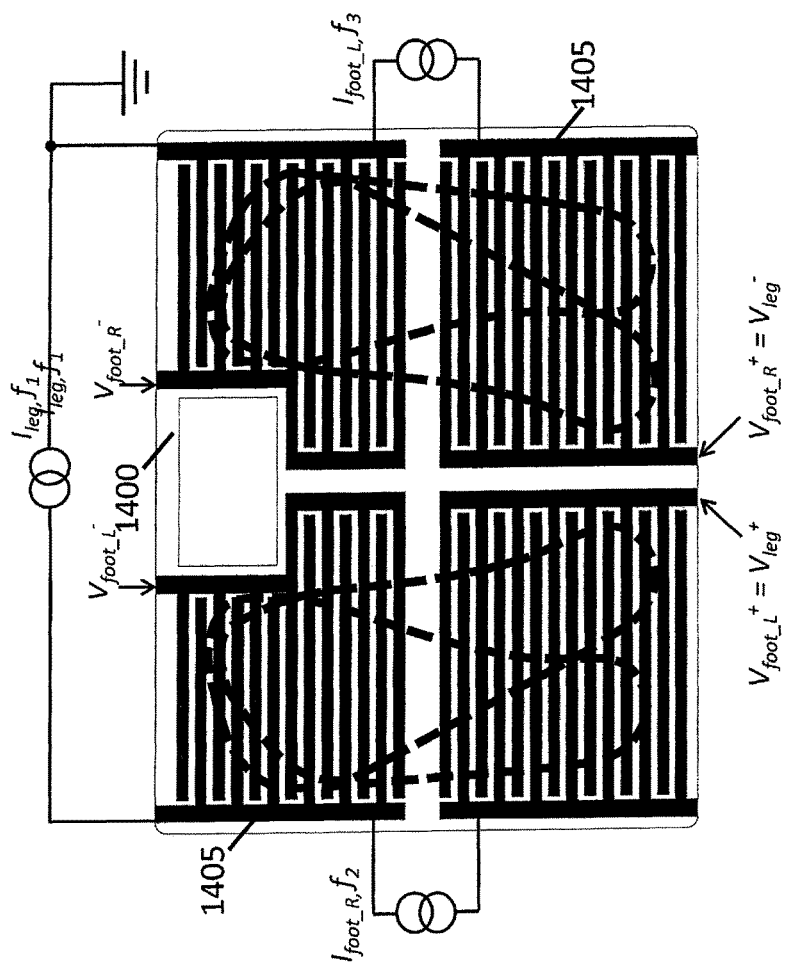
FIG. 14b shows another example of a scale with interleaved foot electrodes to inject and sense current from one foot to another foot, and measure Foot IPG signals in both feet, consistent with various aspects of the present disclosure.

FIG. 13 shows another example of a scale 1300 with interleaved foot electrodes 1305 to inject and sense current from one foot to another foot, and within one foot, consistent with various aspects of the present disclosure. FIG. 14*a-c* shows various examples of a scale 1400 with interleaved foot electrodes 1405 to inject and sense current from one foot to another foot, and measure Foot IPG signals in both feet, consistent with various aspects of the present disclosure. FIGS. 15*a-d* shows an example breakdown of a scale 1500 with interleaved foot electrodes 1505 to inject and sense current from one foot to another foot, and within one foot, consistent with various aspects of the present disclosure.

Figure 16:
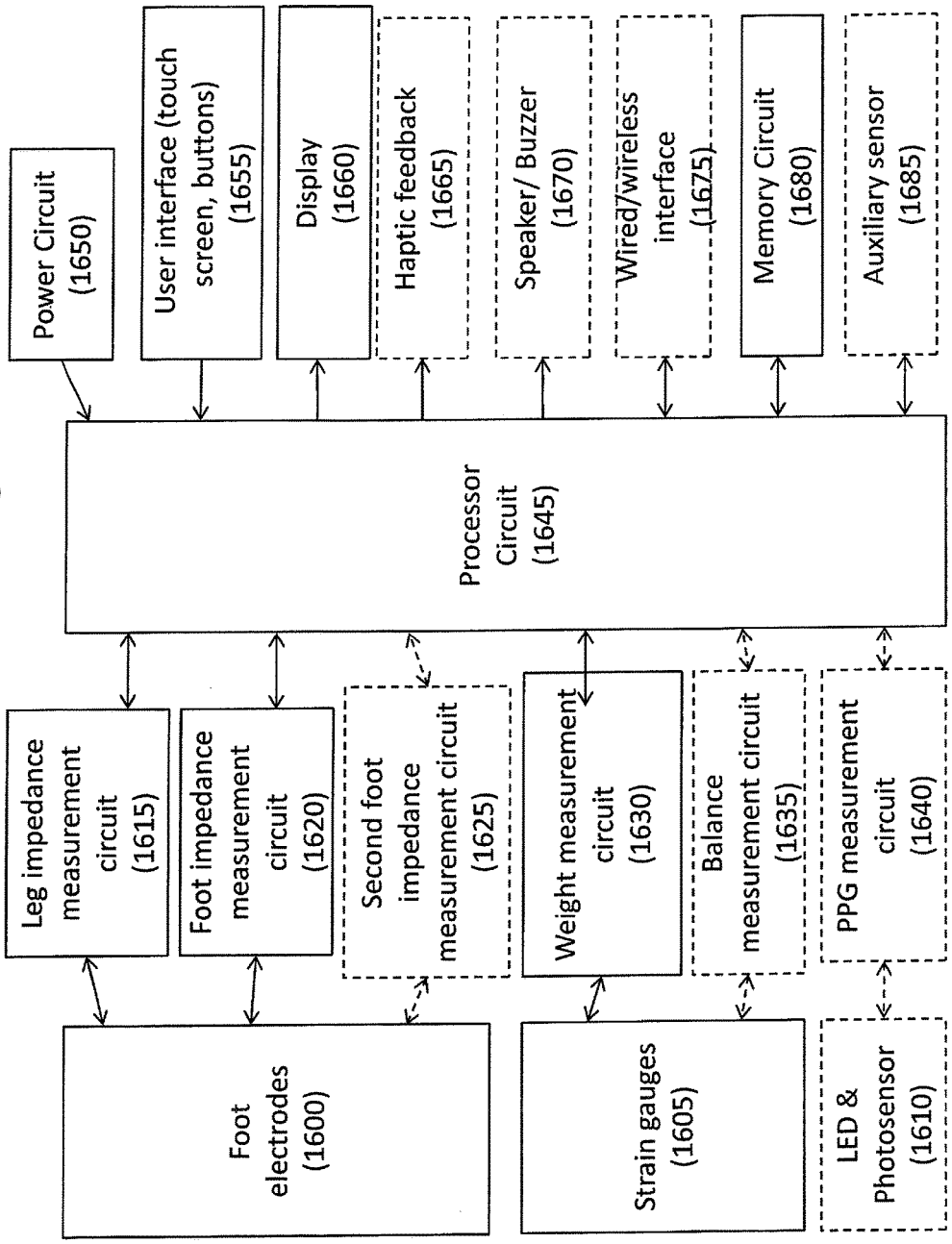
FIG. 16 shows an example block diagram of circuit-based building blocks, consistent with various aspects of the present disclosure.

FIG. 16 shows an example block diagram of circuit-based building blocks, consistent with various aspects of the present disclosure. The various circuit-based building blocks shown in FIG. 16 can be implemented in connection with the various aspects discussed herein. In the example shown, the block diagram includes foot electrodes 1600 that can collect the IPG signals. Further, the block diagram includes strain gauges 1605, and an LED/photosensor 1610. The foot electrodes 1600 is configured with a leg impedance measurement circuit 1615, a foot impedance measurement circuit 1620, and an optional second foot impedance measurement circuit 1625. The leg impedance measurement circuit 1615, the foot impedance measurement circuit 1620, and the optional second foot impedance measurement circuit 1625 report the measurements collected to a processor circuit 1645.

The processor circuit 1645 also collects data from a weight measurement circuit 1630 and an option balance measurement circuit 1635 that are configured with the strain gauges 1605. Further, an optional photoplethysmogram (PPG) measurement circuit 1640, which collects data from the LED/photosensor 1610, can also provide data to the processor circuit 1645.

The processor circuit 1645 is powered via a power circuit 1650. Further, the processor circuit 1645 also collects user input data from a user interface 1655 that can include a touch screen and/or buttons. The data collected/measured by the processor circuit 1645 is shown to the user via a display 1660. Additionally, the data collected/measured by the processor circuit 1645 can be stored in a memory circuit 1680. Further, the processor circuit 1645 can optionally control a haptic feedback circuit 1665, a speaker or buzzer 1670, a wired/wireless interface 1675, and an auxiliary sensor 1685.

Figure 17:
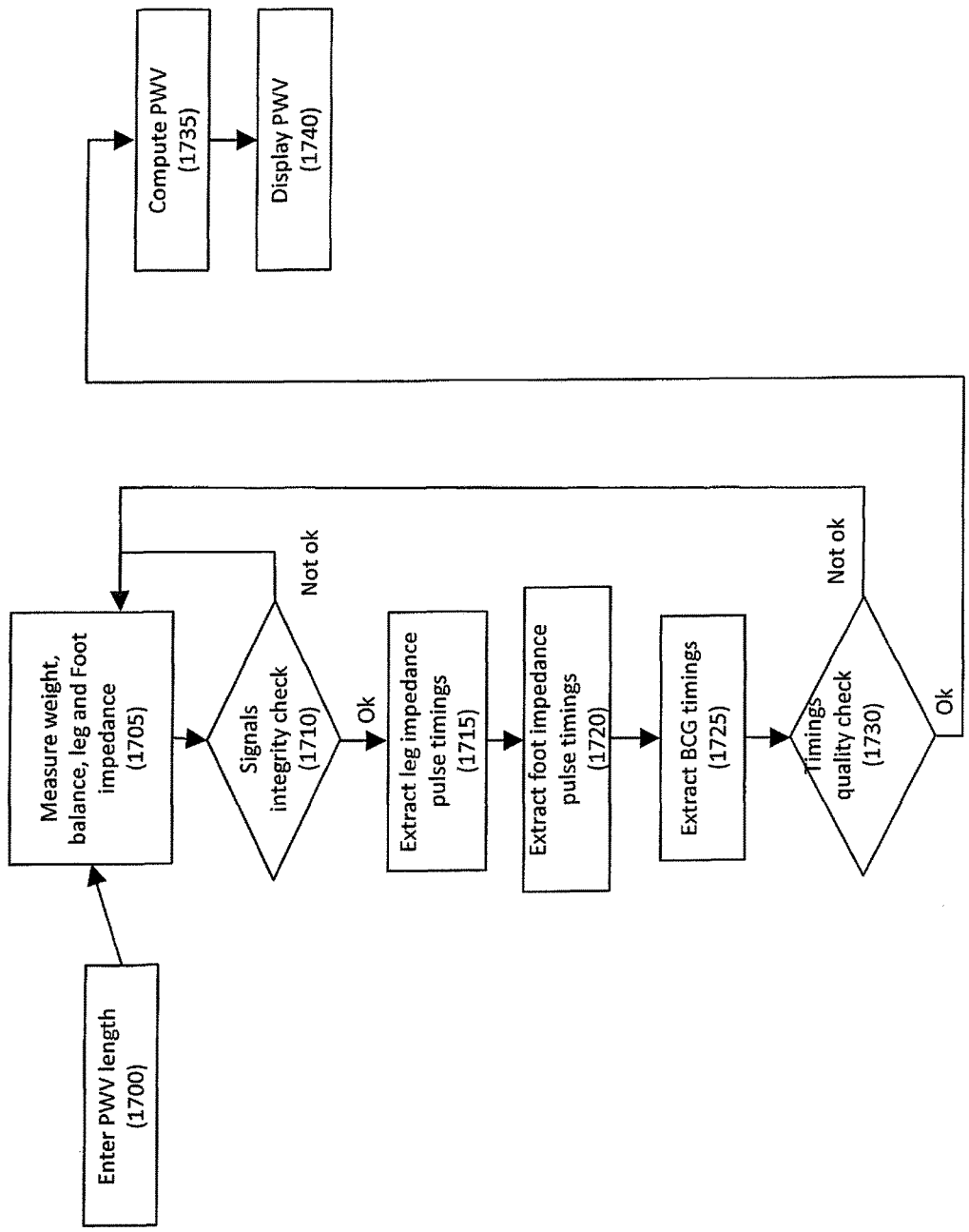
FIG. 17 shows an example flow diagram, consistent with various aspects of the present disclosure.

FIG. 17 shows an example flow diagram, consistent with various aspects of the present disclosure. As shown in block 1700, a PWV length is entered. As is shown in block 1705, a user's weight, balance, leg, and foot impedance are measured (as is consistent with various aspects of the present disclosure). As is shown at block 1710, the integrity of signals is checked (e.g., signal to noise ratio). If the signal integrity check is not met, the user's weight, balance, leg, and foot impedance are measured again (block 1705), if the signals integrity check is met, the leg impedance pulse timings are extracted (as is shown at block 1715). As is shown at block 1720, foot impedance and pulse timings are then extracted, and as is shown at block 1725, BCG timings are extracted. As is shown at block 1730, a timings quality check is performed. If the timings quality check is not validated, the user's weight, balance, leg and foot impedance are again measured (block 1705). If the timings quality check is validated, the PWV is calculated (as is shown at block 1735). Finally, as is shown at block 1740, the PWV is then displayed to the user.

Figure 18:
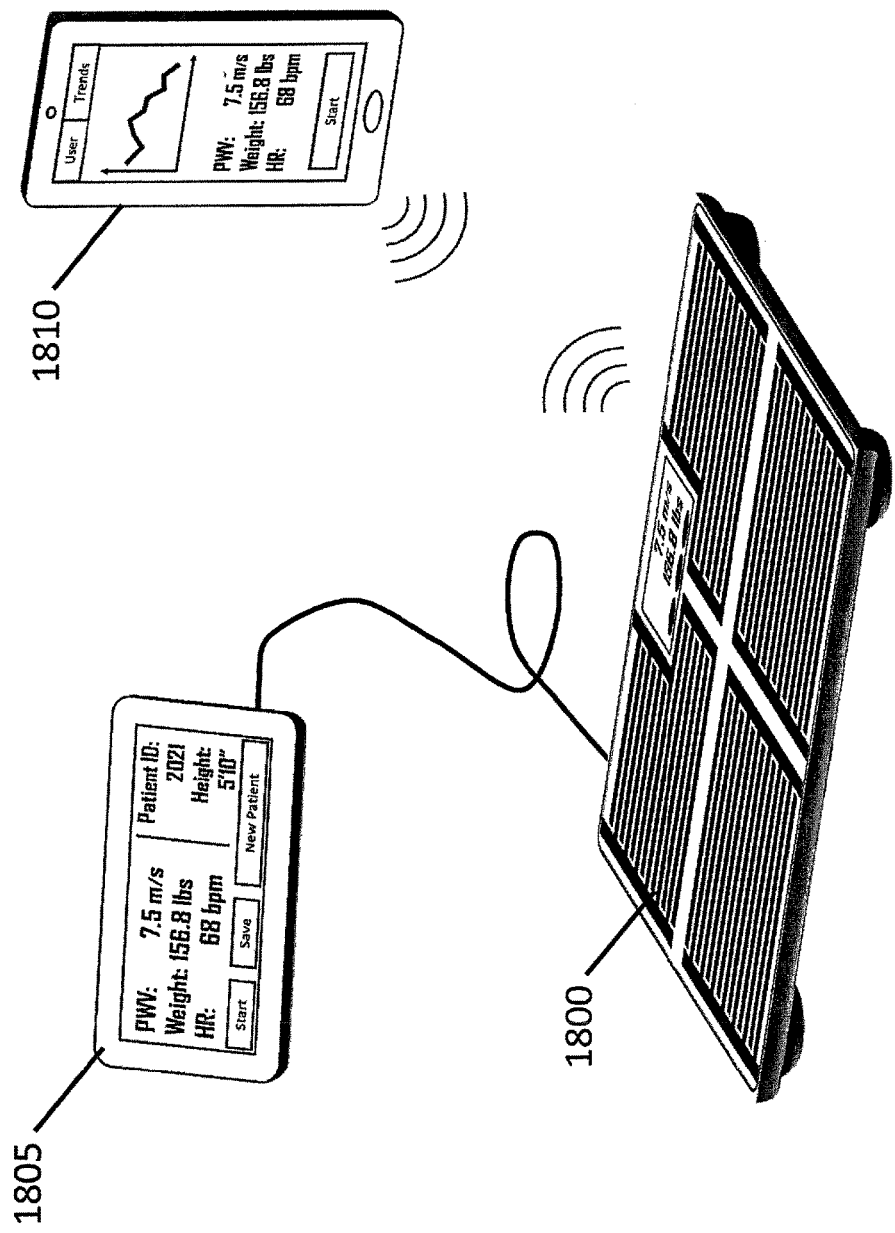
FIG. 18 shows an example scale communicatively coupled to a wireless device, consistent with various aspects of the present disclosure.

FIG. 18 shows an example scale 1800 communicatively coupled to a wireless device, consistent with various aspects of the present disclosure. As described herein, a display 1805 displays the various aspects measured by the scale 1800. The scale can also wirelessly broadcast the measurements to a wireless device 1810.

FIGS. 19*a-c* show example impedance as measured through different parts of the foot based on the foot position, consistent with various aspects of the present disclosure. For instance, example impedance measurement configurations may be implemented using a dynamic electrode configuration for measurement of foot impedance and related timings, consistent with various aspects of the present disclosure. Dynamic electrode configuration may be implemented using independently-configurable electrodes to optimize the impedance measurement. As shown in FIG. 19*a*, interleaved electrodes 1900 are connected to an impedance processor circuit 1905 to determine foot length, foot position, and/or foot impedance. As is shown in FIG. 19*b*, an impedance measurement is determined regardless of foot position 1910 based on measurement of the placement of the foot across the electrodes 1900. This is based in part in the electrodes 1900 that are engaged (blackened) and in contact with the foot (based on the foot position 1910), which is shown in FIG. 19*c*.

More specifically regarding FIG. 19*a*, configuration can include connection/de-connection of the individual electrodes 1900 to the impedance processor circuit 1905, their configuration as current-carrying electrodes (injection or return), sense electrodes (positive or negative), or both. The configuration can either be preset based on user information, or updated at each measurement (dynamic reconfiguration) to optimize a given parameter (impedance SNR, measurement location). The system may for instance algorithmically determine which electrodes under the foot to use in order to obtain the highest SNR in the pulse impedance signal. Such optimization algorithm may include iteratively switching configurations and measuring the resulting impedance, then selecting the best suited configuration. Alternatively, the system may first, through a sequential impedance measurement between each individual electrode 1900 and another electrode in contact with the body (such as an electrode in electrode pair 205 on the other foot), determine which electrodes are in contact with the foot. By determining the two most apart electrodes, the foot size is determined. Heel location can also be determined in this manner, as can other characteristics such as foot arch type. These parameters can then be used to determine programmatically (in an automated manner by CPU/logic circuitry) which electrodes should be selected for current injection and return (as well as sensing if a Kelvin connection issued) in order to obtain the best foot IPG.

In various embodiments involving the dynamically reconfigurable electrode array 1900/1905, an electrode array set is selected to measure the same portion (or segment) of the foot, irrespective of the foot location on the array. FIG. 19*b* illustrates the case of several foot positions on a static array (a fixed set of electrodes are used for measurement at the heel and plantar/toe areas, with a fixed gap of an inactive electrode or insulating material between them). Depending on the position of the foot, the active electrodes are contacting the foot at different locations, thereby sensing a different volume (or segment) of the foot. If the IPG is used by itself (e.g., for heart measurement), such discrepancies may be non-consequential. However, if timings derived from the IPG are referred to other timings (e.g., R-wave from the ECG, or specific timing in the BCG), such as for the calculation of a PTT or PWV, the small shifts in IPG timings due to the sensing of slightly different volumes in the foot (e.g., if the foot is not always placed at the same position on the electrodes) can introduce an error in the calculation of the interval. Such location variations can readily occur in the day-to-day use of the scale. With respect to FIG. 19b for instance, the timing of the peak of the IPG from the foot placement on the right (sensing the toe/plantar region) would be later than from the foot placement on the left, which senses more of the heel volume (the pulse reaches first the heel, then the plantar region). Factors influencing the magnitude of these discrepancies include foot shape (flat or not) and foot length.

Various embodiments address challenges relating to foot placement. FIG. 19c shows an example embodiment involving dynamic reconfiguration of the electrodes to reduce such foot placement-induced variations. As an example, by sensing the location of the heel first (as described above), it is possible to activate only a subset of electrodes under the heel, and another subset of electrodes separated by a fixed distance (1900). The other electrodes (e.g., unused electrodes) are left disconnected. The sensed volume will therefore always be the same, producing consistent timings. The electrode configuration leading to the most consistent results may also be informed by the foot impedance, foot length, the type of arch (all of which can be measured by the electrode array as shown above), but also by the user ID (foot information can be stored for each user, then looked up based on automatic user recognition or manual selection (e.g., in a look-up-table stored for each user in a memory circuit accessible by the CPU circuit in the scale).

Accordingly, in certain embodiments, the impedance-measurement apparatus measures impedance using a plurality of electrodes contacting one foot and with at least one other electrode (typically many) at a location distal from the foot. The plurality of electrodes (contacting the one foot) is arranged on the platform and in a pattern configured to inject current signals and sense signals in response thereto, for the same segment of the foot so that the timing of the pulse-based measurements does not vary simply because the user placed the one foot at a slightly different position on the platform or scale. Thus, in FIG. 19a, the foot-to-electrode locations for the heel are different locations than that shown in FIGS. 19b and 19c. As this different foot placement might occur from day to day for the user, the timing and related impedance measurements should be for the same (internal) segment of the foot. By having the computer processor circuit inject current and sense responsive signals to first locate the foot on the electrodes (e.g., sensing where positions of the foot's heel plantar regions and/or toes), the pattern of foot-to-electrode locations permits the foot to move laterally, horizontally and both laterally and horizontally via the different electrode locations, while collecting impedance measurements relative to the same segment of the foot.

The BCG/IPG system can be used to determine the PTT of the user, by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. In certain embodiments, the BCG/IPG system is used to determine the PWV of the user, by identification of the characteristic length representing the length of the user's arteries, and by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. The system of the present disclosure and alternate embodiments may be suitable for determining the arterial stiffness (or arterial compliance) and/or cardiovascular risk of the user regardless of the position of the user's feet within the bounds of the interleaved electrodes. In certain embodiments, the weighing scale system incorporated the use of strain gage load cells and six or eight electrodes to measure a plurality of signals including: bodyweight, BCG, body mass index, fat percentage, muscle mass percentage, and body water percentage, heart rate, heart rate variability, PTT, and PWV measured simultaneously or synchronously when the user stands on the scale to provide a comprehensive analysis of the health and wellness of the user.

In other certain embodiments, the PTT and PWV are computed using timings from the Leg IPG or Foot IPG for arrival times, and using timings from a sensor located on the upper body (as opposed to the scale measuring the BCG) to detect the start of the pulse. Such sensor may include an impedance sensor for impedance cardiography, a hand-to-hand impedance sensor, a photoplethysmogram on the chest, neck, head, arms or hands, or an accelerometer on the chest (seismocardiograph) or head.

Communication of the biometric information is another aspect of the present disclosure. The biometric results from the user are then stored in the memory on the scale and displayed to the user via a display on the scale, audible communication from the scale, and/or the data is communicated to a peripheral device such as a computer, smart phone, tablet computing device. The communication occurs directly to the peripheral device with a wired connection, or can be sent to the peripheral device through wireless communication protocols such as Bluetooth or WiFi. Computations such as signal analyses described therein may be carried out locally on the scale, in a smartphone or computer, or in a remote processor (cloud computing).

Other aspects of the present disclosure are directed toward apparatuses or methods that include the use of at least two electrodes that contacts feet of a user. Further, circuitry is provided to determine a pulse arrival time at the foot based on the recording of two or more impedance signals from the set of electrodes. Additionally, a second set of circuitry is provided to extract a first pulse arrival time from a first impedance signal and use the first pulse arrival time as a timing reference to extract and process a second pulse arrival time in a second impedance signal.

Reference may also be made to published patent documents U.S. Patent Publication 2010/0094147 (now U.S. Pat. No. 8,870,780) and U.S. Patent Publication 2013/0310700 (now U.S. Pat. No. 9,011,346), which are, together with the references cited therein, herein fully incorporated by reference for the purposes of sensors and sensing technology. The aspects discussed therein may be implemented in connection with one or more of embodiments and implementations of the present disclosure (as well as with those shown in the figures). In view of the description herein, those skilled in the art will recognize that many changes may be made thereto without departing from the spirit and scope of the present disclosure.

As illustrated herein, various circuit-based building blocks and/or modules may be implemented to carry out one or more of the operations and activities described herein shown in the block-diagram-type figures. In such contexts, these building blocks and/or modules represent circuits that carry out one or more of these or related operations/activities. For example, in certain of the embodiments discussed above (such as the pulse circuitry modularized as shown in FIGS. 3a-b), one or more blocks/modules are discrete logic circuits or programmable logic circuits configured and arranged for implementing these operations/activities, as in the circuit blocks/modules shown. In certain embodiments, the programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules/blocks include a combination of a CPU hardware-based circuit and a set of instructions in the form of firmware, where the first module/block includes a first CPU hardware circuit with one set of instructions and the second module/block includes a second CPU hardware circuit with another set of instructions.

Accordingly, aspects of the present disclosure are directed to, inter alia, the following apparatuses, systems, and/or methods:

Measuring a pulse arrival time at the foot based on the recording of two or more simultaneous impedance signals from a set of electrodes in contact with the feet, in which:
at least a first impedance signal is measured from one foot to another body region (e.g., the other foot),
at least a second impedance signal is measured within one foot, and
a first pulse arrival time is extracted from a first impedance signal, and is used as timing reference to extract and process a second pulse arrival time in a second impedance signal.

The first pulse arrival time can be used as a timing reference for processing a third signal containing synchronous information (e.g., BCG or impedance cardiogram).

The second pulse arrival time can be used as a timing reference for processing a third signal containing synchronous information (e.g., BCG or impedance cardiogram).

A PTT can be measured by taking the difference between the pulse arrival time at the foot and a timing derived from a simultaneously-measured signal (e.g., BCG or impedance cardiogram).

A PTT can be measured by taking the difference between the second pulse arrival time and the first pulse arrival time.

A third impedance signal can be measured in the second foot, and, a first pulse arrival time can be extracted from a first impedance signal, and is used as timing reference to extract and process a third pulse arrival time in a third impedance signal.

A computation of a PWV from the first and either of the second or third timings can be flagged as potentially inaccurate based on a difference between the second and third pulse arrival times higher than a defined threshold.

A computation of a PWV can be performed from the first timing and the pooled timings extracted from the second and third impedance signals, if the difference between the second and third pulse arrival times is lower than a defined threshold.

A sensor for measuring the electrical impedance of a foot, using at least one set of two electrodes for excitation and sensing respectively, whereas electrode contacts are interleaved over an area so as to always provide a similar area of contact with the foot for each electrode irrespectively of the foot position within the limits of the overall electrode area.

The first set of two electrodes can be in contact with the back of the foot, and a second set of two electrodes can provide contact with the front of the foot, and, the two sets of electrodes can be connected in a Kelvin configuration for impedance measurement.

The spacing between the first set of electrode contacting the back of the foot and the second set of electrodes contacting the front of the foot can be larger than 20 mm.

The set of electrodes can include two inter-digitated electrodes.

The set of electrodes can include of an array contacts, whereas every other contact is connected the same electrode.

Based upon the above discussion and illustrations, those skilled in the art will readily recognize that various modifications and changes may be made to the present disclosure without strictly following the exemplary embodiments and applications illustrated and described herein. For example, the input terminals as shown and discussed may be replaced with terminals of different arrangements, and different types and numbers of input configurations (e.g., involving different types of input circuits and related connectivity). Such modifications do not depart from the true spirit and scope of the present disclosure, including that set forth in the following claims.

What is claimed is:

1. A method comprising:
providing a CPU and a memory circuit with user-corresponding data stored in the memory circuit, and a platform over which a plurality of electrodes are interleaved and configured and arranged for engaging a user, wherein the platform is configured and arranged with at least three electrodes for carrying out leg and foot impedance cardiovascular measurements via the feet of the user and is further configured and arranged with a display integrated in the platform for conveying cardiovascular information to the user while the user is on the platform;
while the plurality of electrodes are concurrently contacting a limb of the user, operating circuitry configured for automatically obtaining a plurality of measurement signals from the plurality of electrodes, including fiducial cardiovascular timings corresponding to blood pulsations flowing down a leg and a foot of the user, the circuitry having a reduced power-consumption mode of operation and at least one higher power-consumption mode of operation;
before obtaining a plurality of measurement signals by operating the circuitry, using a signal-sense circuit to sense signals indicative of the user approaching or engaging the platform and, in response, causing the circuitry to transition from the reduced power-consumption mode of operation and at least one higher power-consumption mode of operation; and
after the circuitry is operating in the at least one higher power-consumption mode of operation, causing the CPU to access the user-corresponding data stored in the memory circuit and thereafter cause a plurality of impedance-measurement signals to be obtained by using the at least three electrodes while they are contacting the user via the platform, and selecting certain of the electrodes under the platform for measurement results in response to a quality of the plurality of impedance-measurement signals collected, and, therefrom, via the CPU, generating signals corresponding to cardiovascular timings of the user and sending output signals as derived from the collected impedance-measurement signals for review of the user's cardiovascular attributes.

2. The method of claim 1, wherein the signal-sense circuit is a motion detection circuit configured and arranged to wake up the CPU and thereby cause the CPU to transition from the reduced power-consumption mode of operation and to the at least one higher power-consumption mode of operation.

3. The method of claim 1, wherein the signal-sense circuit includes a passive infrared detector and a processor for evaluating whether radiation from the passive infrared detector is indicative of a human.

4. The method of claim 1, wherein the platform is over and integrated with both a display and a wireless communications circuit, wherein in response to the CPU accessing the user-corresponding data stored in the memory circuit, the CPU selects one of a plurality of different types of user-discernible information and presents the user-discernible information to the user via the display, and wherein after causing the plurality of impedance-measurement signals to be obtained, using wireless communications circuitry to communicate cardio-vascular information wirelessly, derived from the plurality of impedance-measurement signals, between the CPU and an external circuit which is not under the platform.

5. The method of claim 1, wherein the platform, over which the plurality of electrodes are interleaved and configured and arranged for engaging the user, is: a housing enclosing a circuit configured and arranged for permitting the user to stand on the platform and visualize information at the display in the platform and under the user; and a wireless communications circuit, wherein after causing the plurality of impedance-measurement signals to be obtained, using the wireless communications circuit to communicate cardio-vascular information wirelessly, derived from the plurality of impedance-measurement signals, between the CPU and an external circuit which is not under the platform.

6. The method of claim 1, wherein the platform, over which the plurality of electrodes are interleaved and configured and arranged for engaging the user, is a housing enclosing a circuit configured and arranged for permitting the user to stand on the platform and visualize information at the display in the platform and under the user; and wherein in response to the CPU accessing the user-corresponding data stored in the memory circuit, the CPU selects one of a plurality of different types of user-discernible information and presents the user-discernible information to the user through the display visually.

7. The method of claim 1, wherein the signal-sense circuit includes a passive infrared (PIR) circuit, and wherein the circuitry is responsive to the signal-sense circuit and to a motion detection indication provided by the CPU, whereby the CPU is programmed to assess data generated by the PIR circuit.

8. The method of claim 1, wherein the signal-sense circuit includes a passive infrared (PIR) circuit, and wherein the circuitry is responsive to the signal-sense circuit and to a motion detection indication provided by the CPU.

9. The method of claim 1, wherein the platform, over which the plurality of electrodes are interleaved and configured and arranged for engaging the user, is a housing enclosing a circuit configured and arranged for permitting the user to stand on the platform and communicate information between the platform to the user; and wherein in response to the CPU accessing the user-corresponding data stored in the memory circuit, the CPU selects one of a plurality of different types of user-discernible information and presents the user-discernible information to the user via the display.

10. The method of claim 9, wherein the user-discernible information includes an indication that the CPU is ready to cause the plurality of impedance-measurement signals to be obtained by using the plurality of electrodes while they are contacting the user.

11. The method of claim 1, wherein the platform, over which the plurality of electrodes are interleaved and configured and arranged for engaging the user, is a housing enclosing a circuit configured and arranged for permitting the user to stand on the platform and communicating information between the platform to the user; and
wherein in response to the CPU accessing the user-corresponding data stored in the memory circuit, the CPU selects one of a plurality of different types of user-discernible information and presents the user-discernible information to the user through the platform via a foot-tactile vibration.

12. The method of claim 11, wherein the user-discernible information includes an indication that the CPU is ready to cause the plurality of impedance-measurement signals to be obtained by using the plurality of electrodes while they are contacting the user.

13. The method of claim 1, wherein obtaining the plurality of impedance-measurement signals includes obtaining at least two impedance-measurement signals between one location at one foot of the user and another location of the user.

14. The method of claim 1, wherein obtaining the plurality of impedance-measurement signals includes obtaining at least two impedance-measurement signals between one location at one foot of the user and another location, and wherein the plurality of interleaved electrodes are connected to a CPU circuit which is configured and arranged to assess physiological attributes measured and indicated by the stored data as corresponding to the one foot.

15. The method of claim 1, wherein the platform, over which the plurality of electrodes are interleaved and configured and arranged for engaging the user, is a housing enclosing a circuit and a weighing scale configured and arranged for permitting the user to stand on the platform, wherein obtaining the plurality of impedance-measurement signals includes obtaining at least two impedance-measurement signals between one foot of the user and another location of the user, and wherein the plurality of interleaved electrodes are configured to provide measurement results that indicate one or more of the following user-specific attributes as being indicative or common to the user: foot impedance, foot length, and type of arch, and wherein one or more of the user-specific attributes are accessed, by being read or stored, in the memory circuit and identified as being specific to the user.

16. The method of claim 1, further including obtaining a signal, based on a timing reference obtained from the plurality of interleaved electrodes, that is indicative of synchronous information obtained from the user and that corresponds to information in a ballistocardiogram (BCG).

17. The method of claim 1, further including conveying modulated current between selected ones of the plurality of electrodes and wherein obtaining a plurality of impedance-measurement signals includes obtaining the impedance-measurement signals in response to the modulated current.

18. The method of claim 1, further including providing an impedance plethysmography (IPG) measurement within one foot of the user, while the one foot is engaging the electrodes.

19. An apparatus comprising:
a CPU and a memory circuit with user-corresponding data stored in the memory circuit, a platform over which a plurality of electrodes are interleaved and configured and arranged for engaging a user and configured and arranged with a display visible through the platform for conveying cardiovascular information to the user, the plurality of electrodes being integrated and communicatively connected with the CPU and wherein the platform is arranged with at least three electrodes;
circuitry configured and arranged for automatically obtaining a plurality of measurement signals from the plurality of electrodes, including fiducial cardiovascular timings corresponding to blood pulsations flowing down a leg and a foot of the user while the user is standing on and engaged with the platform, the circuitry having a reduced power-consumption mode of operation and at least one higher power-consumption mode of operation; and
the CPU, the memory circuit and the plurality of electrodes being configured and arrange to:
while the plurality of electrodes are concurrently contacting a limb of the user, operating the circuitry and therefrom automatically obtaining the plurality of measurement signals from the plurality of electrodes and selecting certain of the electrodes under the platform for measurement results in response to a quality of the plurality of measurement signals collected using the plurality of electrodes;
before obtaining a plurality of measurement signals by operating the circuitry, using a signal-sense circuit to sense signals indicative of the user approaching or engaging the platform and, in response, causing the circuitry to transition from the reduced power-consumption mode of operation and at least one higher power-consumption mode of operation; and
after the circuitry is operating in the at least one higher power-consumption mode of operation, causing the CPU to access the user-corresponding data stored in the memory circuit and thereafter cause a plurality of impedance-measurement signals to be obtained by using the plurality of electrodes while they are contacting the user via the platform and, therefrom, generating signals corresponding to cardiovascular timings of the user.

20. The apparatus of claim 19, further including a camera configured and arranged to be activated in response to a motion detection indication and to capture at least one image of the user while the user is on the platform, wherein the CPU is further configured and arranged to store said at least one image of the user in the memory circuit for retrieval at a later time for verification of correspondence between the user and biometric or physiological data stored as being specific to the user.

21. The apparatus of claim 20, wherein the memory circuit includes data-access to the memory circuit in response to an authorized access protocol, and wherein the CPU is further configured and arranged to permit remote access to the memory circuit by an authorized agent of medical or security personnel by using the authorized access protocol.

22. The apparatus of claim 19, further including a housing that is part of or secured to the platform, wherein the housing encloses the CPU, the memory circuit and one or more of the following:
the signal-sense circuit configured to include a passive infrared (PIR) circuit, and wherein the circuitry is responsive to the signal-sense circuit and to a motion detection indication provided by the CPU;
a CPU-executable module configured and arranged for obtaining from the plurality of impedance-measurement signals measurement results that indicate one or more of the following user-specific attributes as being indicative or common to the user: foot impedance, foot length, and type of arch, and wherein one or more of the user-specific attributes are accessed, by being read or stored, in the memory circuit and identified as being specific to the user;
a CPU-executable module configured and arranged for obtaining a signal, based on a timing reference obtained from the plurality of interleaved electrodes, that is indicative of synchronous information obtained from the user and that corresponds to information in a ballistocardiogram (BCG);
a CPU-executable module configured and arranged for conveying modulated current between selected ones of the plurality of electrodes; and
a CPU-executable module configured and arranged for providing an impedance plethysmography (IPG) measurement within one foot of the user, while the one foot is engaging the electrodes.

* * * * *